US011819592B2

(12) United States Patent
Garcia et al.

(10) Patent No.: US 11,819,592 B2
(45) Date of Patent: Nov. 21, 2023

(54) ADSORPTION OF PROTEINS ON CONDUCTING SURFACES UPON APPLICATION OF EXTERNAL POTENTIAL

(71) Applicants: Carlos D. Garcia, San Antonio, TX (US); Thomas E. Benavidez, San Antonio, TX (US); Rena Bizios, San Antonio, TX (US)

(72) Inventors: Carlos D. Garcia, San Antonio, TX (US); Thomas E. Benavidez, San Antonio, TX (US); Rena Bizios, San Antonio, TX (US)

( * ) Notice: Subject to any disclaimer, the term of this patent is extended or adjusted under 35 U.S.C. 154(b) by 289 days.

(21) Appl. No.: 14/518,713

(22) Filed: Oct. 20, 2014

(65) Prior Publication Data
US 2015/0110848 A1 Apr. 23, 2015

Related U.S. Application Data

(60) Provisional application No. 61/892,819, filed on Oct. 18, 2013.

(51) Int. Cl.
A61L 31/16 (2006.01)
G01N 33/543 (2006.01)

(52) U.S. Cl.
CPC ........ A61L 31/16 (2013.01); G01N 33/54393 (2013.01); A61L 2300/252 (2013.01); A61L 2400/18 (2013.01); A61L 2420/02 (2013.01)

(58) Field of Classification Search
None
See application file for complete search history.

(56) References Cited

U.S. PATENT DOCUMENTS

2008/0248972 A1* 10/2008 Nishizawa ........... G01N 33/543
506/32
2014/0166485 A1* 6/2014 Sailor .................. G01N 27/447
204/548

OTHER PUBLICATIONS

Brusatori et al., Protein Adsorption Kinetics under an Applied Electric Field: An Optical Waveguide Lightmode Spectroscopy Study, Langmuir 2003, 19, 5089-5097.*
Rabe et al, Understanding protein adsorption phenomena at solid surfaces, Advances in Colloid and Interface Science 162 (2011) 87-106.*
Fraajie et al., Orientation of adsorbed cytochrome c as a function of the electrical potential of the interface studied by total internal reflection fluorescence, Biophys. J., vol. 57 May 1990, p. 965-975.*
Tassel, Protein Adsorption Kinetics: Influence of Substrate Electric Potential, Principles and Practice Proteins at Solid-Liquid Interfaces Philippe Déjardin (Ed.), 2006.*
Ying et al., Adsorption of human serum albumin onto gold: a combined electrochemical and ellipsometric study, Journal of Colloid and Interface Science 279 (2004) 95-99.*
Marini et al., Potentiometric Titration curves of oxidized and reduced horse heart cytochrome c, Biopolymers, vol. 19, pp. 885-898, 1980 (Year: 1980).*
Palecek et al., Ionic strength-dependent structural transition of proteins at electrode surfaces, Chem. Commun., 2009, 1685-1687 (Year: 2009).*
Ramsden et al., Effect of Ionic Strength on Protein Adsorption Kinetics, J. Phys. Chem. 1994, 98, 5376-5381 (Year: 1994).*
Hepes, Hepes Buffer recipe, Buffer recipe from the Centre for Proteome Research, Webpage, 2021 (Year: 2021).*
Heli, H., et al. "Adsorption of human serum albumin onto glassy carbon surface—Applied to albumin-modified electrode: Mode of protein-ligand interactions." Journal of Electroanalytical Chemistry 610.1 (2007): 67-74. (Year: 2007).*
Wooten et al., On the Direct Electron Transfer, Sensing, and Enzyme Activity in the Glucose Oxidase/Carbon Nanotubes System, Anal. Chem., 86:752-757 (2014).
Baker et al., Electrostatics of nanosystems: Application to microtubules and the ribosome, PNAS, 98:10037-10041 (2001).
Wilson et al., Glucose oxidase: an ideal enzyme, Biosensors & Bioelectronics, 7:165-185 (1992).
Miller et al., Interior and Surface of Monomeric Proteins, J. Mol. Biol., 196:641-656 (1987).
Bankar et al., Glucose oxidase—An overview, Biotechnology Advances, 27:489-501 (2009).
Salis et al., Measurements and Theoretical Interpretation of Points of Zero Charge/Potential of BSA Protein, Langmuir, 27:11597-11604 (2011).
Valenti et al., The adsorption-desorption process of bovine serum albumin on carbon nanotubes, Journal of Colloid and Interface Science 307:349-356 (2007).
Humphrey et al., VMD: Visual Molecular Dynamics, Journal of Molecular Graphics, 14:33-38 (1996).
Wehmeyer et al., Dynamic Adsorption of Albumin on Nanostructured TiO2 Thin Films, Mater Sci Eng C Mater Biol Appl., 30:277-282 (2010).
Borkent et al., Superstability of Surface Nanobubbles, PRL, 98:204502(4) (2007).
Haynes et al., Structures and Stabilities of Adsorbed Proteins, Journal of Colloid and Interface Science, 169:313-328 (1995).
Guiseppi-Elie et al., Direct electron transfer of glucose oxidase on carbon nanotubes, Nanotechnology, 13:559-564 (2002).

(Continued)

Primary Examiner — Robert J Yamasaki
(74) Attorney, Agent, or Firm — Nevrivy Patent Law Group P.L.L.C.

(57) ABSTRACT

The present invention provides methods for adsorbing a protein onto a conductive solid substrate, comprising the application of an external potential to the solid substrate greater than +500 mV vs. the Ag/AgCl/Cl$^-_{SAT}$ reference electrode, in the presence of a solution comprising the protein, wherein the solution has a pH within ±2 units of the isoelectric point of the protein, and wherein the protein adsorbs to the conductive solid substrate upon application of the external potential. Some embodiments are directed to a process of protein adsorption on a solid surface mediated by an applied potential that can be affected significantly by altering a number of variables such as protein concentration, flexibility, charge, molecular weight, pH, and charge of substrate.

15 Claims, 26 Drawing Sheets

(56) References Cited

OTHER PUBLICATIONS

Permentier et al., Electrochemical Oxidation and Cleavage of Proteins with On-line Mass Spectrometric Detection: Development of an Instrumental Alternative to Enzymatic Protein Digestion, J Am Soc Mass Spectrom, 15:1707-1716 (2004).
Hampton et al., Nanobubbles and the nanobubble bridging capillary force, Advances in Colloid and Interface Science 154:30-55 (2010).
Norde, My voyage of discovery to proteins in flatland . . . and beyond, Colloids and Surfaces B: Biointerfaces, 61:1-9 (2008).
Norde, Proteins at Solid Surfaces, Wageningen University, p. 115-135.
Norde, Driving Forces for Protein Adsorption at Solid Surfaces, Macromol. Symp., 103:5-18 (1996).
Norde et al., Interfacial behaviour of proteins, with special reference to immunoglobulins. A physicochemical study, Advances in Colloid and Interface Science, 179-182:5-13 (2012).
Tyrrell et al., Images of Nanobubbles on Hydrophobic Surfaces and Their Interactions, Physical Review Letters, 87:176104(1-4) (2001).
Van Der Veen et al., Spreading of proteins and its effect on adsorption and desorption kinetics, Colloids and Surfaces B: Biointerfaces, 54:136-142 (2007).
Van Der Veen et al., Electrostatic interactions in protein adsorption probed by comparing lysozyme and succinylated lysozyme, Colloids and Surfaces B: Biointerfaces, 35:33-40 (2004).
Vermeer et al., CD Spectroscopy of Proteins Adsorbed at Flat Hydrophilic Quartz and Hydrophobic Teflon Surfaces, Journal of Colloid and Interface Science, 225:394-397 (2000).
Wang et al., Effect of Strong Electric Field on the Conformational Integrity of Insulin, Phys. Chem. A, 118:8942-8952 (2014).
Fujiwara, Spectroscopic ellipsometry: Principles and applications, West Sussex, England: J. Wiley & Sons (2007).
Abbas et al., Theoretical study of quadratic electro-optic effect in semiconducting zigzag carbon nanotubes, Phys. Rev. B, 76, 045403 (2007).
Armstrong et al., Direct electrochemical oxidation of Clostridium pasteurianum ferredoxin: Identification of facile electron-transfer processes relevant to cluster degradation, FEBS Letters, 150:214-218 (1982).
Bernabeu et al., Influence of surface charge on adsorption of fibrinogen and/or albumin on a rotating disc electrode of platinum and carbon, Biomaterials, 11:258-264 (1990).
Bian et al., An electrochemical biosensor for analysis of Fenton-mediated oxidative damage to BSA using poly-o-phenylenediamine as electroactive probe, Biosensors and Bioelectronics, 28:216-220 (2011).
Brusatori et al., Protein Adsorption Kinetics under an Applied Electric Field: An Optical Waveguide Lightmode Spectroscopy Study, Langmuir, 19:5089-5097 (2003).
Budi et al., Electric Field Effects on Insulin Chain-B Conformation, J. Phys. Chem B, 109:22641-22648 (2005).
Carter et al., Structure of serum albumin., Adv. Protein Chem., 45:153-203 (1994).
Chiku et al., Conformational Change Detection in Nonmetal Proteins by Direct Electrochemical Oxidation Using Diamond Electrodes, Anal. Chem., 80:5783-5787 (2008).
Chiku et al., Direct electrochemical oxidation of proteins at conductive diamond electrodes, J. Electroanal. Chem., 612:201-207 (2008).
Craig et al., Very small bubbles at surfaces—the nanobubble puzzle, Soft Matter, 7:40-48 (2011).
De Biase et al., Molecular Basis for the Electric Field Modulation of Cytochrome c Structure and Function, J. Am. Chem. Soc., 131:16248-16256 (2009).
Dolatshahi-Pirouz et al., Bovine serum albumin adsorption on nano-rough platinum surfaces studied by QCM-D, Colloids Surf. B, 66:53-59 (2008).

Edri et al., pH Effects On BSA-Dispersed Carbon Nanotubes Studied by Spectroscopy-Enhanced Composition Evaluation Techniques, Anal. Chem., 80:4049-4054 (2008).
Fraaije et al., Orientation of adsorbed cytochrome c as a function of the electrical potential of the interface studied by total internal reflection fluorescence, Biophys. J., 57:965-975 (1990).
Gao et al., Covalent Immobilization of Proteins on Carbon Nanotubes Using the Cross-Linker 1-Ethyl-3-(3-dimethylaminopropyl)carbodiimide—a Critical Assessment, Bioconjugate Chem., 19:1945-1950 (2008).
Giacomelli et al., The Adsorption-Desorption Cycle. Reversibility of the BSA-Silica System, J Colloid Interface Sci, 233:234-240 (2001).
Hermanson et al., Bioconjugate Techniques, Academic Press Inc., 2ed:1-1233 (2008).
Koutsioubas et al., Slow and remanent electric polarization of adsorbed BSA layer evidenced by neutron reflection, Soft Matter, 8:2638-2643 (2012).
Kranich et al., Direct Observation of the Gating Step in Protein Electron Transfer: Electric-Field-Controlled Protein Dynamics, J. Am. Chem. Soc., 130:9844-9848 (2008).
Molino et al., Fibronectin and Bovine Serum Albumin Adsorption and Conformational Dynamics on Inherently Conducting Polymers: A QCM-D Study, Langmuir, 28:8433-8445 (2012).
Mora et al., Determination of a setup correction function to obtain adsorption kinetic data at stagnation point now conditions, Journal of Colloid and Interface Science, 346:208-215 (2010).
Morrin et al., Characterisation of horseradish peroxidase immobilisation on an electrochemical biosensor by colorimetric and amperometric techniques, Biosensors and Bioelectronics, 18:715-720 (2003).
Morrow et al., Electric field effects on adsorption/desorption of proteins and colloidal particles on a gold film observed using surface plasmon resonance, Physica B, 394:203-207 (2007).
Nakabayashi et al., Electric field effects on fluorescence of the green fluorescent protein, Chem. Phys. Lett., 457:408-412 (2008).
Nejadnik et al., Staining proteins: A simple method to increase the sensitivity of ellipsometric measurements in adsorption studies, Colloids Surf. B, 82:253-257 (2011).
Nejadnik et al., Adsorption of Glucose Oxidase to 3-D Scaffolds of Carbon Nanotubes: Analytical Applications, Electroanalysis, 23:1462-1469 (2011).
Norde et al., BSA structural changes during homomolecular exchange between the adsorbed and the dissolved states, Journal of Biotechnology, 79:259-268 (2000).
Paleček et al., Potential-dependent surface denaturation of BSA in acid media, Analyst, 134:2076-2080 (2009).
Paleček et al., Ionic strength-dependent structural transition of proteins at electrode surfaces, Chem. Comm., 1685-1687 (2009).
Rabe et al., Understanding protein adsorption phenomena at solid surfaces, Adv. Colloid Interface Sci., 162:87-106 (2011).
Song et al., Surface electric field manipulation of the adsorption kinetics and biocatalytic properties of cytochrome c on a 3D macroporous An electrode, Anal. Bioanal. Chem., 390:333-341 (2008).
Squire et al., Hydrodynamic properties of bovine serum albumin monomer and dimer, Biochemistry, 7:4261-4272 (1968).
Toschi et al., Effects of Electric Field Stress on a β-Amyloid Peptide, J. Phys. Chem. B, 113:369-376 (2008).
Vacek et al., Electrochemical oxidation of proteins using ionic liquids as solubilizers, adsorption solvents and electrolytes, Electrochimica Acta, 126:31-36 (2014).
Vogler, Protein adsorption in three dimensions, Biomaterials, 33:1201-1237 (2012).
Wei et al., Electrocatalytic oxidation of tyrosines shows signal enhancement in label-free protein biosensors, Trends Anal. Chem., 39:130-148 (2012).
Wen et al., Refractive Index of Proteins in Aqueous Sodium Chloride, Anal. Biochem., 280:327-329 (2000).
Xie et al., Effects of external electric fields on lysozyme adsorption by molecular dynamics simulations, Biophys. Chem., 179:26-34 (2013).

(56) References Cited

OTHER PUBLICATIONS

Ying et al., Adsorption of human serum albumin onto gold: a combined electrochemical and ellipsometric study, J. Colloid Interface Sci, 279:95-99 (2004).

Zhang et al., molecular simulation of adsorption and its implications to protein chromatography: A review, Biochem Eng. J., 48:408-415 (2010).

Szucs et al., On the Adsorption of Glucose Oxidase at a Gold Electrode, J. Electrochem. Soc., 136:3748-3755 (1989).

Felder et al., A server and database for dipole moments of proteins, Nucleic Acids Research, 35:512-521 (2007).

Chumbimuni et al., Adsorption of proteins to thin-films of PDMS and its effect on the adhesion of human endothelial cells, RSC Advances, 1:706-714 (2011).

De Vos et al, Adsorption of the Protein Bovine Serum Albumin in a Planar Poly(acrylic acid) Brush Layer As Measured by Optical Reflectometry, Langmuir, 24:6575-6584 (2008).

Engelhardt et al., Protein Adsorption at the Electrified Air-Water Interface: Implications on Foam Stability, Langmuir, 28:7780-7787 (2012).

Ferrer et al., The Conformation of Serum Albumin in Solution: A Combined Phosphorescence Depolarization-Hydrodynamic Modeling Study, Biophysical Journal, 80:2422-2430 (2001).

Hecht et al., The 3D structure of glucose oxidase from Aspergillus niger. Implications for the use of GOD as a biosensor enzyme, Biosensors & Bioelectronics, 8:197-203 (1993).

Phillips et al., Scalable Molecular Dynamics with NAMD, J Comput Chem, 26:1781-1802 (2005).

Pazur et al., The Oxidation of Glucose and Related Compounds by Glucose Oxidase from Aspergillus niger, Biochemistry, 3:578-583 (1964).

Goran et al., Influence of Surface Adsorption on the Interfacial Electron Transfer of Flavin Adenine Dinucleotide and Glucose Oxidase at Carbon Nanotube and Nitrogen-Doped Carbon Nanotube Electrodes, Anal. Chem., 85:1571-1581 (2013).

\* cited by examiner

A.

B.

A.

B.

ADSORPTION OF PROTEINS ON CONDUCTING SURFACES UPON APPLICATION OF EXTERNAL POTENTIAL

CROSS REFERENCE TO RELATED APPLICATIONS

This application claims the benefit of U.S. application Ser. No. 61/892,819, filed Oct. 18, 2013. The content of the aforesaid application is relied upon and incorporated by reference in its entirety.

STATEMENT OF FEDERALLY SPONSORED RESEARCH AND DEVELOPMENT

This invention was made with government support under Grant No. 5SC3GM081085 awarded by the National Institute of Health. The government has certain rights in the invention.

BACKGROUND

The interaction of proteins with solid surfaces is a fundamental phenomenon with implications on nanotechnology, biomaterials and biotechnological processes. Although "most proteins interact with most surfaces," the particular strength, mechanism, and kinetics of each interaction have significant consequences in the final conformation of the adsorbed protein. Understanding the adsorption of proteins to solid surfaces is a critical topic in a variety of fields (biomedical, food science, sensing, etc.) because it can have significant consequences in the orientation, conformation, and biological activity of the adsorbed layer. (Norde, W., *Proteins at Solid Surfaces. Physical Chemistry of Biological Interfaces*. Marcel Dekker New York, 2000; Ying, P.; Viana, A. S.; Abrantes, L. M.; Jin, G., Adsorption of human serum albumin onto gold: a combined electrochemical and ellipsometric study. *J. Colloid Interface Sci.* 1004, 279, (1), 95-99).

Overall, the adsorption of proteins at interfaces is a spontaneous process that occurs almost every time a protein-containing solution contacts a solid surface. The adsorption is driven by short- and long-range forces resulting from a combination of electrostatic interactions between the protein and the sorbent surface, co-adsorption of small ions, dispersion forces, changes in the state of hydration of the sorbent surface and parts of the protein molecule, and structural rearrangements in the protein. (Norde, W., *Proteins at Solid Surfaces. Physical Chemistry of Biological Interfaces*. Marcel Dekker New York, 2000; Norde, W.; Giacomelli, C. E., BSA structured changes during homomolecular exchange between the adsorbed and the dissolved states. *J. Biotechnol.* 2000, 79, (3), 259-268; Vermeer, A. W. P., Norde, W., CD Spectroscopy of Proteins Adsorbed at Flat Hydrophilic Quartz and Hydrophobic Teflon Surfaces. *J. Colloid Interface Sci.* 2000, 225, (2), 394-397; Norde, W., My voyage of discovery to proteins in flatland . . . and beyond, *Colloids Surf. B* 2008, 61, (1), 1-9).

The adsorption is therefore influenced by the characteristics of the protein (size, flexibility, and charge), the substrate (surface energy, charge, and morphology) and the environment (solvent, Ph, temperature, and ionic strength). As a result, examples highlighting the effect on protein adsorption as a function of the characteristics of the protein, the chemical nature of the substrate or the conditions selected for the interaction abound in the literature. (Zhang, L.; Sun, Y., molecular simulation of adsorption and its implications to protein chromatography: A review *Biochem Eng. J.* 2010, 48, (3), 408-415; Rabe, M.; Verdes, D.; Seeger, S., Understanding protein adsorption phenomena at solid surfaces. *Adv. Colloid Interface Sci.* 2011, 162, (1-2), 87-106; Vogler, E. A., Protein adsorption in three dimensions. *Biomaterials* 2012, 33, (5), 1201-1237).

In most cases, it is evident that electrostatic interactions play a fundamental role in the adsorption and can affect the conformation, structure, and bioactivity of adsorbed proteins. (Palecek, E.; Ostatna, V., Ionic strength-dependent structural transition of proteins at electrode surfaces. *Chem. Comm.* 2009, (13), 1685-1687; Palecek, E.; Ostatna, V., Potential-dependent surface denaturation of BSA in acid media. *Analyst* 2009, 134, (10), 2076-2080). Besides chemical modifications performed on the protein and/or the substrate, electrostatic interactions can be controlled in situ by the application of an external potential to the sorbent surface. A handful of reports have explored this possibility. Brusatori et al. showed that the rate of albumin adsorption was increased under an electric field while the rate of cytochrome C adsorption remained unchanged. (Brusatori, M. A.; Tie, Y.; Van Tassel, P. R., Protein Adsorption Kinetics under an Applied Electric Field: An Optical Waveguide Lightmode Spectroscopy Study. *Langmuir* 2003, 19, (12), 5089-5097). Complementarily, it was demonstrated that the orientation, biocatalytic activity, and electron transfer kinetics of cytochrome C can be also altered by the presence of an electric field. (Fraaije, J. G.; Kleijn, J. M.; van der Graaf, M.; Dijt, J. C., Orientation of adsorbed cytochrome c as a function of the electrical potential of the interface studied by total internal reflection fluorescence. *Biophys. J.* 1990, 57, (5), 965-975; Song, Y.-Y.; Li, Y.; Yang, C.; Xia, X.-H., Surface electric field manipulation of the adsorption kinetics and biocatalytic properties of cytochrome c on a 3D macroporous An electrode. *Anal. Bioanal. Chem* 2008, 390, (1), 333-341; Kranich, A.; Ly, H. K.; Hildebrandt, P.; Murgida, D. H., Direct Observation of the Gating Step in Protein Electron Transfer: Electric-Field-Controlled Protein Dynamics, *J. Am. Chem. Soc.* 2008, 130, (30), 9844-9848; DeBiase, P. M.; Paggi, D. n. A.; Doctorovich, F.; Hildebrandt, P.; Estrin, D. A.; Murgida, D. H.; Marti, M. A., Molecular Basis for the Electric Field Modulation of Cytochrome c Structure and Function. *J. Am. Chem. Soc.* 2009, 131, (44), 16248-16256). Bernaben and Caprani found that the rate of adsorption and the area occupied by selected proteins (albumin and fibrinogen) can be affected by the surface charge on platinum and carbon electrodes. (Bernabeu, P.; Caprani, A., Influence of surface charge on adsorption of fibrinogen and/or albumin on a rotating disc electrode of platinum and carbon. *Biomaterials* 1990, 11, (4), 258-264). Later, Ying et al. reported that both positive and negative potentials promoted albumin adsorption to gold, probably due to the ability of the molecule to change its conformation on the surface. (Ying, P.; Viana, A. S.; Abrantes, L. M.; Jin, G., Adsorption of human serum albumin onto gold: a combined electrochemical and ellipsometric study. *J. Colloid Interface Sci.* 2004, 279, (1), 95-99). Moreover, Morrow et al. demonstrated that the adsorption of negatively-charged soybean peroxidase to gold can be controlled by an imposed electric field. (Morrow, R.; McKenzie, D. R.; Bilek, M. M. M.; MacDonald, C. L.; Stindt, M.; Anetsberger, G.; Martin, A. S., Electric field effects on adsorption/desorption of proteins and colloidal particles on a gold film observed using surface plasmon resonance. *Physica B* 2007, 394, (2), 203-207). Although the mechanism involved in this behavior was not described, they found that some proteins could be partially detached from the surface by applying a negative potential. Other properties of adsorbed peptides and proteins (such as insulin and green fluorescent protein) can be also modified by the presence of external potential. (Toschi, F.; Lugli, F.; Biscarini, F.; Zerbetto, F., Effects of Electric Field Stress on a β-Amyloid Peptide. *J. Phys. Chem. B* 2008, 113, (1), 369-376; Budi, A.; Legge, F. S.; Treutlein, H.; Yarovsky, I., Electric Field Effects on Insulin Chain-B Conformation, *J. Phys. Chem B* 2005, 109, (47), 22641-22648; Nakabayashi, T.; Kinjo, M.; Ohta, N., Electric field effects on fluorescence of the green fluorescent protein. *Chem. Phys. Lett.* 2008, 457, (4-6), 408-412).

Accordingly, there remains a need for improved methods for adsorbing proteins onto solid substrates, and improved substrates prepared according to such methods.

SUMMARY

It is to be understood that both the foregoing general description of the embodiments and the following detailed description are exemplary, and thus do not restrict the scope of the embodiments.

In one aspect, the invention provides a method for increasing the amount of adsorbed protein on a conductive solid substrate by application of an external potential. Some embodiments herein are directed to a method of protein adsorption on a solid substrate mediated by an applied potential that can be affected significantly by altering a number of variables such as protein concentration, flexibility, charge, molecular weight, pH, and the magnitude of the applied potential.

In another aspect, the invention provides a method for adsorbing a protein onto a conductive solid substrate, comprising the application of an external potential to the solid substrate greater than +500 mV vs. the $Ag/AgCl/Cl^-_{SAT}$ reference electrode, in the presence of a solution comprising the protein, wherein the solution has a pH within ±2 units of the isoelectric point of the protein, and wherein the protein adsorbs to the conductive solid substrate upon application of the external potential.

In some embodiments, the method comprises a primary adsorption process wherein the protein is adsorbed to the substrate to form an initial protein layer, followed by a secondary adsorption process wherein the applied external potential causes a polarization of the substrate and the initial layer of protein adsorbed to the substrate, wherein the polarized substrate and initial layer of protein adsorbed to the substrate induces a polarization of incoming protein, adsorption in the secondary adsorption.

In some embodiments, the primary adsorption comprises a step selected from the group consisting of
  i) adsorbing protein to the substrate at open circuit potential;
  ii) adsorbing protein to the substrate at one or more applied external potentials; and
  iii) combinations thereof.

In some embodiments, the applied external potential of part ii) is the same applied external potential that causes the secondary adsorption.

In another aspect, the invention provides a solid substrate adsorbed with protein prepared according to the methods of the invention.

In another aspect, the invention provides a device comprising a solid substrate prepared according to the methods of the invention. In some embodiments, the device is implantable in a subject. In some embodiments, the device is selected from the group consisting of a stent, pump, valve, drug delivery device, pins, rods, screws, and plates.

In another aspect, the invention provides a biosensor comprising a solid substrate prepared in accordance with the methods of the invention. In some embodiments, the solid substrate of the biosensor comprises an enzyme. In some embodiments, the biosensor is a glucose biosensor. In some embodiments, the enzyme is glucose oxidase. In some embodiments, the biosensor detects glucose in a sample and the glucose present in the sample is indicated by a color change.

In another aspect, the invention provides a diagnostic device comprising a solid substrate prepared in accordance with the methods of the invention. In some embodiments, the solid substrate comprises a protein antigen or an antigenic fragment thereof. In some embodiments, the solid substrate comprises an immunoglobulin or an antigen binding fragment thereof.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The skilled artisan will understand that the drawings, described below, are for illustration purposes only. The drawings are not intended to limit the scope of the present teachings in any way.

DETAILED DESCRIPTION

Figure 1:
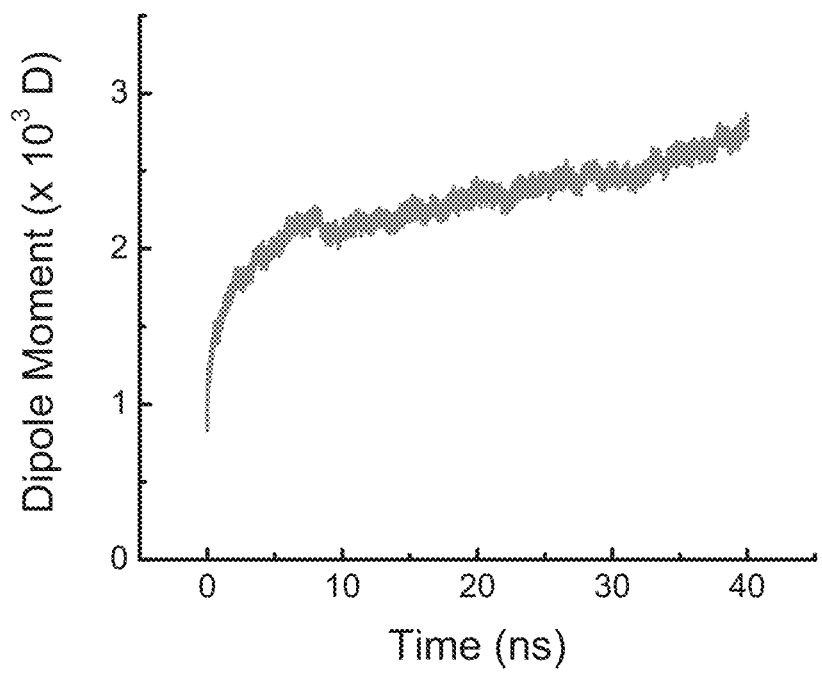
FIG. 1. (A) Simulation of the molecular dipole moment of GOx under the influence of an external electric field as a function of time. (B) Simulation of the structural changes in a GOx molecule under the influence of an external electric field as a function of time. Blue and red colors represent positive and negative electrostatic potentials, respectively.
Figure 1:
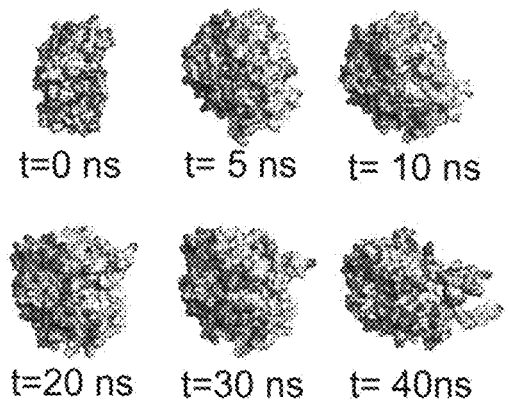

The present invention is based on the discovery of improved methods for the adsorption of proteins onto conductive solid substrates. The methods comprise the application of an external potential to the solid substrate in the presence of a solution comprising the protein.

Reference will not be made in detail to embodiments of the invention which, together with the drawings and the following examples, serve to explain the principles of the invention. These embodiments describe in sufficient detail to enable those skilled in the art to practice the invention, and it is understood that other embodiments may be utilized, and that structural, biological, and chemical changes may be made without departing from the spirit and scope of the present invention. Unless defined otherwise, all technical and scientific terms used herein have the same meanings as commonly understood by one of ordinary skill in the art.

One skilled in the art may refer to general reference texts for detailed descriptions of known techniques discussed herein or equivalent techniques. These texts include *Current Protocols in Molecular Biology* (Ausubel et. al., eds. John Wiley & Sons, N.Y. and supplements thereto), *Current Protocols in Immunology* (Coligan et al., eds., John Wiley St Sons, N.Y. and supplements thereto), *Current Protocols in Pharmacology* (Enna et al., eds. John Wiley & Sons, N.Y. and supplements thereto) and *Remington: The Science and Practice of Pharmacy* (Lippincott Williams & Wilicins, 2Vt edition (2005)), for example.

Definitions of common terms in molecular biology may be found, for example, in Benjamin Lewin, Genes VII, published by Oxford University Press, 2000 (ISBN 019879276X); Kendrew et al. (eds.); *The Encyclopedia of Molecular Biology*, published by Blackwell Publishers, 1994 (ISBN 0632021829); and Robert A. Meyers (ed.), *Molecular Biology and biotechnology: a Comprehensive Desk Reference*, published by Wiley, John & Sons, Inc., 1995 (ISBN 0471186341).

For the purpose of interpreting this specification, the following definitions will apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in the document where the term is originally used). The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." As used in this specification and claim(s), the words "comprising" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. Furthermore, where the description of one or more embodiments uses the term "comprising," those skilled in the art would understand that, in some specific instances, the embodiment or embodiments can be alternatively described using the language "consisting essentially of" and/or "consisting of." As used herein, the term "about" means at most plus or minus 10% of the numerical value of the number with which it is being used.

In some embodiments, the methods comprise coating a conductive solid substrate with an initial first layer of protein, which can be at open circuit potential (no external applied potential), at some applied external potential, or a combination thereof, by contacting the solid substrate with a solution comprising the protein, resulting in adsorption of the protein to the solid substrate.

In some embodiments, a secondary protein layer is adsorbed to the substrate upon application of an external applied potential. In some embodiments, the external applied potential is at least +500 mV vs. the $Ag/AgCl/Cl^-_{SAT}$ reference electrode. In some embodiments, the secondary protein layer is adsorbed by contacting the solid substrate coated with an initial first layer with a solution comprising the protein. In some embodiments, the protein in solution has close to or substantially no net charge. In some embodiments, the solution comprising the protein for adsorption in the secondary protein layer has a pH within ±2 units of the isoelectric point (IEP) of the protein.

In some embodiments, upon application of the external applied potential, the secondary layer can grow and preserve the function of the protein. In some embodiments, the rate at which the secondary layer grows can depend on the pH (generally faster at the IEP), the potential applied (faster at higher potentials), the concentration of protein (faster at higher concentrations), and the ionic strength (faster at lower ionic strengths). In some embodiments, if the potential applied is too high, the protein can be oxidized and loose its function. Without being bound by theory as to how the invention works, in some embodiments, it is believed that the applied external potential causes a polarization of the solid substrate that is coated with an initial layer of protein adsorbed to the solid substrate, wherein the polarized solid substrate and adsorbed initial layer of protein induces a polarization of incoming protein, resulting in adsorption of the incoming protein. Solid surfaces prepared according to the methods in some embodiments of the invention can achieve protein layers having a very high thickness, while maintaining sufficient biological activity.

The pH of the solution comprising the protein used to adsorb a first initial layer of protein on the solid substrate is not limiting, and can include solutions having low, neutral and high pH values.

In some embodiments, the pH of the solution comprising the protein used to adsorb the secondary layer of protein on the solid substrate is generally within ±2 units of the isoelectric point of the protein. In some embodiments, the pH of the solution results in a protein having close to or substantially no net charge.

The pH of the solution can be adjusted using acids/bases as appropriate. The pH of the solution can be measured using standard laboratory analytical techniques. In some embodiments, the pH can be measured using a glass electrode and a digital pH meter (Orion 420A+, Thermo; Waltham, MA).

In some embodiments, the pH of the solution used to adsorb the first initial layer of proteins is about the same as the pH of the solution used to adsorb the secondary protein layer. In some embodiments, the pH of the solution results in the protein having a net negative charge. In some embodiments, the pH of the solution results in a protein having close to or substantially no net charge.

In some embodiments, the pH of the solution is within ±2 units of the isoelectric point of the protein. The isoelectric point of a protein is the pH at which the protein has no net charge. At pH values lower than the isoelectric point, more basic side chains of amino acids become protonated to give the protein a net positive charge. Similarly, at pH values higher than the isoelectric point, more acidic side chains become deprotonated, giving the protein a net negative charge. It should be noted that the protein can still contain charged side chains at its isoelectric point; however, at the isoelectric point, the number of positively-charged side chains is equal to the number of negatively-charged side chains.

In some embodiments, the pH of the solution can range from 1-14. In some embodiments, the pH of the solution is selected from the group consisting of within ±2.0 units of the isoelectric point, within ±1.5 units of the isoelectric point, within ±1 unit of the isoelectric point, within ±0.9 units of the isoelectric point, within ±0.8 units of the isoelectric point, within ±0.7 units of the isoelectric point, within ±0.6 units of the isoelectric point, within ±0.5 units of the isoelectric point, within ±0.4 units of the isoelectric point, within ±0.3 units of the isoelectric point, within ±0.2 units of the isoelectric point, within ±0.1 units of the isoelectric point, and within ±0.0 units of the isoelectric point.

In some embodiments, the pH of the protein solution can be 3.7, 4.2, 4.7, 5.2, 5.7, 6.2, 6.7, or 7.2. The pH of the protein solution may also be in the range of 3-8. In some embodiments, the pH of the protein solution is 4.7. In some embodiments, the pH will be approximately equal to physiological conditions (about pH 7.3).

In some embodiments, the method comprises adsorbing a protein onto a conductive solid substrate, comprising the application of an external potential to the solid substrate greater than +500 mV in the presence of a solution comprising the protein, wherein the solution has a pH within ±2 units of the isoelectric point of the protein, and wherein the protein adsorbs to the conductive solid substrate upon application of the external potential.

The solid substrate which the protein can be adsorbed to is not limiting, provided it is conductive. In some embodiments, the solid substrate is relatively inert. In some embodiments, the solid substrate has a smooth surface characteristic, which can enable the accurate measurement of the thickness of the applied protein layer. In some embodiments, the conductive solid substrate is a conductive substrate, with non-metallic characteristics.

In some embodiments, the conductive solid substrate comprises a material selected from the group consisting of nanostructured carbon, optically transparent carbon electrodes (OTCE), silica wafers coated with thin optically transparent carbon films ($Si/SiO_2/OTCE$), graphene, carbon nanotubes, graphite, carbon based surface made from pyrolyzed paper, Cu-modified carbon made from pyrolyzed paper, metallic surface (gold, platinum, etc.), conductive oxides (such as indium tin oxide), and a substrate prepared by coating or mixing any of the aforementioned materials. In some embodiments, the optically transparent carbon electrodes can be prepared by pyrolysis of AZ P4330-RS Photoresist purchased from AZ Electronic Materials USA Corp. (Somerville, NJ).

In some embodiments, the solid substrate is biocompatible. In some embodiments, the solid substrate is an implant or a part thereof. In some embodiments, the solid substrate is permeable or semi-permeable to liquids, gasses, and/or cells. In some embodiments, the solid substrate is permeable or semi-permeable to oxygen.

In some embodiments, the carbon-based surface made from paper is made by pyrolysis of a selected paper substrate under reductive conditions and at high temperatures. The type or dimensions of the selected paper are not limiting. In some embodiments the reductive conditions can be given by the addition of $H_2$ to the reaction change for the pyrolysis. In some embodiments, the concentration of $H_2$ is 5%. In some embodiments the temperature for the pyrolysis step can be above 400° C. In some embodiments the temperature can be 1000° C.

In some embodiments, the paper can be modified by the addition of organic and/or inorganic materials before the pyrolysis step. The type or concentration of the material added to the paper before pyrolysis are not limiting. In some embodiments, the addition of organic materials leads to carbon-based substrates with improved performance. In some embodiments, the addition of compounds containing metallic elements or the corresponding cations leads to the formation of carbon-based substrates containing metallic particles after the pyrolysis process. In some embodiments, the selected compound is $CuSO_4$, $AgNO_3$, $NiSO_4$, or $HAuCl_4$.

In some embodiments, the Cu-modified carbon was made from paper by pyrolysis of a selected paper substrate upon the addition of $CuSO_4$ to the paper, under reductive conditions and at high temperatures. In some embodiments the reductive conditions can be given by the addition of $H_2$ to the reaction chamber for the pyrolysis. In some embodiments, the concentration of $H_2$ is 5%. In some embodiments the temperature for the pyrolysis step can be above 400° C. In some embodiments the temperature can be 1000° C.

The external applied potential is not limiting. In some embodiments, the applied potential is in a range selected from the group consisting of +440 to +1500 mV, +600 to +1250 mV, +600 to +1000 mV, +600 to +900 mV, and +700 to +850 mV vs. the $Ag/AgCl/Cl^-_{SAT}$ reference electrode. In some embodiments, the applied potential is selected from the group consisting of about +550 mV, about +600 mV, about +650 mV, about +700 mV, about +750 mV, about +800 mV, about +850 mV, about +900 mV and about +950 mV vs. the $Ag/AgCl/Cl^-_{SAT}$ reference electrode. In some embodiments, the applied potential is about +850 mV vs. the $Ag/AgCl/Cl^-_{SAT}$ reference electrode. In some embodiments potentials of +500 mV, +650 mV, +800 mV, +900 mV, or any potential in the range of +500 mV-900 mV vs. the $Ag/AgCl/Cl^-_{SAT}$ reference electrode are applied. In one embodiment a potential of 800 mV vs. the $Ag/AgCl/Cl^-_{SAT}$ reference electrode is applied. In some embodiments, the optimal range of positive potentials will depend on the attributes of the protein being adsorbed, therefore the invention is not limited by the ranges disclosed, but can be any potential value, dependent on the nature of the protein in question.

The duration that the substrate can be contacted with the protein solution at open circuit potential or an applied external potential to form an initial protein layer is not limiting. In some embodiments, the initial protein layer is applied from 1-60 minutes upon application of an external potential or at open circuit potential. In some embodiments, the initial protein layer is applied in 1-5 minutes, 1-10 minutes, 5-15 minutes, 5-20 minutes, 5-30 minutes, 10-30 minutes, 15-40 minutes, and 20-60 minutes.

The duration that the external potential can be applied to form a secondary layer is not limiting. In some embodiments, the potential is applied for a period of time selected from the group consisting of 1-10 minutes, 1-30 minutes, 1-3 hours, 3-6 hours, 6-10 hours, 10-15 hours, 15-20 hours, 20-30 hours, 30-40 hours, 40-50 hours, 50-60 hours, 60-70 hours, 70-80 hours, 80-90 hours, and 90-100 hours.

The concentration of the protein in solution is not limiting, and in some embodiments can be any concentration up to the solubility of the protein in the solution. In some embodiments the concentration of the protein solution can be 1.0, 0.5, 0.1, 0.05, or 0.01 mg/mL. In one embodiment the concentration of the protein in solution is 0.5 mg/mL. In some embodiments, the concentration of the protein solution may be in the range of 0.01-10 mg/mL. In some embodiments, the protein concentration in the solution is selected from the group consisting of at least 0.001 mg/L, at least 0.01 mg/L, at least 0.1 mg/mL, at least 0.5 mg/mL, at least 1 mg/mL, at least 2 mg/mL, at least 5 mg/mL, at least 10 mg/mL, at least 25 mg/mL, at least 50 mg/mL, at least 100 mg/mL, and the concentration corresponding to the solubility of the protein in solution.

The concentration of the protein adsorbed to the solid substrate is not limiting. In some embodiments, the concentration of protein adsorbed on the substrate is at least 0.1 mg/m$^2$. In some embodiments, the concentration of protein adsorbed on the substrate is selected from the group consisting of 0.1-0.5 mg/m$^2$, 0.5-1.0 mg/m$^2$, 1-3 mg/m$^2$, 3-5 mg/m$^2$, 5-10 mg/m$^2$, 10-15 mg/m$^2$, 15-20 mg/m$^2$, and greater than 20 mg/m$^2$.

In some embodiments, the protein solution is buffered. In some embodiments, the buffer is selected to maintain the pH within a narrow pH range. In some embodiments, the narrow pH range is for ensuring the biological activity of the protein. In some embodiments, the solution is maintained in a narrow pH range to be within a certain number of units of the isoelectric point of the protein or at the isoelectric point. In some embodiments, the buffer has a buffering capacity at or around the isoelectric point of the protein in solution. In some embodiments, the buffer may be a citrate buffer, a phosphate buffer, acetate buffer, tris buffer, HEPES buffer or any other buffer known to the chemical arts, and combinations thereof. In some embodiments, the buffer is 10 mmol·L$^{-1}$ citrate buffer.

In some embodiments, the solution is provided to the substrate and is periodically removed and replenished with additional solution. In some embodiments, the solution is not removed, but is periodically boosted with protein either in stock solution or solid form. In some embodiments, the solution is provided to the substrate at a flow rate selected from the group consisting of 0 mL/min, at least about 0.5 mL/min, at least about 1 mL/min, at least about 2 mL/min, at least about 4 mL/min, at least about 10 mL/min, at least about 50 mL/min, at least about 100 mL/min, at least about 500 mL/min, and at least about 1 liter/min. In some embodiments, the solution is not removed and/or replenished.

The ionic strength of the solution comprising the protein is not limiting. In some embodiments, when the protein exhibits close to no net charge or no net charge, the ionic strength is less than 50 mM. In some embodiments, the ionic strength of the solution is selected from the group consisting of less than 50 mM, less than 40 mM, less than 30 mM, less than 20 mM, less than 10 mM, less than 5 mM, less than 4 mM, less than 3 mM, less than 2 mM, less than 1 mM, less than 0.5 mM, less than 0.1 mM and 0.0 mM. In some embodiments the protein solution has a range of ionic strength. In some embodiments, the ionic strength ranges from 0-100 mM. In one embodiment the solution contains about 25 mM NaCl.

The protein that can be adsorbed to the conductive solid substrate is not limiting. In some embodiments, the protein is selected from the group consisting of an enzyme, a cellular matrix protein, a messenger protein, an antigenic protein, and a protein with any other biological activity and fragments and combinations thereof.

In some embodiments, the protein is an enzyme. In some embodiments the protein is glucose oxidase. In some embodiments, the method further comprises assaying the adsorbed enzyme for catalytic activity. In some embodiments, the protein is a cellular matrix protein or combinations of cellular matrix proteins. In some embodiments, the protein is albumin. In some embodiments, the protein is bovine serum albumin (BSA).

In some embodiments, the protein is a cellular matrix protein selected form the group consisting of collagen (e.g., any of types I-XXVIII), fibronectin, elastin, laminin and combinations thereof. In some embodiments, the protein is type I collagen.

In some embodiments, the protein has a sequence of mammalian origin. In some embodiments, the protein has a sequence of human origin.

In some embodiments, the adsorption of the protein can be assayed in real time using an ellipsometer coupled to a potentiostat. In some embodiments, the substrate is both optically transparent and a conducting material.

The rate of adsorption to the substrate is not limiting. In some embodiments, the initial rate of protein adsorption to the substrate ranges from $2\times10^{-3}$ mg m$^{-2}$ min$^{-1}$ to $50\times10^{-3}$ mg m$^{-2}$ min$^{-1}$ within 30 minutes of application of the external potential. In some embodiments, the rate of protein adsorption to the substrate ranges from $0.5\times10^{-3}$ mg m$^{-2}$ min$^{-1}$ to $10\times10^{-3}$ mg m$^{-2}$ min$^{-1}$ between 150 and 180 minutes after start of the application of the external potential.

In some embodiments, the method comprise a primary adsorption process wherein the protein is adsorbed to the substrate to form an initial protein layer, followed by a secondary adsorption process wherein the applied external potential causes a polarization of the substrate and the initial layer of protein adsorbed to the substrate, wherein the polarized substrate and initial layer of protein adsorbed to the substrate induces a polarization of incoming protein, resulting in adsorption of the incoming protein.

In some embodiments, the rate of protein adsorption in the primary adsorption is greater than the rate of protein adsorption in the secondary adsorption.

In some embodiments, the primary adsorption comprises a step selected from the group consisting of
i) adsorbing protein to the substrate at open circuit potential;
ii) adsorbing protein to the substrate at one or more applied external potentials; and
iii) combinations thereof.

In some embodiments, the applied external potential of part ii) is the same applied external potential that causes the secondary adsorption.

The thickness of the initial layer is not limiting. In some embodiments, the thickness of the initial protein layer on the substrate ranges from about 0.75 to about 2 nm, and the thickness of the protein layer following the secondary adsorption is in a range selected from the group consisting of between 2-20 nm, between 3-15 nm, between 3-10 nm and between 4-8 nm.

In some embodiments, the total thickness of the protein layer on the substrate ranges from about 2 to about 25 nm, from about 2 to about 10 nm, and from about 3 to about 6 nm.

In some embodiments, the method comprises incubating cells with the protein adsorbed to the substrate, wherein the cells adhere to the protein adsorbed on the substrate.

In some embodiments, the cells are human cells. In some embodiments, the cells are stem cells. In some embodiments, the stem cells are selected from the group consisting of pluripotent stem cells, multipotent stem cells, totipotent stem cells, embryonic stem cells, induced pluripotent (iPS) stem cells, adult stem cells, and organ specific stem cells. In some embodiments, the cells are differentiated cells and/or progenitor cells. In some embodiments, the differentiated cells and/or progenitor cells are derived from stem cells in vitro or in vivo. In some embodiments, the stem cells are human mesenchymal stem cells. In some embodiments, the cells are incubated with the substrate in vitro. In some embodiments, the cells are incubated with the substrate in vivo.

In some embodiments, the cells express and secrete one or more bioactive molecules of interest, such as growth factors, cytokines, insulin, hormones, peptides, and the like. In some embodiments, the cells are engineered to express and secrete a bioactive molecule of interest. In some embodiments, the bioactive molecule provides a therapeutic effect or benefit.

The possible uses and applications of the solid substrate coated with protein are not limiting. In some embodiments, the solid substrate can be useful in a medical device. In some embodiments, the medical device is implantable. The implantable device is not limiting and can include stents, pumps, valves, drug delivery devices, pins, rods, screws, and plates. In some embodiments, the solid substrate can be useful in a biosensor. In some embodiments, the biosensor is a glucose biosensor. In some embodiments, the biosensor detects glucose in a sample and the glucose present in the sample is indicated by a color change. In some embodiments, the solid substrate can be useful in a diagnostic device or assay. In some embodiments the protein used in the diagnostic device or assay is an antigenic protein or fragment thereof. In some embodiments, the protein used in the diagnostic assay is an immunoglobulin or antigen binding fragment thereof. An antibody fragment contains at least one antigen binding fragment and can include (Fab) fragments, F(ab')2 fragments and single chain variable fragments (scFv).

While the invention has been described with reference to certain particular examples and embodiments herein, those skilled in the art will appreciate that various examples and embodiments can be combined for the purpose of complying with all relevant patent laws (e.g., methods described in specific examples can be used to describe particular aspects of the invention and its operation even though such are not explicitly set forth in reference thereto).

Other embodiments of the invention are discussed throughout this application. Any embodiment discussed with respect to one aspect applies to other aspects as well and vice versa. Each embodiment described herein is understood to be embodiments that are applicable to all aspects of the invention. It is contemplated that any embodiment discussed herein can be implemented with respect to any device, method, or composition, and vice versa. Furthermore, systems, compositions, and kits of the invention can be used to achieve methods of the invention.

Aspects of the present teachings may be further understood in light of the following examples, which should not be construed as limiting the scope of the present teachings in any way.

Example 1

Potential-Assisted Adsorption of Bovine Serum Albumin onto Optically Transparent Carbon Electrodes This Example describes the effect of the applied potential on the adsorption of bovine serum albumin (BSA) to optically transparent carbon electrodes (OTCE). BSA was selected because it represents a model soft protein, which is prone to adsorption to a variety of surfaces under a wide range of experimental conditions. OTCE were selected as a sorbent surface because they are transparent, conductive, and feature a wide operational window without the formation of oxides. (Alharthi, S. A.; Benavidez, T. E; Garcia, C. D., Ultrathin Optically Transparent Carbon Electrodes Produced from Layers of Adsorbed Proteins. *Langmuir* 2013, 29, (10), 3320-3327; Benavidez, T, E.; Garcia, C. D., Spectroscopic and electrochemical characterization of nanostructured optically transparent carbon electrodes. *Electrophoresis* 2013, n/a-n/a.) Adsorption experiments were performed under stagnation point flow conditions (Mora, M. F.; Reza Nejadnik, M.; Baylon-Cardiel, J. L.; Giacomelli, C. E.; Garcia, C. D., Determination of a setup correction function to obtain adsorption kinetic data at stagnation point now conditions. *J. Colloid Interface Sci.* 2010,346, (1), 208-215) and followed (in real time) by spectroscopic ellipsometry as a function of potential applied, solution pH, ionic strength, and protein concentration.

To decouple the effect of the applied potential from the high affinity of the protein for the bare surface, the surface of the OTCE was initially saturated with a layer of BSA. Experiments described in the Example show that potential values higher than +500 mV induced a secondary adsorption process (not observed at open-circuit potentials), yielding significant changes in the thickness (and adsorbed amount) of the BSA layer obtained. Although the process showed a significant dependence on the experimental conditions selected, the application of higher potentials, selection of pH values around the isoelectric point (IEP) of the protein, high concentrations of protein, and low ionic strengths yielded faster kinetics and the accumulation of larger amounts of protein on the substrate. These experiments, obtained around the IEP of the protein, contrast with the traditional hypothesis that enhanced electrostatic interactions between the polarized substrate and the (oppositely charged) protein are solely responsible for the enhanced adsorption. These results suggest that the potential applied to the electrode is able to polarize the adsorbed layer and induce dipole-dipole interactions between the adsorbed and the incoming protein. This mechanism could be responsible for the potential-dependent oversaturation of the surface and could bolster to the development of surfaces with enhanced catalytic activity and implants with improved biocompatibility.

1. Experimental Design

Reagents and Solutions.

All aqueous solutions were prepared using 18 MΩ·cm Water (NANOpure Diamond, Barnstead; Dubuque, IA) and analytical-grade reagents. Citric acid was purchased from Aldrich Chemical Company (Milwaukee, WI). Brilliant Blue G was obtained from Sigma-Aldrich (St. Louis, MO). BSA, NaOH, and anhydrous $NaH_2PO_4$ were purchased from Fisher Scientific (Fair Lawn, NJ). Citrate buffer was prepared by dissolving 1.9212 g of citric acid in ultrapure water to obtain 1 L of 10 mmol·$L^{-1}$ citric acid. To avoid changing its analytical concentration, the pH of the buffer was adjusted adding 1 mol·$L^{-1}$ NaOH dissolved in 10 mol·$L^{-1}$ citrate solution and measured using a glass electrode and a digital pH meter (Orion 420A+, Thermo; Waltham, MA). Stock solutions of BSA (1.00, 0.50, 0.10, 0.05 and 0.01 mg·$mL^{-1}$) were prepared by dissolving a known amount of protein in a 10 mmol·$L^{-1}$ buffer solution.

Substrates.

All experiments were performed using OTCE substrates, prepared following a previously described procedure. (Benavidez, T. E.; Garcia, C. D., Spectroscopic and electrochemical characterization of nanostructured optically transparent carbon electrodes. *Electrophoresis* 2013, n/a-n/a.)

Details regarding the optical and electrochemical characterization of such films are also included in that publication. Briefly, a standard <111> silicon wafer (Si/SiO$_2$, Sumco; Phoenix, AZ) was first scored using a computer-controlled engraver (Gravograph IS400, Gravotech; Duluth, GA), defining pieces of 1 cm in width and 3 cm in length that were then manually cut and cleaned in piranha solution (30% hydrogen peroxide and 70% sulfuric acid) at 90° C. for 30 min. After thorough rinsing with water, the substrates were immersed and stored in ultrapure water until use. Then, the wafers were coated with a layer of photoresist (AZ P4330-RS, AZ Electronic Materials; Somerville, NJ) using a spin coater (Laurell, WS-400-6NPP; North Wales, PA). In order to control the thickness of the OTCE, the photoresist was diluted to 60% v/v with propylene glycol monomethyl ether acetate (PGMEA 99%, Alfa Aesar; Ward Hill, MA). Next, the photoresist-coated substrates were heated at 110° C. for 60 s in a convection oven to evaporate the solvent and then transferred to a tube furnace (Thermolyne F21135, Barnstead International; Dubuque, IA) for pyrolysis. The carbonization step began by flushing the system at 1 L·min$^{-1}$ with forming gas (95% Ar+5% H$_2$, v/v) for 5 min. Next, the temperature was increased to 1000° C. using a 20° C.·min$^{-1}$ ramp. After 1 h, the system was allowed to cool down to room temperature in the presence of the forming gas. Finally, the samples were stored in a petri dish for a minimum of 3 days to complete the spontaneous surface oxidation.

Spectroscopic Ellipsometry.

Adsorption experiments were performed using a variable angle spectroscopic ellipsometer (WVASE, J. A. Woollam Co.; Lincoln, NE) following a procedure described elsewhere. (Mora, M. F.; Reza Nejadnik, M.; Baylon-Cardiel, J. L.; Giacomelli, C. E.; Garcia, C. D., Determination of a setup correction function to obtain adsorption kinetic data at stagnation point flow conditions. *J. Colloid Interface Sci.* 2010, 346, (1), 208-215; Nejadnik, M. R.; Francis, L.; Garcia, C. D., Nanoscale Scaffolds of Carbon Nanotubes for Immobilization of Glucose Oxidase. *Electroanalysis* 2011, 23, (6), 1462-1469.) Spectroscopic Ellipsometry (SE) has proven suitable to study adsorption of proteins in real time and provides useful information about the thickness, optical constants, and structure of the adsorbed film. More information regarding the principle of SE can be found elsewhere. (Fujiwara, H., *Spectroscopic ellipsometry. Principles and applications.* J. Wiley & Sons: West Sussex, England, 2007.) The mean square error (MSE, calculated by a built-in function in WVASE) was used to quantify the difference between the experimental and model-generated data. In agreement with previous reports (Mora, M. F.; Reza Nejadnik, M.; Baylon-Cardiel, J. L.; Giacomelli, C. E.; Garcia, C. D., Determination of a setup correction function to obtain adsorption kinetic data at stagnation point flow conditions. *J. Colloid Interface Sci.* 2010,346, (1), 208-215; Nejadnik, M. R.; Francis, L.; Garcia, C. D., Nanoscale Scaffolds of Carbon Nanotubes for Immobilization of Glucose Oxidase. *Electroanalysis* 2011, 23, (6), 1462-1469), MSE<15 were considered acceptable.

Dynamic adsorption experiments were performed in a modified electrochemical cell (Mora, M. F.; Reza Nejadnik, M.; Baylon-Cardiel, J. L.; Giacomelli, C. E.; Garcia, C. D., Determination of a setup correction function to obtain adsorption kinetic data at stagnation point flow conditions. *J. Colloid Interface Sci.* 2010, 346, (1), 208-215) (J. A. Woollam Co.; Lincoln, NE) mounted directly on the vertical base of the ellipsometer, with an incident angle of 70° C. Before the BSA adsorption experiments, the thickness of the thin optically transparent carbon film was measured by placing the substrate in the ellipsometry cell and performing a spectroscopic scan from 300 to 1000 nm (with 10 nm steps) using 10 mmol·L$^{-1}$ buffer solution as the ambient medium. Unless otherwise stated, a layer of protein was first adsorbed at open circuit potential (OCP, the potential at which no current flows through the cell) as follows. The dynamic experiment was started by pumping buffer to the surface of the OTCE at a rate of 1 mL·min$^{-1}$ to establish the baseline. After 20 min, the BSA solution was pumped to the surface and the adsorption began. An initial fast adsorption process, followed by a slower one, was always observed. After a plateau in the signal was observed, the selected potential (+500, +650, +800 or +950 mV) was applied while the ellipsometric angles were monitored over time. As the two consecutive adsorption experiments were performed with the same protein, no washing steps were implemented. The applied potentials were selected taking into account the window potential of OTCE, which spans between −0.4 V and 1.0 V. The potential was applied using a CHI812B Electrochemical Analyzer (CH Instrument, Inc.; Austin, TX), a Ag|AgCl|KCl$_{sat}$ reference electrode and a platinum wire as the counter electrode, mounted on the cell using ad hoc supports. This experimental procedure provided the data to calculate the thickness of the OTCE, the adsorbed amount of BSA, and the adsorption rate. In order to verify the thickness of the adsorbed layer of BSA, Brilliant Blue was added to the cell and the measurement repeated. (Nejadnik, M. R.; Garcia, C. D., Staining proteins: A simple method to increase the sensitivity of ellipsometric measurements in adsorption studies, *Colloids Surf. B* 2011, 82, (1), 253-257.) This procedure changes the optical properties of the adsorbed protein layer, which can be represented using a simple optical model (Lorentz), increasing the sensitivity of the detection. The experimental data was used to determine the thickness (d, expressed in nm) of the adsorbed layer. Then the adsorbed amount (Γ, expressed in mg·m$^{-2}$) was calculated using the following, $$\Gamma = \frac{d(n - n_0)}{(dn/dc)}$$

where n and n$_o$ are the refractive index of the protein and of the ambient (aqueous buffer), respectively. In accordance with previous reports (Nejadnik, M. R.; Francis, L.; Garcia, C. D., Nanoscale Scaffolds of Carbon Nanotubes for Immobilization of Glucose Oxidase. *Electroanalysis* 2011, 23, (6), 1462-1469; Wen, J.; Arakawa, T., Refractive Index of Proteins in Aqueous Sodium Chloride. *Anal. Biochem.* 2000, 280, (2), 327-329), the refractive index increment for the proteins in the adsorbed layer (dn/dc) was assumed to be 0.187 mL·g$^{-1}$. BSA was considered as a model system to begin the study of protein adsorption to the substrates (OTCE). Thus, the physicochemical characteristics of this globular protein, such as molecular weight (66.5 kDa) (Squire, P. G.; Moser, P.; O'Konski, C. T., Hydrodynamic properties of bovine serum albumin monomer and dimer. *Biochem.* 1968, 7, (12), 4261-4272), isoelectric point (IEP=4.7) (Carter, D. C; Ho, J. X., Structure of serum albumin. *Adv. Protein Chem.* 1994, 45, 153-203), dimensions (4 nm×4 nm×14 nm) (Squire, P. G.; Moser, P.; O'Konski, C. T., Hydrodynamic properties of bovine serum albumin monomer and dimer. *Biochem.* 1968, 7, (12), 4261-4272), and glass transition temperature (defining it as a soft protein) (Nonie, W.; Giacomelli, C. E., BSA structural changes during homomolecular exchange between the adsorbed and the dissolved states. *J. Biotechnol.* 2000, 79, (3), 259-268) were taken into account to analyze the experimental results.

Atomic Force Microscopy (AFM).

AFM was used to confirm the topography of the OTCE. Experiments were performed using a Veeco diMultimode Nanoscope V scanning probe microscope (Plainview, NY) operating in tapping and non-contact mode.

2. Results

Development of the Optical Model.

Figure 8:
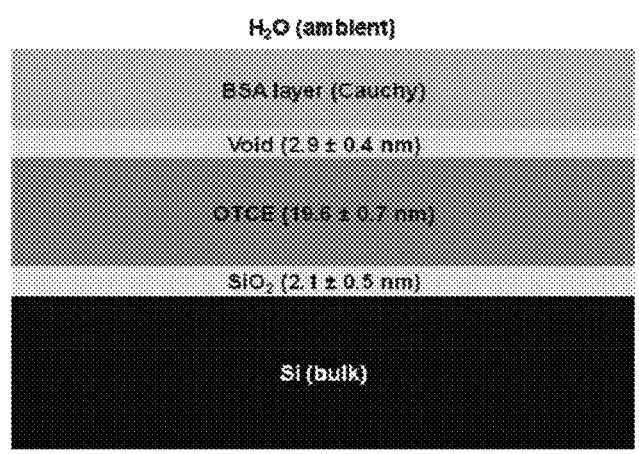
FIG. 8. (A) Ellipsometric model used to interpret the optical behavior of adsorbed protein layer. (B) AFM micrograph of the surface of the OTCE used as substrate for adsorption experiments of BSA.
Figure 8:
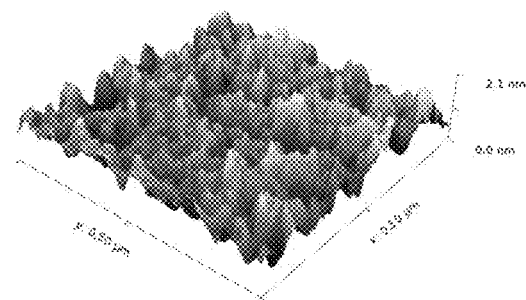

The interpretation of ellipsometric measurements typically requires an optical model that describes the substrate microstructure in terms of the refractive index (n), extinction coefficient (k), and thickness (d). Accordingly, a previously reported optical model (Alharthi, S. A.; Benavidez, T. E.; Garcia, C. D., Ultrathin Optically Transparent Carbon Electrodes Produced from Layers of Adsorbed Proteins. *Langmuir* 2013, 29, (10), 3320-3327; Benavidez, E. E.; Garcia, C. D., Spectroscopic and electrochemical characterization of nanostructured optically transparent carbon electrodes. *Electrophoresis* 2013, n/a-n/a) was refined to include five uniaxial layers with optical axes parallel to the substrate surface (shown in FIG. 8A).

In all cases, the ambient was represented using the optical properties of water. First, the silica wafer was described using the dielectric functions of Si (bulk, d=1 mm) and $SiO_2$ (d=2.1±0.5 nm). Then, the OTCE (d=19.6±0.7 nm) was described using the optical constants obtained experimentally in our lab and presented in a previous paper. (Benavidez, T. E.; Garcia, C. D., Spectroscopic and electrochemical characterization of nanostructured optically transparent carbon electrodes. *Electrophoresis* 2013, n/a-n/a.) In order to improve the accuracy of the model, it was necessary to incorporate a layer of void space representing nanobubbles on the surface of the OTCE. In agreement with previous reports (Hampton, M. A.; Nguyen, A. v., Nanobubbles and the nanobubble bridging capillary force. *Adv. Colloid Interface Sci.* 2010, 154, (1-2), 30-55; Craig, V. S. J., Very small bubbles at surfaces—the nanobubble puzzle. *Soft Matter* 2011, 7, (1), 40-48), the hydrophobic and rough surface of nanostructured materials (like the OTCE used in these experiments, see FIG. 8B) can trap nano-sized bubbles in concave areas of the substrate that are retained on the surface due to unfavorable interactions with water. Finally, a Cauchy function was used to describe the layer of BSA. This arrangement allowed good agreement (MSE<10) between the experimental and model-generated results. This model enabled the calculation of the thickness of the BSA layer, adsorbed onto the OTCE substrates.

Effect of Potential on the Adsorption Process.

Figure 9:
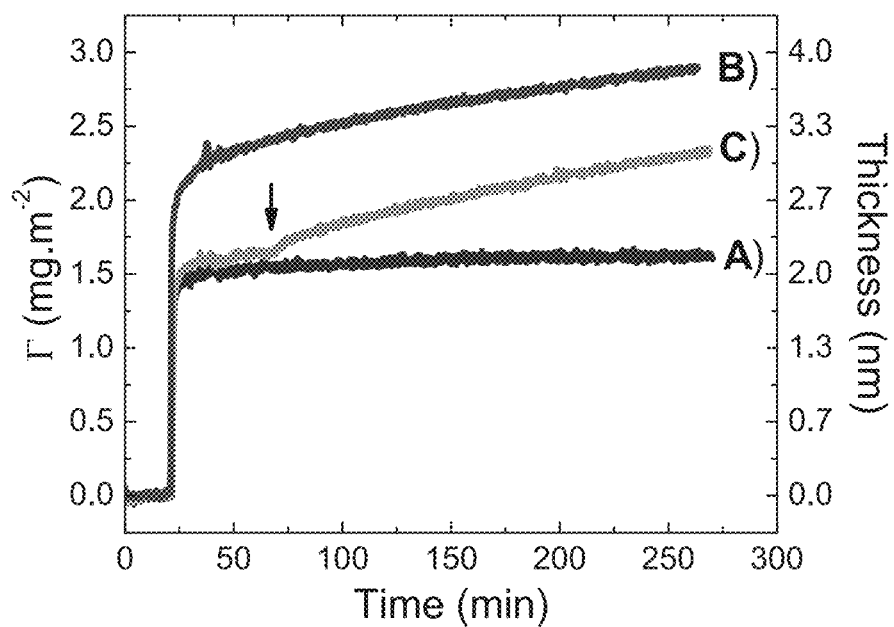
FIG. 9. Dynamic adsorption experiment of BSA onto OTCE at open circuit potential (A), when 800 mV were applied from t=0 (B); and when +800 mV from were applied at t=60 (marked with the arrow). Conditions: 0.50 mg·mL$^{-1}$ BSA, $d_{OTCE}$=19.6±0.7 nm, 10 mmol·L$^{-1}$ citrate buffer at pH=5.7, flow rate of 1 mL·min$^{-1}$.

In order to investigate how the BSA adsorption is affected by the potential applied to the electrode surface, three distinct procedures were initially carried out. Representative results for the three modes are shown in FIG. 9, where the adsorbed amount of BSA was calculated as a function of time. In the first case (A, BSA adsorbed onto the OTCE at OCP), it can be observed that the protein quickly adsorbs to the surface, reaching saturation (1.5±0.2 mg·m$^{-2}$) in less than 45 min, under the selected experimental conditions. Considering the thickness calculated for this layer (2.1±0.3 nm), the dimensions of the protein, and the fact that BSA is a soft protein (prone to spreading (Norde, W.; Giacomelli, C. E., BSA structural changes during homomolecular exchange between the adsorbed and the dissolved states. *J. Biotechnol.* 2000, 79, (3), 259-268; Giacomelli, C. E.; Nonie, W., The Adsorption-Desorption Cycle. Reversibility of the BSA-Silica System. *J. Colloid Interface Sci.* 2001,233, (2), 234-240; van der Veen, M.; Stuart, M. C.; Norde, W., Spreading of proteins and its effect on adsorption and desorption kinetics. *Colloids Surf B* 2007, 54, (2), 136-142)), these results suggest that BSA adopts a side-to-surface conformation under OCP conditions. In agreement with previous reports (Norde, W.; Giacomelli, C. E., BSA structural changes during homomolecular exchange between the adsorbed and the dissolved states. *J. Biotechnol.* 2000, 79, (3), 259-268; Morrin, A.; Guzman, A.; Killard, A. L; Pingarron, J. M.; Smyth, M. R., Characterisation of horseradish peroxidase immobilisation on an electrochemical biosensor by colorimetric and amperometric techniques. *Biosens. Bioelectron.* 2003, 18, (5-6), 715-720; Edri, E.; Regev, O., pH Effects On BSA-Dispersed Carbon Nanotubes Studied by Spectroscopy-Enhanced Composition Evaluation Techniques. *Anal. Chem.* 2008, 80, (11), 4049-4054) this adsorption behavior has been attributed to a combination of hydrophobic and (to a lesser degree) electrostatic interactions between the surface and the protein as well as lateral interactions between protein molecules. As the surface coverage increases, the number of available sites decreases, therefore limiting the adsorption rate and leading to the plateau observed in 9A.

It was also observed that if a potential is applied to the electrode surface (traces B and C in FIG. 9), a significantly higher amount of BSA can be adsorbed to the OTCE. In addition, it was observed that the time at which the potential is applied to the electrode also has a significant impact on the adsorption process. If the potential is applied from the beginning of the experiment (9B), the adsorption process yields the formation of a thicker layer (~2.3 mg·m$^{-2}$, at 40 min) that continues to grow for as long as the potential is applied. As most experiments in the literature have been performed with charged proteins, this observation has been attributed to favorable electrostatic interactions between the surface and the protein (Xie, Y; Liao, c.; Zhou, J., Effects of external electric fields on lysozyme adsorption by molecular dynamics simulations. *Biophys. Chem.* 2013, 179, (0), 26-34 Koutsioubas, A.; Lairez, D.; Zalczer, G.; Cousin, F., Slow and remanent electric polarization of adsorbed BSA layer evidenced by neutron reflection. *Soft Matter* 2012, 8, (9), 2638-2643). It is important to address that although this experimental design clearly supports the hypothesis that a potential applied to the electrode surface influences the adsorption process, it does not allow an independent evaluation of the effect of the applied potential during the initial stages of the interaction. In part, this limitation can be attributed to the high affinity of the protein for the surface that, even in the absence of the external potential, prevails over any other contribution and leads to the accumulation of protein on the surface. In order to separate these effects and perform a kinetic evaluation of the interaction upon the application of the potential to the electrode, experiments described in this manuscript were performed using OTCE substrates that were first modified with a layer of BSA, adsorbed under open circuit potential and using experimental conditions leading to fast saturation of the surface (10 mmol·L$^{-1}$ citrate, pH=4.7, and 0.50 mg·L$^{-1}$ BSA). This set-up also minimized the effect of slight differences (thickness and/or surface properties) between OTCE prepared in different batches. As can be observed in C, the thickness (and the adsorbed amount) of the protein layer increased upon the application of the external potential. The adsorption rate upon the application of the potential ($d\Gamma/dt_1$), calculated from the Γ-t plot in the first seconds of the experiment was 0.014±0.002 mg·m$^{-2}$·min$^{-1}$. This value is substantially lower than the adsorption rate of BSA to the bare surface of the OTCE with or without the application of external potential (2.0±0.3 mg·m$^{-2}$·min$^{-1}$).

It was observed that applying a potential to the electrode surface can lead to higher amounts of protein adsorbed to the surface. For example, in a case where the adsorption process was followed for ~15 hours during the application of +800 mV (see Supplementary Information), a steady increase in the adsorbed amount was observed, reaching almost 8 times the amount obtained at OCP (17.6±0.8 mg·m$^{-2}$). These findings not only are the highest adsorbed amounts reported in literature to date, but also indicate that the effect of the applied potential is able to propagate through the layer of adsorbed BSA. Furthermore, the results shown in FIG. 9 indicate that multiple layers of protein can accumulate on to (conductive) solid surfaces. The time constants for such processes are significantly slower (on the order of 10$^{-3}$) than those associated with the formation of the first layer of protein onto the bare OTCE surface. Since the presented results were verified by the addition of Brilliant Blue (yielding to a signal that is proportional to the amount of protein adsorbed), the observed changes cannot be attributed to the protrusion of the protein layer towards the solution (which could increase the thickness of the layer with constant amount of protein). (Norde, W.; Giacomelli, C. E., BSA structural changes during homomolecular exchange between the adsorbed and the dissolved states. *J. Biotechnol.* 2000, 79, (3), 259-268; Norde, W., My voyage of discovery to proteins in flatland . . . and beyond. *Colloids Surf B* 2008, 61, (1), 1-9; Norde, W., Driving Forces for Protein Adsorption at Solid Surfaces. In *Biopolymers at Interfaces*, Malmsten, M., Ed. Marcel Dekker: New York, 2003; Vol. 110.) Other effects such as the roughness of the substrate (Dolatshahi-Pirouz, A.; Rechendorff, K.; Hovgaard, M. B.; Foss, M.; Chevallier, J.; Besenbacher, F., Bovine serum albumin adsorption on nano-rough platinum surfaces studied by QCM-D. *Colloids Surf. B* 2008, 66, (1), 53-59) or the so-called electro-optic effect (Abbas, Z.; Christian, F.; Thomas Garm, P., Theoretical study of quadratic electro-optic effect in semiconducting zigzag carbon nanotubes, *Phys. Rev. B* 2007, 76, (4), 045403) have been discarded in control experiments.

Effect of the Magnitude of the Applied Potential.

Figure 10:
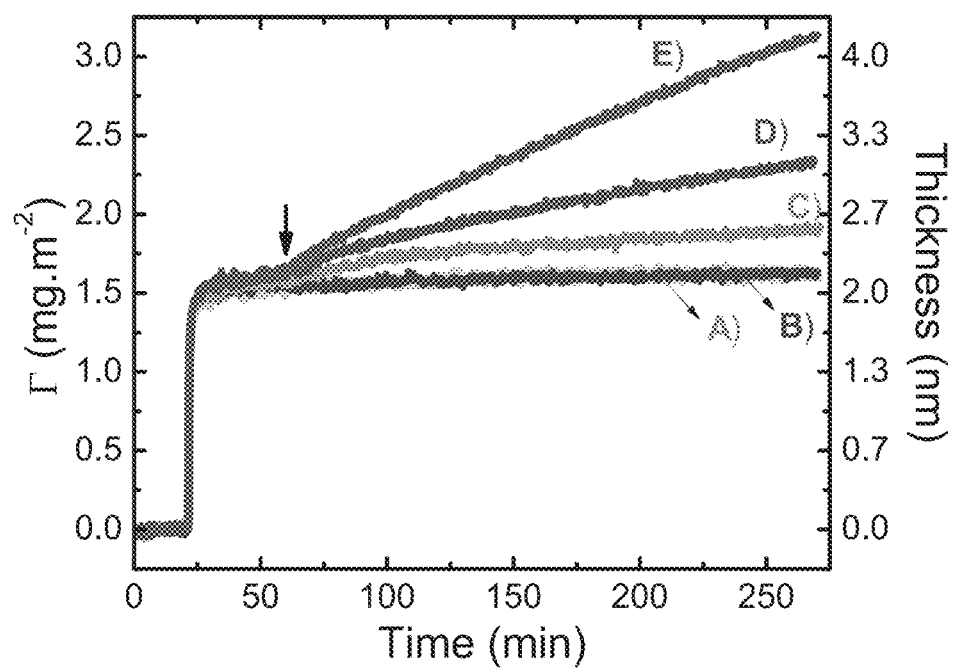
FIG. 10. Effect of applied potential on the dynamic adsorption of 0.50 mg·mL$^{-1}$ BSA onto a BSA/OTCE substrate. Adsorption experiments were performed in 10 mmol·L$^{-1}$ citrate buffer at pH=5.7 with a flow rate of 1 mL·min$^{-1}$ at: A) OCP; B) +500 mV; C) +650 mV; D) +800 mV; and E) +950 mV. The arrow shows the time when the external potential was applied.

The adsorption of BSA was also investigated as a function of the magnitude of the potential applied. In all cases, the adsorption experiment began by recording the baseline (bare electrode) and then allowing a monolayer of BSA to adsorb on the surface of the OTCE at OCP (2.1±0.3 nm). After 60 min, when stable readings were obtained for the Ellipsometric angles, the selected potential was applied and maintained until the end of the experiment. In order to favor electrostatic interactions between BSA and the surface (anodically polarized), experiments were performed at pH=5.7 (above IEP). Representative results are shown in FIG. 10.

As can be observed, when +500 mV was applied to the OTCE, no significant differences in the thickness of the layer (and the adsorbed amount) were observed. The same behavior was also observed when potential values in the −500 mV/+500 MV range were applied (data not shown). Higher potential values, however, induced the accumulation of BSA molecules, leading to significant changes in the thickness of the layer (and the adsorbed amount). In all cases, a fast growth in the protein layer was observed within the first 15 sec upon the application of the potential (dΓ/dt$_1$), followed by a slower process (dΓ/dt$_2$) that remained constant until the end of the experiment. Table 1 summarizes the results calculated (using the least square method) for each of those processes as a function of the potential applied to the electrode surface.

TABLE 1

Initial adsorption rate (calculated after the corresponding potential was applied, dΓ/dt$_1$), linear approximation of the second adsorption process (dΓ/dt$_2$), calculated in the 150-250 min interval of the experiment) and final adsorbed amount of BSA onto the BSA/OTCE substrate as a function of the potential applied to the electrode.

| | dΓ/dt$_1$ (×10$^{-3}$ mg · m$^{-2}$ · min$^{-1}$) | dΓ/dt$_2$ (×10$^{-3}$ mg · m$^{-2}$ · min$^{-1}$) | Γ @ 250 min (mg · m$^{-2}$) |
|---|---|---|---|
| +500 mV | 1.0 ± 0.7 | 0.28 ± 0.02 | 1.62 ± 0.02 |
| +650 mV | 6.4 ± 0.7 | 0.95 ± 0.03 | 1.88 ± 0.03 |
| +800 mV | 14 ± 2 | 2.73 ± 0.02 | 2.29 ± 0.03 |
| +950 mV | 22 ± 3 | 6.63 ± 0.02 | 3.03 ± 0.03 |

The observed increases in the adsorbed amount have been attributed to the polarization of the adsorbed layer and the subsequent electrostatic interaction with the incoming protein molecules. Likely, the inherent flexibility of BSA plays a critical role in the described effect, making its tertiary structure particularly susceptible to structural changes as a response to electrical conditions. Several papers have described the possibility of inducing changes in the adsorbed layer based on redox processes involving the adsorbed protein. It is also important to note that many of these reports are based on the immobilization redox-active proteins (such as ferredoxin (Armstrong, F. A.; Hill, H. A. O.; Walton, N. J., Direct electrochemical oxidation of Clostridium pasteurianum ferredoxin: Identification of facile electron-transfer processes relevant to cluster degradation. *FEBS Letters* 1982, 150, (1), 214-218)) or the adsorption of proteins to electro-active substrates (for example mercury amalgams (Palecek, E.; Ostatna, V., Ionic strength-dependent structural transition of proteins at electrode surfaces. *Chem. Comm.* 2009, (13), 1685-1687), PoPd/C-Ni/GCE (Bian, C.; Xiong, H.; Zhang, X.; Wen, W.; Wang, S., An electrochemical biosensor for analysis of Fenton-mediated oxidative damage to BSA using poly-o-phenylenediamine as electroactive probe. *Biosens. Bioelectron.* 2011, 28, (1), 216-220), or doped polypyrrole (Molino, P. J.; Higgins, M. J.; Innis, P. C.; Kapsa, R. M. I.; Wallace, G. G., Fibronectin and Bovine Serum Albumin Adsorption and Conformational Dynamics on Inherently Conducting Polymers: A QCM-D Study, *Langmuir* 2012, 28, (22), 8433-8445)). In limited cases, BSA shows an oxidation peak at potential values in the 700 mV (Chiku, M.; Ivandini, T. A.; Kamiya, A.; Fujishima, A.; Einaga, Y., Direct electrochemical oxidation of proteins at conductive diamond electrodes. *J. Electroanal. Chem.* 2008, 612, (2), 201-207; Chiku, M.; Nakamura, J.; Fujishima, A.; Einaga, Y., Conformational Change Detection in Nonmetal Proteins by Direct Electrochemical Oxidation Using Diamond Electrodes. *Anal. Chem.* 2008, 80, (15), 5783-5787) to 800 mV (Vacek, J.; Vrba, J.; Zatloukalová, M.; Kubala, M., Electrochemical oxidation of proteins using ionic liquids as solubilizers, adsorption solvents and electrolytes. *Electrochim. Acta*, (0); Wei, M.-Y.; Famouri, P.; Guo, L.-H., Electrocatalytic oxidation of tyrosines shows signal enhancement in label-free protein biosensors. *TrAC, Trends Anal. Chem.* 2012, 39, (0), 130-148) range, which have been attributed to the oxidation of three amino acids (cysteine, tryptophan and tyrosine) that, after protein adsorption, are in close proximity to the electrode surface. In order to verify that redox processes are not associated with the changes described in the manuscript, cyclic voltammetry was performed before and after the protein was adsorbed to the electrode. While it was observed that the adsorption of BSA onto OTCE induced increases in the capacitance of the substrate, no evident redox peaks were obtained within the selected potential window (see Supplementary Information). Therefore, in order to induce fast changes in the adsorbed layer while minimizing the possibility of inducing redox processes in the adsorbed layer, +800 mV was considered optimal and used for the remaining experiments.

Effect of the pH.

Among other alternatives to manipulate the charge of proteins (Gao, Y.; Kyratzis, I., Covalent Immobilization of Proteins on Carbon Nanotubes Using the Cross-Linker 1-Ethyl-3-(3-dimethylaminopropyl)carbodiimide—a Critical Assessment. *Bioconjugate Chem.* 2008, 19, (10), 1945-1950; Hermanson, G. T., *Bioconjugate Techniques*. Second Edition ed.; Academic Press Inc.: 2008), adjusting the pH of the solution is probably the simplest one. Therefore, adsorption experiments were performed in BSA solutions buffered in the 3.7-6.7 range. This range was selected to include the IEP of BSA (4.7 (Carter, D. C.; Ho, J. X., Structure of serum albumin. *Adv. Protein Chem.* 1994, 45, 153-203; Chumbimuni-Torres, K. Y.; Coronado, R. E.; Mfuh, A. M.; Castro-Guerrero, C; Silva, M. F.; Negrete, G. R.; Bizios, R.; Garcia, C. D., Adsorption of Proteins to Thin-Films of PDMS and Its Effect on the Adhesion of Human Endothelial Cells. *RSC Advances* 2011, (4), 706-714)) while retaining sufficient buffer capacity in the ambient solution (citrate $pKa_1$=3.14, $pKa_2$=4.77, $pKa_3$=6.39). (Lide, D. R, CRC *Handbook of Chemistry and Physics*—77th edition 1996-1997. CRC Press: 1996.) In order to gain preliminary insights about the effect of electrode potential on the adsorption of BSA under physiological conditions, additional experiments performed at pH=7.2 (buffered with 10 mmol·L$^{-1}$ phosphate) were also performed. Under these conditions, the zeta potential of BSA spans ±15 mV (Salis, A.; Bostro☐m, M.; Medda, L.; Cugia, F.; Barse, B.; Parsons, D. F.; Ninham, B. W.; Monduzzi, M., Measurements and Theoretical Interpretation of Points of Zero Charge/Potential of BSA Protein. *Langmuir* 2011, 27, (18), 11597-11604) and could lead to conformational changes in the protein (Carter, D. C.; Ho, J. X., Structure of serum albumin. *Adv. Protein Chem.* 1994, 45, 153-203; Ferrer, M. L.; Duchowicz, R.; Carrasco, B.; de la Torre, J. G.; Acuna, A. U., The Conformation of Serum Albumin in Solution: A Combined Phosphorescence Depolarization-Hydrodynamic Modeling Study. *Biophys. J.* 2001, 80, (5), 2422-2430), and varied surface coverage, depending on the pH. (Chumbimuni-Torres, K. Y.; Coronado, R. E.; Mfuh, A. M.; Castro-Guerrero, C.; Silva, M. F.; Negrete, G. R.; Bizios, R.; Garcia, C. D., Adsorption of Proteins to Thin-Films of PDMS and Its Effect on the Adhesion of Human Endothelial Cells. *RSC Advances* 2011, (4), 706-714; Valenti, L. E.; Fiorito, P. A.; Garcia, C. D.; Giacomelli, C. E., The adsorption-desorption process of bovine serum albumin on carbon nanotubes. *J. Colloid Interface Sci.* 2007, 307, (2), 349-356; Wehmeyer, J.; Bizios, R.; Garcia, C. D., Adsorption of Bovine Serum Albumin to Nanostructured Thin-Films of TiO$_2$. *Mat. Sci. Eng.* C 2010, 30, (2), 277-282; Engelhardt, K; Rumpel, A.; Walter, J.; Dombrowski, J.; Kulozik, U; Braunschweig, B.; Peukert, W., Protein Adsorption at the Electrified Air-Water Interface: Implications on Foam Stability. *Langmuir* 2012, 28, (20), 7780-7787.) Therefore, to minimize variability in the thickness of the BSA/OTCE substrate used for the experiments, the first layer of BSA was adsorbed to the OTCE at pH=4.7, yielding a monolayer of protein with an average thickness of 3.5±0.7 nm (after 40 min at OCP). Then, the solution impinging the substrate was sequentially replaced by the buffer at the selected pH value and then by a solution containing BSA (prepared in the selected buffer) to establish the baseline (at OCP and the pH selected for the experiment). No spontaneous adsorption of BSA was observed within the pH range studied. Next, the potential (+800 mV) was applied to the electrode surface and the adsorption process followed by SE. In all cases, the two previously described processes were observed after the potential was applied, leading to the accumulation of BSA on the substrate. As a summary, FIG. 11 shows the relative increase in thickness of the BSA layer after 3 hours, defining 100% as the thickness of the first layer of BSA adsorbed to the OTCE.

Figure 11:
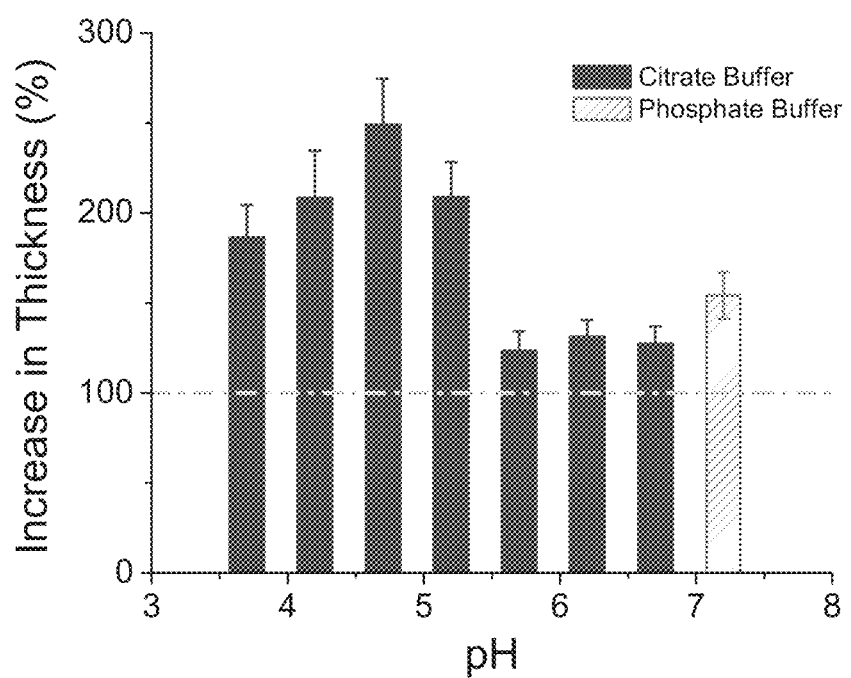
FIG. 11. Effect of pH on adsorption of 0.50 mg·mL$^{-1}$ BSA at +800 mV after adsorption of a BSA layer (3.5±0.7 nm) onto OTCE at OCP and IEP. All experiments were performed in 10 mmol·L$^{-1}$ citrate or phosphate buffer and a flow rate of 1 mL·min$^{-1}$.

As seen in FIG. 11, a significant increase in the thickness (and adsorbed amount) of the BSA layer was observed upon the application of the external potential at all studied pH values. As these changes correspond to the change in thickness upon the application of the potential, they cannot be attributed to differences in conformation of BSA. (Carter, D. C.; Ho, J. X., Structure of serum albumin. *Adv. Protein Chem.* 1994, 45, 153-203.) The increase in thickness (and absorbed amount) obtained above the IEP has traditionally been explained by considering the electrostatic attraction between the positively charged surface and the negatively charged protein; however the large increases obtained below the IEP (electrode polarized at +800 mV, positively charged protein) contrast with the expected electrostatic behavior. Furthermore, the largest change in adsorbed amount was obtained at the IEP, yielding a 2.5-fold increase in the thickness of the resulting layer. These findings suggest that electrostatic interactions between the sorbent surface and the protein being adsorbed (while possibly present) are much less relevant than other processes induced by the external electric field.

Effect of BSA Concentration.

Figure 12:
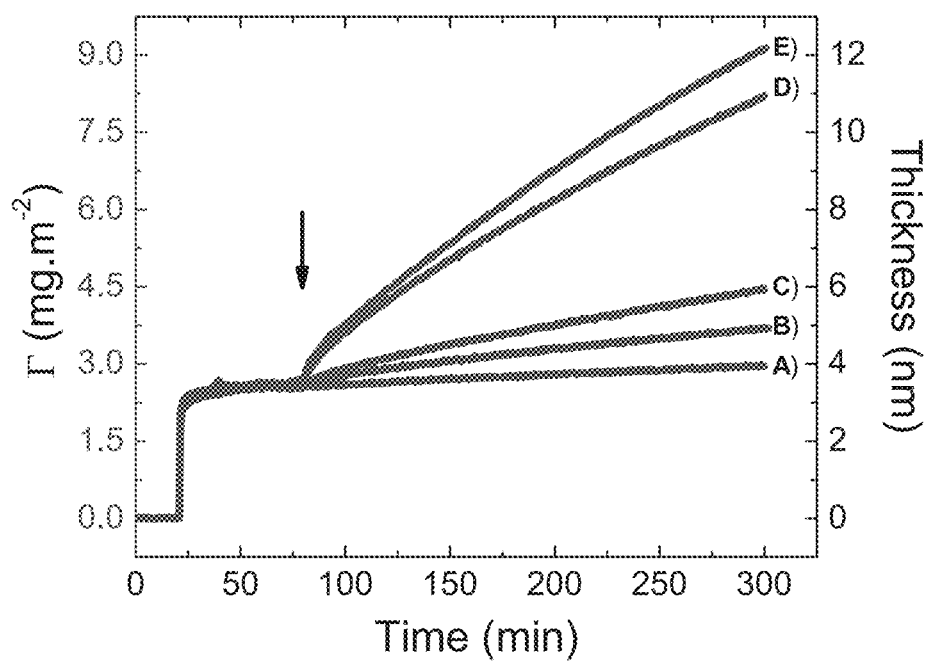
FIG. 12. Effect of BSA concentration on adsorption at +800 mV of: A) 0.01, B) 0.05, C) 0.10, D) 0.50, and E) 1.00 mg·mL$^{-1}$ after a BSA layer (3.5±0.7 nm) was adsorbed onto OTCE at OCP. All experiments were performed in 10 mmol·L$^{-1}$ citrate buffer at IEP and at a flow rate of 1 mL·min$^{-1}$. The arrow shows the time when the external potential was applied.

The effect of BSA concentration was evaluated in the 0.01-1.00 mg·mL$^{-1}$ range. Again, the experiment was performed by first adsorbing a monolayer of BSA (10 mmol·L$^{-1}$ citrate, pH=4.7, 40 min) on the OTCE at OCP. Next, the impinging solution (10 mmol·L$^{-1}$ citrate, pH=4.7, containing BSA at the selected concentration) was pumped to the cell for 20 min to evaluate the stability of adsorbed protein layer and to establish a baseline. Then, the potential was applied and the experiment followed for additional 220 min. FIG. 12 shows representative results related to the dynamic adsorption of BSA in the conditions above described.

As shown in FIG. 12, no desorption was observed after rinsing the surface with either the citrate buffer solution or any of the BSA solutions introduced in the cell. A change in the thickness (and adsorbed amount) of the BSA layer was only observed when the potential was applied to the sorbent surface. The kinetics of the adsorption process ($d\Gamma/dt_1$ and $d\Gamma/dt_2$) were found to be proportional to the concentration of BSA used in each experiment. These results indicate that the attachment of BSA is controlled by the number of protein molecules arriving to the sorbent surface. However, by comparing the adsorption rate obtained at the bare OTCE (2.0±0.3 mg·m$^{-2}$·min$^{-1}$) and the adsorption rate obtained upon the application of the potential (1.75±0.01×10$^{-3}$ mg·m$^{-2}$·min$^{-1}$) using 0.10 mg·mL$^{-1}$ BSA, it is evident that only a small fraction of the incoming protein molecules can be adsorbed in the latter case.

Effect of Ionic Strength.

Figure 13:
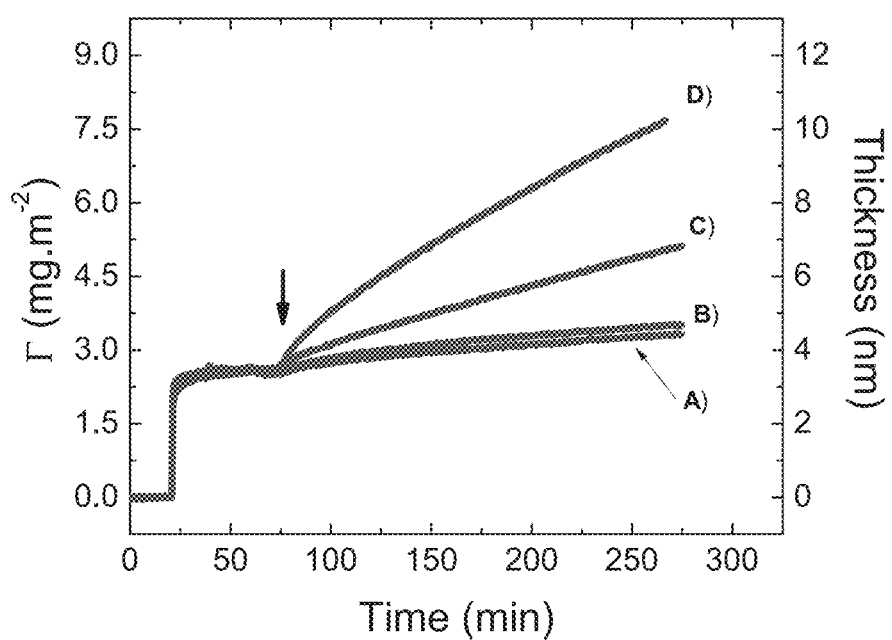
FIG. 13. Dynamic adsorption of BSA (0.50 mg·mL$^{-1}$) at +800 mV onto a BSA/OTCE substrate in citrate buffer at pH=4.7 with the addition of 100 mmol·L$^{-1}$ NaCl (A), 50 mmol·L$^{-1}$ NaCl (B), 25 mmol·L$^{-1}$ NaCl (C), and no NaCl (D). The experiments were performed at a flow rate of 1 mL·min$^{-1}$. The arrow shows the time when the external potential was applied.

In order to investigate the contribution of electrostatic interactions on the adsorption process assisted by potential, the effect of ionic strength was investigated. For these experiments, a monolayer of BSA was first adsorbed (10 mmol·L$^{-1}$ citrate, pH=4.7, 0.50 mg·mL$^{-1}$ BSA, 40 min) on the OTCE at OCP. Next, the impinging solution was switched to a solution containing the selected concentration of NaCl (prepared in 10 mmol·L$^{-1}$ citrate buffer at pH=4.7, 0.50 mg·mL$^{-1}$ BSA) for 20 min. Finally, the potential was changed from OCP to +800 mV to induce accumulation on the surface. The results are summarized in FIG. 13. After the BSA/OTCE substrate was exposed to increasing concentrations of NaCl (between 60 and 80 min), a slight decrease in the thickness of the adsorbed layer was observed. Rather than desorption of BSA from the substrate, this decrease can be attributed to a compression of the protein layer due to shielding of the electrostatic interaction within the adsorbed protein molecules and was not considered significant.

Upon the application of the potential, substantial increases in the thickness (and adsorbed amount) were observed. The kinetics of the adsorption process ($d\Gamma/dt_1$ and $d\Gamma/dt_2$) were found to be inversely proportional to the concentration of NaCl used in each experiment. These results (performed at the IEP of the protein) indicate that the potential applied to the substrate is able to affect the adsorption process and that the ions present in the surrounding solution are able to reduce that interaction. The observed effect is opposite to the behavior observed when the adsorption experiment is performed with charged proteins (Norde, W., Driving Forces for Protein Adsorption at Solid Surfaces. In *Biopolymers at Interfaces*, Malmsten, M., Ed. Marcel Dekker: New York, 2003; Vol. 110; van der Veen, M.; Norde, W.; Stuart, M. c., Electrostatic interactions in protein adsorption probed by comparing lysozyme and succinylated lysozyme. *Colloids Surf. B* 2004, 35, (1), 33-40; de Vos, W. M.; Biesheuvel, P. M.; de Keizer, A.; Kleijn, J. M.; Cohen Stuart, M. A., Adsorption of the Protein Bovine Serum Albumin in a Planar Poly(acrylic acid) Brush Layer As Measured by Optical Reflectometry, *Langmuir* 2008, 24, (13), 6575-6584), where increasing concentrations of ions can increase the adsorbed amount by either complexation with oppositely charged patches or electrostatic shielding.

SUMMARY AND DISCUSSION

The experiments described in this Example have used the surface of an optically transparent carbon electrode saturated with a layer of BSA (as the sorbent substrate) to investigate the effect of an external potential applied on the adsorption of subsequent BSA molecules. Only potential values higher than +500 mV (applied to the substrate), promoted the accumulation of BSA on the substrate. Both the magnitude of the resulting change (arbitrarily determined at 250 min) and the kinetics of the process showed a significant dependence on the experimental conditions selected. In general, application of higher potentials, selection of pH values around the IEP of the protein, high concentrations of protein, and low ionic strengths yielded faster kinetics and the accumulation of larger amounts of BSA on the substrate. The obtained values are compatible with the formation of a disordered system composed of multiple layers of protein.

In a traditional adsorption experiment (performed at OCP), these findings would suggest that the adsorption process is driven by a gain in entropy and the formation of attractive non-covalent interactions such as van der Waals forces and hydrogen bonds of the BSA hydration shell (Engelhardt, K.; Rumpel, A.; Walter, J.; Dombrowski, J.; Kulozik, U.; Braunschweig, B.; Peukert, W., Protein Adsorption at the Electrified Air-Water Interface: Implications on Foam Stability. *Langmuir* 2012, 28, (20), 7780-7787), overpowering lateral electrostatic repulsions, when relevant. At OCP also, BSA molecules could also form an arrangement favoring electrostatic interactions between negative and positive patches in the protein (polar ordering (Engelhardt, K.; Rumpel, A.; Walter, Dombrowski, J.; Kulozik, U.; Braunschweig, B.; Peukert, W., Protein Adsorption at the Electrified Air-Water Interface: Implications on Foam Stability. *Langmuir* 2012, 28, (20), 7780-7787)) or enclose counterions leading to the formation of a multilayer system. However, the described accumulation of BSA on the substrate (OTCE/BSA) was only observed when the potential was applied. Although similar experiments have been previously described, the results obtained around the IEP of the protein are in contrast with the accepted hypothesis that enhanced electrostatic interactions between the polarized substrate and the (oppositely charged) protein are solely responsible for the enhanced adsorption.

To explain these results, it is necessary to consider that the rate of adsorption at the solid/liquid interface can be generally described by the transport of the solute molecules from the bulk to the interface, the attachment to the surface, and the relaxation on the surface. When the concentration at the surface is zero, the flux of adsorbate (J) towards the surface can be described by the following, $$J=0.776v^{1/3}R^{-1}(\alpha Re)^{1/3}D^{2/3}\beta\gamma C$$

where v is the kinematic viscosity of the solvent, R is the inner radius of the tube through which the solution enters the cell, D is the diffusion coefficient of the studied adsorbate, $\beta$ is the probability of attachment, $\gamma$ is a correction factor that accounts for the geometry of the cell (Mora, M. F.; Reza Nejadnik, M.; Baylon-Cardiel, J. L.; Giacomelli, C. E.; Garcia, C. D., Determination of a setup correction function to obtain adsorption kinetic data at stagnation point flow conditions. *J. Colloid Interface Sci.* 2010, 346, (1), 208-215), and C is the concentration of the adsorbate in the bulk. Around the isoelectric point, the probability of attachment of BSA to the bare surface of the OTCE can be approximated to be one, leading to $d\Gamma/dt_0$ values that increase linearly with the concentration of BSA in solution, until a plateau is reached at approximately 0.1 mg·mL$^{-1}$.

Figure 14:
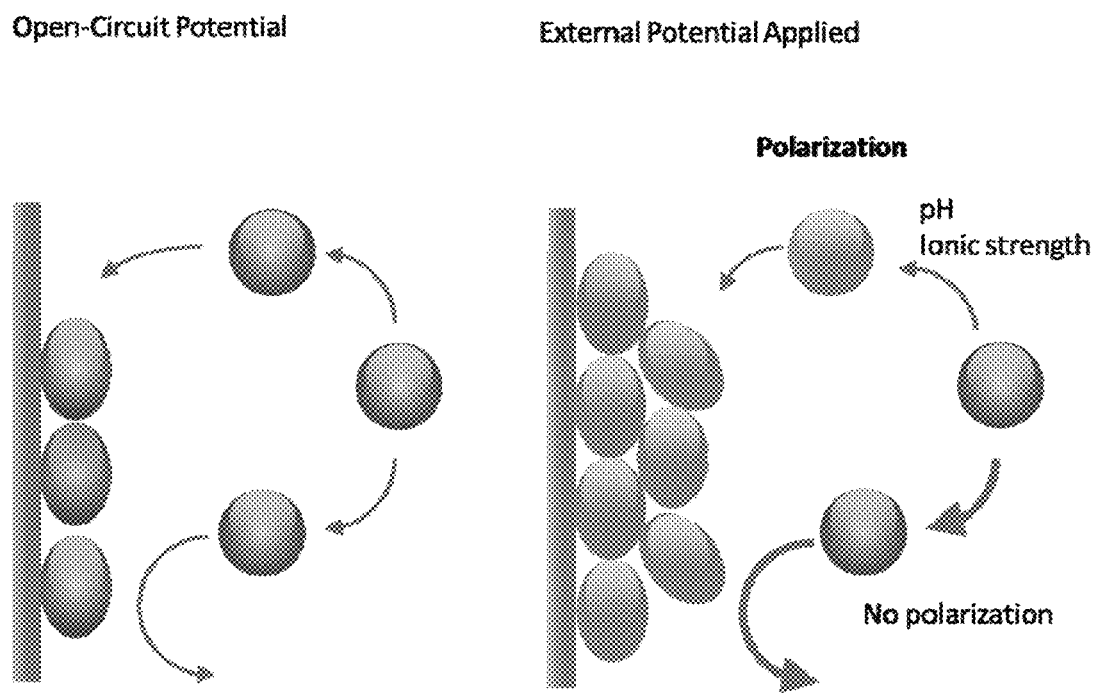
FIG. 14. Schematic representation of the adsorption process of BSA at OCP and in the presence of the external potential.

Therefore, it is reasonable to assume that in the experiments designed to investigate the effect of the potential applied to the electrode, there is enough BSA supplied to the surface to sustain a much higher adsorption rate than the observed. However, the probability of attachment of BSA to the BSA/OTCE surface is much lower than the probability of attachment to the bare OTCE surface. According to the described results, the potential applied to the electrode is able to increase this probability, allowing other proteins to adsorb and grow the layer. The hypothesis is that this phenomenon can be associated to the possibility of polarizing the incoming adsorbing molecules. As schematically shown in FIG. 14, when the experiment is performed at OCP, BSA is able to form a rather compact layer of protein adsorbed to the electrode surface.

As no desorption was observed and thickness values lower than the dimensions of the protein were obtained, it is reasonable to assume that after the interaction with the surface, BSA underwent structural rearrangements (spreading). At this point, and although more protein can reach the substrate, the absence of available sites limits the adsorption and the surface is considered to be saturated.

On the other side, if a potential (larger than +500 mV vs Ag|AgCl|KCl$_{sat}$) is then applied, the surface of the electrode (OTCE/BSA) becomes polarized. The larger the applied potential, the larger the effect. More importantly, comparing the adsorption rates it can be concluded that the probability for incoming proteins to get close enough to the surface, become polarized, and adsorb to the substrate is about 1 in 1000. Because a rather constant adsorption rate was observed (within the time course described in this manuscript), the polarization effect does not seem to be limited by the thickness of the layer.

Because BSA is a "soft" protein, it is probably particularly prone to this polarization effect that can be attributed to the alignment of individual dipoles present in the protein (charged amino acids, peptidic bonds, etc.). The experiments performed as a function of solution pH suggest that this effect is more pronounced at the isoelectric point of the protein. The experiments performed as a function of the concentration of protein indicate that as more protein molecules impinge on the surface, more proteins can become polarized molecules, increasing the adsorption rate. Moreover, this hypothesis is also in agreement with the experiments performed at different ionic strengths, which showed that increasing amounts of salt decreased the adsorption rate. We believe that this observation can be attributed to the shielding effect exerted by the ions in solution, which can shield the incoming proteins from the electric field applied to the surface. Also in agreement with the soft nature of BSA, it is important to note that no significant desorption of BSA was observed, enabling the gentle rinse of the surface without affecting the thickness of the adsorbed layer.

The adsorption of BSA onto OTCE was investigated using spectroscopic ellipsometry, coupled to chronoamperometry and under different experimental conditions (pH, protein concentration, and ionic strength). The experimental results suggest that the potential applied at the BSA/OTCE interface can polarize the substrate and induce the polarization of a fraction of the BSA molecules present in the proximity of the surface. This polarization effect could result in a new route to promote the immobilization of larger amounts of macromolecules to solid surfaces, leading to the development of surfaces with unparalleled biological properties and catalytic activity.

Example 2

Adsorption and Catalytic Activity of Glucose Oxidase Accumulated on OTCE upon the Application of External Potential This Example describes the adsorption of glucose oxidase (GOx) onto optically transparent carbon electrodes (OTCE) under the effect of applied potential and the analysis of the enzymatic activity of the resulting GOx/OTCE substrates. In order to avoid electrochemical interferences with the enzyme redox center, control electrochemical experiments were performed using flavin adenine dinucleotide (FAD) and GOx/OTCE substrates. Then, the enzyme adsorption experiments were carried out as a function of the potential applied (ranged from the open circuit potential to +950 mV), the pH solution, the concentration of enzyme, and the ionic strength on the environment. The experimental results demonstrated that an increase in the adsorbed amount of GOx on the OTCE can be achieved when the potential was applied. Although the increase in the adsorbed amount was examined as a function of the potential, a maximum enzymatic activity was observed in the GOx/OTCE substrate achieved at +800 mV. These experiments suggest that although an increase in the amount of enzyme adsorbed can be obtained by the application of an external potential to the electrode, the magnitude of such potential can produce detrimental effects in the conformation of the adsorbed protein and should be carefully considered. As such, the Example describes a simple and rational approach to increase the amount of enzyme adsorbed on a surface and can be applied to improve the sensitivity of a variety of biosensors.

Experimental Design

Reagents and Solutions.

All aqueous solutions were prepared using 18 MΩ·cm water (NANOpure Diamond, Barnstead; Dubuque, IA) and analytical reagent grade chemicals. Citric acid and β-D-glucose were purchased from Aldrich Chemical Company (Milwaukee, WI). Glacial acetic acid was obtained from EM Science (Gibbstown, NJ). Glucose oxidase (GOx, Type II) from *Aspergillus niger*, horseradish peroxidase (HRP, Type II), o-dianisidine, and flavin adenine dinucleotide disodium salt hydrate (FAD, Fluka) were obtained from Sigma-Aldrich (St. Louis, MO). Sodium hydroxide and sodium phosphate monobasic anhydrous were purchased from Fisher Scientific (Fair Lawn, NJ). The pH of different solutions was adjusted using 1 mol·L$^{-1}$ NaOH and measured using a glass electrode and a digital pH meter (Orion 420A+, Thermo; Waltham, MA). Solutions of GOx (1.00, 0.50, 0.10, 0.05 and 0.01 mg·mL$^{-1}$) were prepared by dissolving a known amount of enzyme in 10 mmol·L$^{-1}$ citrate buffer. The optically transparent carbon electrodes (OTCE) were prepared by pyrolysis of AZ P4330-RS Photoresist purchased from AZ Electronic Materials USA Corp. (Somerville, NJ). The commercial photoresist was diluted to 60% v/v of the as-received material with propylene glycol monomethyl ether acetate (PGMEA 99%, Alfa Aesar; Ward Hill, MA.) The enzymatic assay of GOx adsorbed onto OTCE was performed in 10 mmol·L$^{-1}$ acetate buffer at pH=5.1 which was prepared dissolving sodium acetate anhydrous (Mallinckrodt Baker, Inc., Paris, KY), and 1 mol·L$^{-1}$ acetic acid was used to adjust the pH of buffer solution.

Substrates.

Silica wafers coated with thin optically transparent carbon films (Si/SiO$_2$/OTCE) were used as conductive platforms to adsorb GOx and investigate the effect of the potential applied. The OTCEs were obtained following the procedure described in a previous paper. (T. E. Benavidez, C. D. Garcia, Electrophoresis 34 (2013) 1998.). Briefly, standard <111> silicon wafers (Si/SiO$_2$, Sumco; Phoenix, AZ) were first scored using a computer-controlled engraver (Gravograph 18400, Gravotech; Duluth, GA). The process defined pieces of 1 cm in width and 3 cm in length that were then manually cut and cleaned in piranha solution (30% hydrogen peroxide and 70% sulfuric acid) at 90° C. for 30 min. After thorough rinsing with water, the substrates were immersed and stored in ultrapure water until use. Subsequently the clean wafers were dried at 80° C. for 30 min; a thin layer of photoresist was deposited onto the silicon wafers using a spin coater (Laurell, Model WS-400-6NPP; North Wales, PA). Next, the photoresist-coated substrates were heated at 110° C. for 60 s in a convection oven to evaporate the solvent and then transferred to a tube furnace (Thermolyne F21135, Barnstead International; Dubuque, IA) for pyrolysis. The carbonization step began by flushing the system at 1 L·min$^{-1}$ with forming gas (95%) Ar+5% H$_2$, v/v) for 5 min. Next, the temperature was increased to 1000° C. at 20° C.·min$^{-1}$. After pyrolysis during 1 h, the system was allowed to cool to room temperature. Finally, the samples were stored in a Petri dish for a minimum of 3 days to complete the spontaneous surface oxidation.

Spectroscopic Ellipsometry.

Adsorption experiments were performed using a variable angle spectroscopic ellipsometer (WVASE, J. A. Woollam Co.; Lincoln, NE) following a procedure described elsewhere. (M. R. Nejadnik, L. Francis, C. D. Garcia, Electroanalysis 23 (2011) 1462; M. F. Mora, M. Reza Nejadnik, J. L. Baylon-Cardiel, C. E. Giacomelli, C. D. Garcia, J. Colloid Interface Sci. 346 (2010) 208; H. Fujiwara, Spectroscopic ellipsometry: principles and applications. John Wiley & Sons, 2007.) The basis of SE is the measurement of change in the reflectance and phase difference between the parallel ($R_P$) and perpendicular ($R_S$) components of a polarized light beam upon reflection from a surface. The intensity ratio of $R_P$ and $R_S$ can be related to the ellipsometric angles ($\psi$ and $\Delta$) using the following equation:

$$\tan(\Psi)e^{i\Delta} = \frac{R_P}{R_S}$$

The collected data (amplitude ratio ($\Psi$) and phase difference ($\Delta$) as function of wavelength or time) was modeled using the WVASE software package (J. A. Woollam Co.; Lincoln, NE) and the mean square error (MSE, calculated by a built-in function in WVASE) was used to quantify the difference between the experimental and model-generated data. In agreement with previous reports, MSE <15 was considered acceptable. (M. R. Nejadnik, L. Francis, C. D. Garcia, Electroanalysis 23 (2011) 1462; M. F. Mora, M. Reza Nejadnik, J. L. Baylon-Cardiel, C. E. Giacomelli, C. D. Garcia, J. Colloid Interface Sci. 346 (2010) 208.) The ellipsometric measurements were interpreted using an optical model which describes the microstructure of the system under study in terms of the refractive index (n), extinction coefficient (k), and thickness (d). Therefore, the ellipsometric model used in this article to describe the experimental data was previously developed in our lab and presented in preceding papers. (T. E. Benavidez, C. D. Garcia, Electrophoresis 34 (2013) 1998; T. E. Benavidez, C. D. Garcia, Langmuir 29 (2013) 14154.) Likewise, five uniaxial layers with optical axes parallel to the surface substrate were considered in this optical model. Furthermore, because the experiments were performed in aqueous media, the optical properties of water were also considered. Concisely, the dielectric function of Si (bulk, d=1 mm) and $SiO_2$ (d=2.1±0.5 nm) were used to describe the optical behavior of silica wafer. Then, the optical constants of carbon (T. E. Benavidez, C. D. Garcia, Electrophoresis 34 (2013) 1998) were used to define the ellipsometric response of OTCE (d=19.6±0.7 nm). Next, a void layer representing nanobubbles (M. A. Hampton, A. V. Nguyen, Adv. Colloid Interface Sci. 154 (2010) 30; J. W. G. Tyrrell, P. Attard, Phys. Rev. Lett. 87 (2001) 176104; B. M. Borkent, S. M. Dammer, H. Schonherr, G. J. Vancso, D. Lohse, Phys. Rev. Lett. 98 (2007) 204502; V. S. J. Craig, Soft Matter 7 (2011) 40) formed on the hydrophobic and rough surface of the OTCE was also incorporated to improve the optical model. Finally, the GOx layer adsorbed on the OTCE was described successfully using a Cauchy function.

Dynamic adsorption experiments were performed in a modified electrochemical cell (M. F. Mora, M. Reza Nejadnik, J. L. Baylon-Cardiel, C. E. Giacomelli, C. D. Garcia, J. Colloid Interface Sci. 346 (2010) 208) (J. A. Woollam Co.; Lincoln, NE) mounted directly on the vertical base of the ellipsometer, with an incident angle of 70° C. Before the adsorption of GOx on the substrate, the thickness of the OTCE was always measured by placing the substrate in the ellipsometry cell and performing a spectroscopic scan from 300 to 1000 nm (with 10 nm step) using 10 mmol·L$^{-1}$ buffer solution as the ambient medium. Then, the adsorption experiment was started recording a baseline of the bare OTCE at open circuit potential (OCP, the potential at which no current flows through the cell) while buffer solution was pumped inside the cell at a rate of 1 mL·min$^{-1}$. After 20 min of baseline, the enzyme solution was injected to adsorb a monolayer of GOx on the OTCE at OCP (+180±20 mV). As a result, an initial fast process followed by a slower one was always observed. When a plateau in the signal was noticed, the selected potential (+500, +650, +750, +800 or +950 mV) was applied and kept until the end of the experiment. The change of potential was carried out employing a CHI812B Electrochemical Analyzer (CH Instrument, Inc.; Austin, TX), a silver/silver Chloride (Ag|AgCl|KCl$_{sat}$) reference electrode, and a platinum wire as the counter electrode. Lastly, a spectroscopic scan was performed to obtain the thickness of the protein layer after the adsorption assisted by potential. The procedure described above provided the data to calculate the thickness of the OTCE, the protein film, and the adsorbed amount of the GOx on the thin carbon electrodes.

Enzymatic Assays.

GOx (EC 1.1.3.4) is a homo-dimeric glycoprotein with a molecular weight of 160 kDa (7 nm×5.5 nm×8 nm (H. J. Hecht, D. Schomburg, H. Kalisz, R. D. Schmid, Biosens Bioelectron 8 (1993) 197)) which contains one tightly, non-covalently bound flavin adenine dinucleotide (FAD) per monomer as cofactors. (R. Wilson, A. P. F. Turner, Biosens. Bioelectron. 7 (1992) 165; S. B. Bankar, M. V. Bule, R. S. Singhal, L. Ananthanarayan, Biotechnol. Adv. 27 (2009) 489.) FAD makes up part of the active site and acts as redox center of the enzyme. In the reductive step of the enzyme during the enzymatic reaction, GOx catalyses the oxidation of β-D-glucose to β-D-glucono-δ-lactone by reducing FAD to $FADH_2$. Then, the oxidation of GOx takes place by utilizing molecular oxygen ($O_2$) as an electron acceptor and the simultaneous production of hydrogen peroxide ($H_2O_2$). (H. J. Hecht, D. Schomburg, H. Kalisz, R. D. Schmid, Biosens. Bioelectron. 8 (1993) 197.) The optimum pH of GOx is 5.5 and the isoelectric point (IEP) is 4.2. (J. H. Pazur, K. Kleppe, Biochemistry 3 (1964) 578.) In order to evaluate the biological activity of the substrates modified with GOx, the enzymatic activity was measured spectrophotometrically. The technique was based on the reaction of β-D-glucose with $O_2$ and $H_2O$ in presence of GOx to produce β-D-glucono-δ-lactone and $H_2O_2$. Then, the $H_2O_2$ was used to oxidize o-dianisidine in presence of horseradish peroxidase (HRP) to generate a color change which was monitored at 500 nm. (S. B. Bankar, M. V. Bule, R. S. Singhal, L. Ananthanarayan, Biotechnol. Adv. 27 (2009) 489.) With the purpose of controlling the area exposed to the enzyme solution during the adsorption experiment, poly(dimethylsiloxane) (PDMS) was used to cover the top portion and back side of the substrate. After GOx was adsorbed onto the OTCE, PDMS was removed exposing a constant area of substrate modified with the adsorbed GOx. Then, the GOx/OTCE substrate was placed in a quartz cuvette filled with a mixture of β-D-glucose, o-dianisidine, and HRP in acetate buffer pH=5.1 (according to the assay protocol) to begin the spectrophotometric measurement. In order to mix continuously the solution during the measurement, a magnetic bar was placed inside the cuvette, and a spinette cell stirrer (Starna Cells, Inc.; Atascadero, CA) was used to homogenize the solution. To follow the progress of enzymatic reaction, the change in absorbance at 500 nm was recorded using a spectrophotometer Genesys 10-S Thermo (Electron Corporation; Madison, WI).

Cyclic Voltammetry.

Cyclic voltammetry (CV) was used to study the electrochemical response of FAD on the OTCE, and to define the working potential range for the adsorption studies. (A. Guiseppi-Elie, C. Lei, R. H. Baughman, Nanotechnology 13 (2002) 559.) In addition, the electrochemical behavior of the GOx/OTCE substrates was also investigated by CV after adsorption of the enzyme at the selected potential (OCP, +500, +650, +750, +800, and +950 mV). In all cases, experiments were performed in 10 mmol·L$^{-1}$ citrate buffer using a CHI812 Electrochemical Analyzer (CH Instruments, Inc.; Austin, TX), silver/silver chloride (Ag|AgCl|KCl$_{sat}$) reference electrode, and a platinum wire as the counter electrode.

Molecular Dynamics Simulations.

To gain preliminary insights about the potential effects of the potential applied on the structure of the protein, simulations were performed using the NAMD 2.9 package (J. C. Phillips, R. Braun, W. Wang, J. Gumbart, E. Tajkhorshid, E. Villa, C. Chipot, R. D. Skeel, L. Kalé, K. Schulten, J. Comput. Chem. 26 (2005) 1781) with Charmm22 force field. The results were analyzed using VMD. (W. Humphrey, A. Dalke, K. Schulten, J. Mol. Graphics 14 (1996) 33.) The initial protein coordinates were retrieved from the Protein Data Bank (PDBID: 1CF3). Before performing the simulation, the protein was solvated with water (TIP3) and placed in a rectangular box of 13.0 nm×12.8 nm×10.8 nm at physiological pH (7.3). The system was neutralized by the addition of NaCl. In all cases, the systems were minimized and equilibrated until reaching the equilibrium state (~1 ns). Subsequently, the Molecular Dynamics production was performed in the NVT ensemble at 292 K using a time step of 2 fs, the SHAKE algorithm, and periodic boundary conditions. In order to evaluate the polarization effects on the GOx, an external electric field of 0.43 V·nm$^{-1}$ was applied along the z direction during the time selected for the simulation (40 ns). (Kubiak-Ossowska, P. A. Mulheran, Langmuir 28 (2012) 15577.) The control simulation was carried out using identical conditions but without the external electric field. Electrostatic potential maps and dipole moment were calculated using APBS 1.4 (Nathan A. Baker, David Sept, Simpson Joseph, Michael J. Holst, J. A. McCammon, PNAS 98 (2001) 10037) and VMD Dipole Watcher Plugin, respectively.

Results and Discussion

Molecular Modeling.

As it can be observed in FIG. 1A, and in agreement with previously-reported calculations (C. E. Felder, J. Prilusky, I. Silman, J. L. Sussman, Nucleic Acids Res. 35 (2007) W512) GOx shows an initial (intrinsic) molecular dipole moment of about 700 D. As the simulation progressed, it was observed that the potential applied was able to induce substantial conformational changes along with the corresponding increases in the molecular dipole moment, reaching a final value of 2730 D (40 ns). It is also important to point out that the most significant conformational changes were obtained within the first 10 ns of the simulation, followed by a slower process that stretches the protein along the electric field direction (FIG. 1B).

Figure 7:
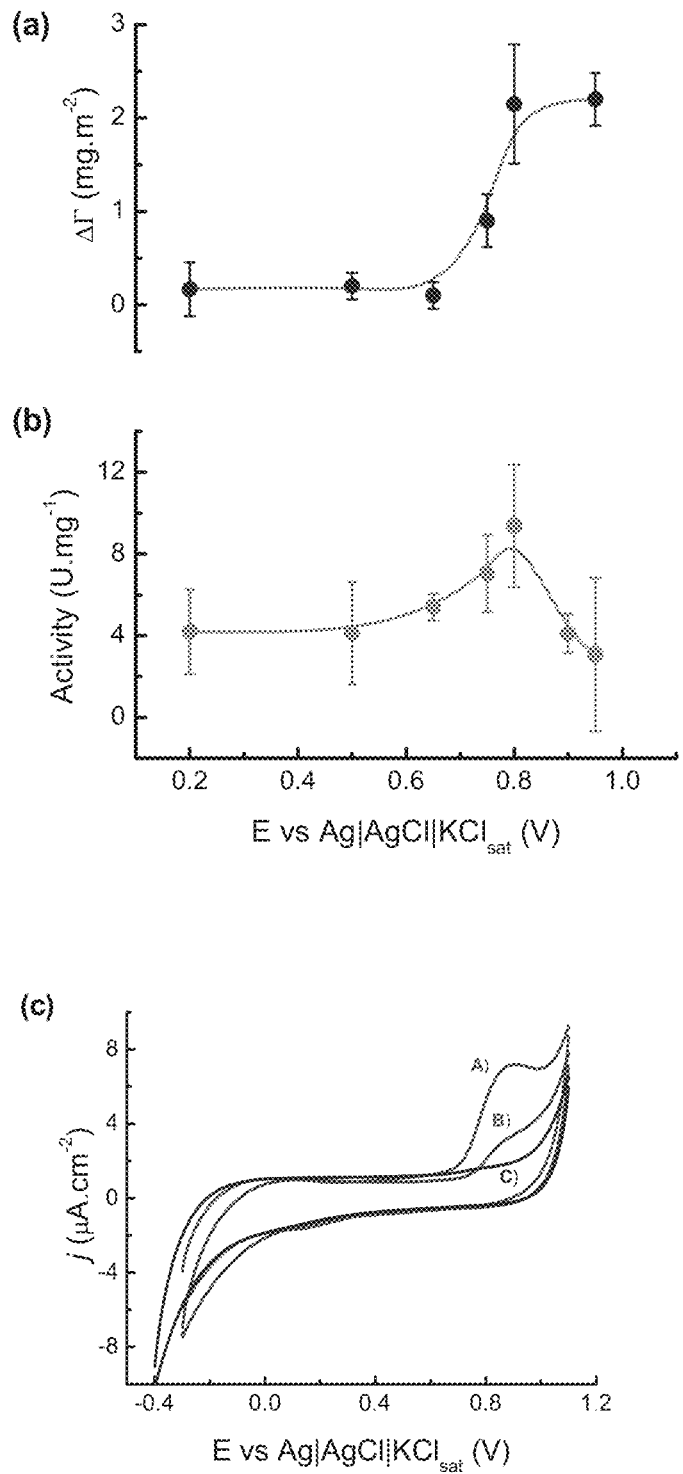
FIG. 7. (A) Change in the adsorbed amount (ΔΓ) and (B) specific enzyme activity of GOx/OTCE substrates as a function of the potential applied during the secondary adsorption experiments. (C) Cyclic voltammograms of GOx adsorbed onto the OTCE after adsorption at: A) +500 mV (the same response was observed at OCP): B) +650 mV; and C) +950 mV. All experiments were performed in 10 mmol·L$^{-1}$ citrate buffer at pH=4.2 and a flow rate of 1 mL·min$^{-1}$.

Although this computational model does not include the redox reactions described in FIG. 7B (vide infra), the results of the simulation provide supporting information related to the molecular consequences of the polarization effect in agree with a recently report. (I. Bekard, D. E. Dunstan, Soft Matter 10 (2014) 431.) The observed changes can be attributed to the redistribution of charged amino acids on the protein that, under extreme conditions, could even affect the shape of the protein. (S. Miller, Janin, A. M. Lesk, C. Chothia, J. Mol. Biol. 196 (1987) 641.) Considering these findings, the electrochemical behavior of the substrates was subsequently investigated.

Electrochemical Behavior of GOx/OTCE Substrates.

Figure 2:
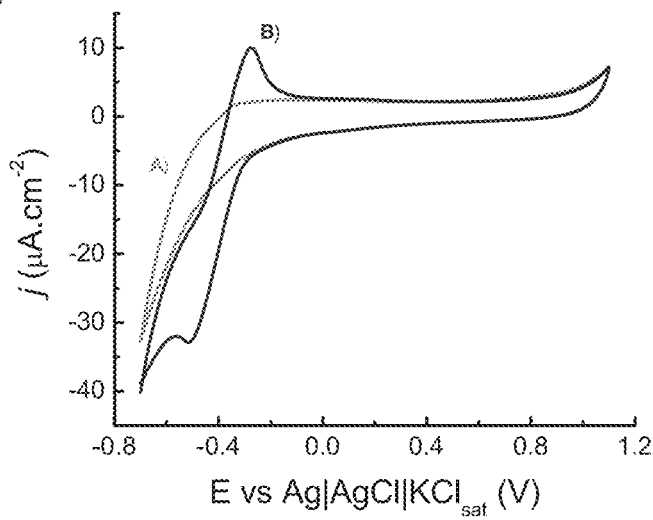
FIG. 2. (A) Cyclic voltammograms of OTCE performed in: A) 10 $mmol \cdot L^{-1}$ citrate buffer at pH=4.2; and B) 0.1 $mmol \cdot L^{-1}$ FAD dissolved in 10 $mmol \cdot L^{-1}$ citrate buffer at pH=4.2. (B) Cyclic voltammograms of GOx/OTCE substrate after adsorption of GOx at +500 mV. All voltammograms were obtained in 10 $mmol \cdot L^{-1}$ citrate buffer at pH=4.2 and correspond to: A) $1^{st}$ cycle; B) $2^{nd}$ cycle; and C) $3^{rd}$ cycle. Scan rate: 50 $mV \cdot s^{-1}$ FIG. 3. Effect of applied potential on the adsorption kinetic of 0.50 $mg \cdot mL^{-1}$ GOx after adsorption of a GOx layer (4.1±0.3 nm) onto OTCE at OCP. Adsorption experiments were performed in 10 $mmol \cdot L^{-1}$ citrate buffer at pH=4.2 and a flow rate of 1 $mL \cdot min^{-1}$ at: A) OCP; B) +500 mV; C) +650 mV; D) +750 mV; E) +800 mV; and E) +950 mV. The arrow shows the time which the external potential was applied.
Figure 2:
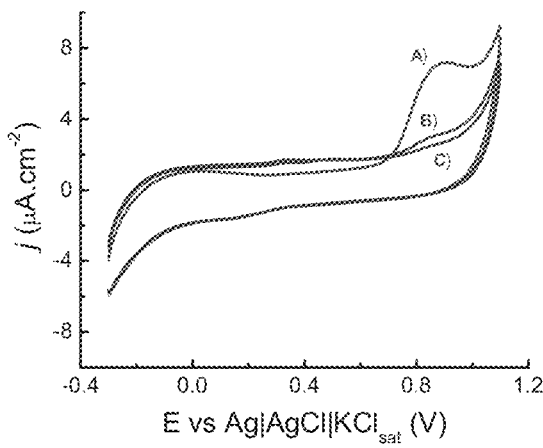

In order to define the working potential range to perform the protein adsorption experiments, the electrochemical behavior of the OTCE, GOx, and FAD was investigated by cyclic voltammetry. Representative results of current density (j, µA·cm$^{-2}$) as a function of the potential applied to the OTCE (working electrode) are shown in FIG. 2. As it can be observed in FIG. 2A (trace A), no significant features were observed in potentiodynamic profile when the plain OTCE was immersed in the selected buffer. On the other hand, FIG. 2A (trace B) shows that well-defined peaks were obtained when the electrode was immersed in a solution containing FAD. Considering reference values from previous literature reports (J. M. Goran, S. M. Mantilla, K. J. Stevenson, Anal. Chem. 85 (2013) 1571; A. Szucs, G. D. Hitchens, J. O. M. Bockris, J. Electrochem. Soc. 136 (1989) 3748; M. Wooten, S. Karra, M. Zhang, W. Gorski, Anal. Chern, 86 (2013) 752) these peaks can be assigned to a quasi-reversible redox process involving the oxidation of FADH$_2$ ($E_P$=−271 mV) and the reduction of FAD ($E_P$=−515 mV) during the anodic and cathodic sweep, respectively. In order to avoid potential interferences with the electrochemical response of GOx-FAD (that under the selected experimental conditions overlaps with the evolution of H$_2$, see trace A in FIG. 2A), the potential value corresponding to +200 mV was defined as the lower limit for the adsorption experiments.

On the other hand, as it can be observed in FIG. 2B, an irreversible electrochemical process (oxidation, $E_P$=+850 mV) was observed when the OTCE surface was saturated with a layer of GOx. This oxidation peak, that sequentially decreased as a function of the number of sweeping cycles has been attributed to the irreversible oxidation of three amino acids (cysteine, tryptophan, and tyrosine) that, after protein adsorption, are in close proximity to the electrode surface (J. Vacek, J. Vrba, M. Zatloukalová, M. Kubala, Electrochim. Acta (2014); M.-Y. Wei, P. Famouri, L.-H. Guo, TrAC, Trends Anal. Chem. 39 (2012) 130) and could, in some extreme cases, lead to cleavage events. (H. P. Permentier, A. P. Bruins, J. Am. Soc. Mass Spectrom. 15 (2004) 1707.) Considering these peak potentials, the results described support the hypothesis that the oxidation process observed at positive potentials is related to the amino acids and is clearly decoupled from the redox activity of the FADH$_2$; (present in the active site). This irreversible chemical change on the GOx layer is critical to consider the enzymatic activity of adsorbed GOx, vide infra.

Effect of the Magnitude of Applied Potential on the Adsorption of GOx.

Figure 3:
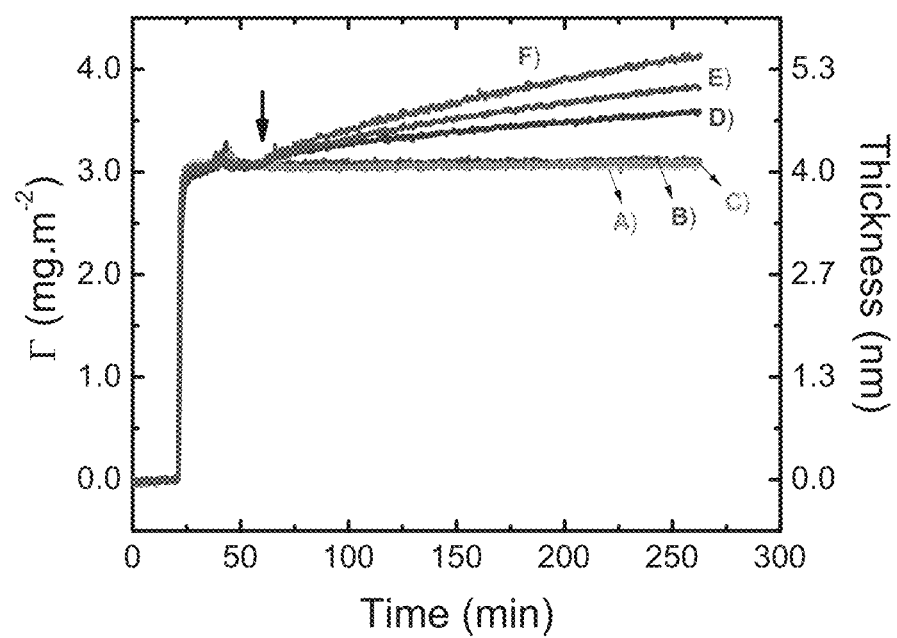

In order to study the effect of the applied potential, adsorption experiments were performed by recording the baseline (bare OTCE) and then allowing GOx to adsorb on the surface of the OTCE at OCP (4.1±0.3 nm). In agreement with previous reports (M. R. Nejadnik, L. Francis, C. D. Garcia, Electroanalysis 23 (2011) 1462; A. Szucs, G. D. Hitchens, J. O. M. Bockris, J. Electrochem. Soc. 136 (1989) 3748), these values correspond to an adsorbed amount of 4.1±0.1 mg·m$^{-2}$, which are in line with the formation of a monolayer of enzyme on the surface of the OTCE with side-on orientation. When stable readings for the ellipsometric angles were obtained (typically around 60 min), the selected potential (OCP, +500, +650, +750, +800, or +950 mV) was applied and maintained until the end of the experiment. FIG. 3 shows representative examples of the results obtained during the adsorption of the first layer of GOx (at OCP) and the secondary adsorption process, induced by the application of the external potential (marked as ↓). In all cases, the secondary adsorption process proceed as a fast growth process in the protein layer within the first 15 sec upon the application of the potential ($d\Gamma/dt_1$), followed by a much slower one ($d\Gamma/dt_2$) that remained almost constant until the end of the experiment.

As it can be observed, no significant differences (with respect to the values obtained at OCP) were found in the adsorbed amount of GOx when the OTCE potential was changed to +500 mV or +650 mV (traces B and C respectively). However, considerable increases in thickness (and adsorbed amount of GOx) were obtained when the imposed potential was fixed at ≥+750 mV. Additionally, it was observed that the rate of GOx adsorption was found to be proportional to the applied potential. Table 1 summarizes the results calculated (using the least square method) for each of those processes as a function of the potential applied to the electrode surface.

TABLE 1

Initial adsorption rate (calculated after the corresponding potential was applied, $d\Gamma/dt_1$), linear approximation of the second adsorption process ($d\Gamma/dt_2$, calculated in the 150-250 min interval of the experiment) and final adsorbed amount of GOx onto the GOx/OTCE substrate as a function of the potential applied to the Table electrode.

| | $d\Gamma/dt_1$ (×10$^{-3}$ mg · m$^{-2}$ · min$^{-1}$) | $d\Gamma/dt_2$ (×10$^{-3}$ mg · m$^{-2}$ · min$^{-1}$) | $\Gamma$ @ 250 min (mg · m$^{-2}$) |
|---|---|---|---|
| +500 mV | 2 ± 7 | 0.16 ± 0.03 | 3.10 ± 0.04 |
| +650 mV | 0 ± 9 | 0.38 ± 0.03 | 3.09 ± 0.04 |
| +750 mV | 20 ± 5 | 1.73 ± 0.03 | 3.57 ± 0.02 |
| +800 mV | 16 ± 5 | 3.06 ± 0.02 | 3.81 ± 0.03 |
| +950 mV | 29 ± 7 | 4.11 ± 0.03 | 4.10 ± 0.03 |

In line with the results obtained with BSA, these experiments suggest that the accumulation of GOx can be also enhanced by the so-called polarization effect (T. E. Benavidez, C. D. Garcia, Langmuir 29 (2013) 14154) but the minimum potential required to induce the accumulation of GOx (+750 mV) is significantly higher than the minimum value required to induce the accumulation of BSA (+650 mV). This difference could be attributed to a combination of the initial dipole moment of the protein (at IEP and OCP), the structural molecular weight and stability of the protein, and the magnitude of the dipole induced on the GOx molecules when the electric field is imposed. In this case it is reasonable to consider that larger and harder proteins, like GOx, would be more resistant (than smaller, softer proteins like BSA) to undergo conformational transitions (W. Norde, C. E. Giacomelli, J. Biotechnol. 79 (2000) 259; C. A. Haynes, W. Norde, J. Colloid Interface Sci. 169 (1995) 313; W. Norde, Colloids Surf. B 61 (2008) 1) and therefore would require the application of higher potential values to induce the polarization and the subsequent accumulation on the electrode surface. In other words, the results suggest that the susceptibility of the protein to the electric field applied to the sorbent surface (polarizability) could be associated with the conformational rigidity and the size of the adsorbing protein.
Effect of GOx Concentration.

Figure 4:
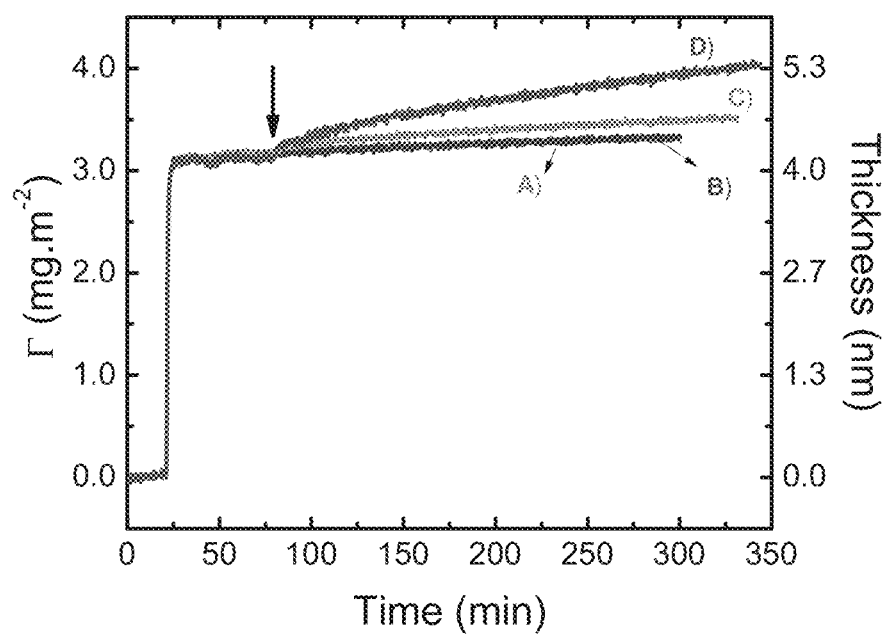
FIG. 4. Effect of GOx concentration on adsorption at +800 mV of: A) 0.01, B) 0.05, C) 0.10, and D) 0.50 $mg \cdot mL^{-1}$ after a GOx layer (4.1±0.3 nm) was adsorbed onto OTCE at OCP. All experiments were performed in 10 $mmol \cdot L^{-1}$ citrate buffer at IEP and a flow rate of 1 $mL \cdot min^{-1}$. The arrow shows the time which the external potential was applied.

The effect of GOx concentration was investigated in the 0.01-0.50 mg·mL$^{-1}$ range. Once again, the experiment was performed by first adsorbing a monolayer of GOx (10 mmol·L$^{-1}$ citrate, pH=4.2, 40 min) on the bare OTCE at OCP. Next, the impinging solution (10 mmol·L$^{-1}$ citrate, pH=4.2, containing GOx at the selected concentration) was pumped into the cell for 20 min to evaluate the stability of adsorbed protein layer and to establish the baseline. Then, +800 mV were applied and the experiment followed for at least another 220 min. FIG. 4 summarizes the results of the dynamic adsorption experiments (adsorbed amount and layer thickness obtained as a function of time). As it can be observed, the accumulation of enzyme molecules onto the GOx/OTCE substrates was only observed upon the application of the potential to the electrode (at t=80 min). Additionally, no spontaneous desorption/adsorption processes were observed when the citrate buffer or the selected solution of GOx were introduced in the cell at OCP, respectively.

Also, no differences were observed in the dynamic adsorption experiments of GOx when 0.01 and 0.05 mg·mL$^{-1}$ of enzyme were used to perform the experiments. On the other hand, the increase in the adsorbed amount (and thickness) was found to be proportional to the concentration of enzyme solution impinging the substrate. Consequently, the experimental results propose that the attachment of GOx to the polarized surface was controlled by the number of enzyme molecules incoming to the substrate, Considering the polarization of protein molecules as one of the most relevant driving forces of protein adsorption induced by potential, the increase of the number of enzymes incoming to the polarized substrate increased the chance of enzyme became polarized and the subsequent protein adsorption.
Effect of pH on the GOx Adsorption.

Figure 5:
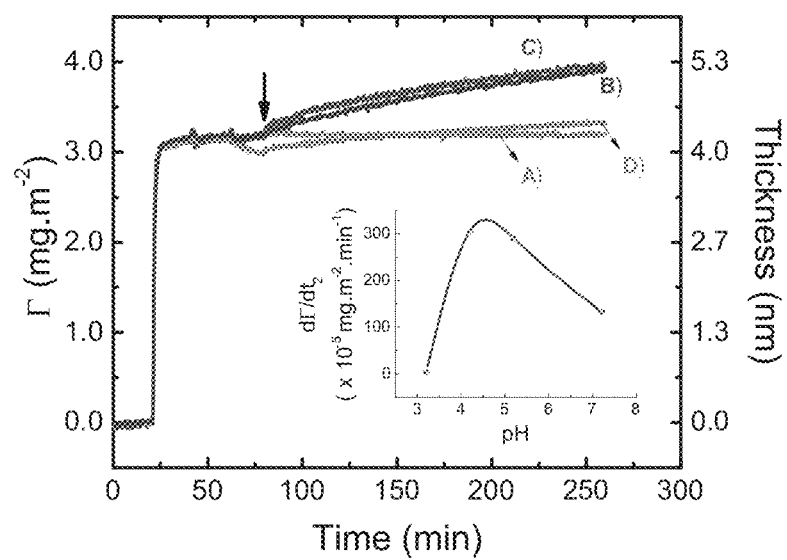
FIG. 5. Effect of pH on adsorption of 0.50 $mg \cdot mL^{-1}$ GOx at +800 mV after adsorption of a GOx layer (4.1±0.3 nm) onto OTCE at OCP and IEP. All experiments were performed in 10 $mmol \cdot L^{-1}$ citrate or phosphate buffer and a flow rate of 1 mL·min$^{-1}$ at pH=3.7 (A), 4.2 (B), 5.2 (C), and 7.2 (D). The arrow shows the time which the external potential was applied.

In order to evaluate the effect of protein charge on the adsorption process, adsorption experiments were performed using GOx solutions buffered in the 3.7-5.2 range of pH. This range was selected to include the IEP of GOx (4.2) (J. H. Pazur, K. Kleppe, Biochemistry 3 (1964) 578) while retaining sufficient buffer capacity in the ambient solution (citrate $pKa_1$=3.14, $pKa_2$=4.77, $pKa_3$=6.39). (D. R. Lide, CRC Handbook of Chemistry and Physics—77th edition 1996-1997. CRC Press, 1996.) Moreover, to gain preliminary insights about the effect of electrode potential on the adsorption of GOx under physiological conditions, an additional experiment was performed at pH=7.2 (buffered with 10 mmol·L$^{-1}$ phosphate). As previously described, a first layer of GOx was adsorbed to the OTCE at OCP and the IEP, yielding a compact monolayer of protein with an average thickness of 4.1±0.3 nm. Then, the solution impinging the substrate was sequentially replaced by the buffer at the selected pH and by a solution containing GOx (prepared in the selected buffer) to establish the baseline (at OCP and the pH selected for the experiment). Although slight changes in the thickness of the layers were observed (product of small rearrangements in the adsorbed layer) no significant spontaneous adsorption or desorption of GOx was observed within the pH range studied. Once the new baseline was established, the potential (+800 mV) was applied to the electrode surface and the adsorption process followed by SE. FIG. 5 shows representative examples of the results obtained during the dynamic adsorption of GOx at different pH values. As summarized in FIG. 5 (see insert), the maximum secondary adsorption rate of GOx was observed at the IEP (3.06±0.02×10$^{-3}$ mg·m$^{-2}$·min$^{-1}$). These results suggest that in the case of GOx, the electrostatic interactions between the incoming molecules and those already adsorbed at the surface of the electrode are able to overcome the dipole-dipole interactions induced by the potential applied to the electrode surface and limit the secondary adsorption process.

Effect of Ionic Strength on the GOx Adsorption.

Figure 6:
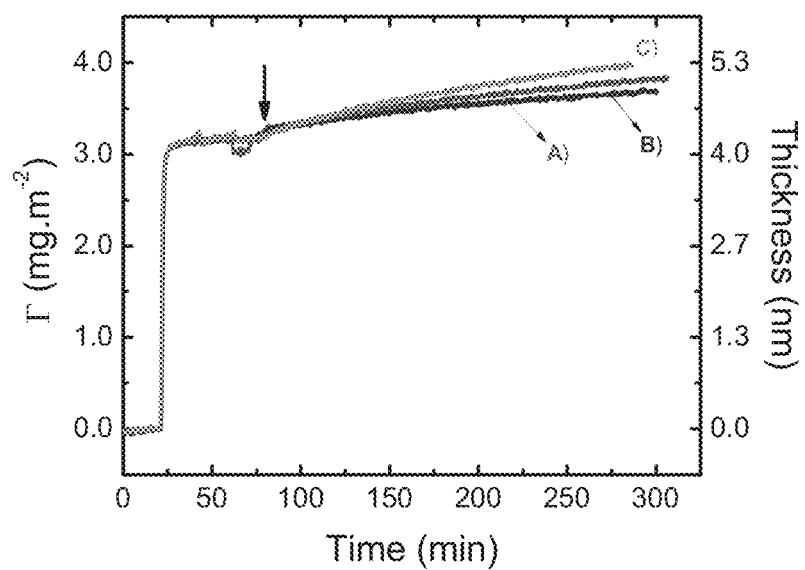
FIG. 6. Adsorption of 0.50 mg·mL$^{-1}$ GOx onto GOx/OTCE substrate at +800 mV in citrate buffer pH=4.2 with 100 mmol·L$^{-1}$ NaCl (A), 25 mmol·L$^{-1}$ NaCl (B), and no NaCl (C). The experiments were performed at a flow rate of 1 mL·min$^{-1}$. The arrow shows the time which the external potential was applied.

With the aim of studying the contribution of electrostatic interactions on the adsorption process assisted by the potential applied, the effect of ionic strength was investigated. For these experiments, a monolayer of GOx was first adsorbed (10 mmol·L$^{-1}$ citrate, pH=4.2, 0.50 mg·mL$^{-1}$ GOx, 40 min) on the OTCE at OCP. Next, the impinging solution was switched to a solution containing the selected concentration of NaCl (10 mmol·L$^{-1}$ citrate buffer, pH=4.2, 0.50 mg·mL$^{-1}$ GOx) for 20 min. Finally, the potential was changed from OCP to +800 mV to induce the enzyme accumulation on the surface. The results are shown in FIG. 6.

As it can be observed, increases in the ionic strength produced systematic decreases in the adsorption of GOx induced by the potential applied. Even though only slight differences in the final adsorbed amount were observed, the ionic strength seems to affect more significantly the initial stage of the secondary adsorption process ($d\Gamma/dt_2$). As it was described in a paper (T. E. Benavidez, C. D. Garcia, Langmuir 29 (2013) 14154), these results can be explained by considering that the potential applied can polarize the substrate (GOx/OTCE) and induce the polarization of the incoming proteins. When this happens, a secondary adsorption process is observed yielding to the accumulation of the proteins onto the substrate. Increasing the ionic strength of the environment can shield the effect of the potential and therefore decrease the probability for the incoming proteins to become polarized. More importantly, these experiments support the hypothesis that the polarization of the incoming proteins plays a fundamental role on the secondary adsorption process, that cannot be attributed to conventional interactions described for systems at open-circuit potential.

Enzymatic Activity of the GOx/OTCE Substrates.

In order to understand the effect of applied potential on the structural conformation of adsorbed GOx, the activity of the enzyme was measured immediately after the adsorption at the selected potentials. In order to obtain a uniform film of GOx on the OTCE, the OTCE/GOx substrates used for the experiments herein described were assembled in batch (by submerging the OTCE in a beaker containing 0.5 mg·mL$^{-1}$ GOx in citrate buffer and using an orbital shaker). Again, a monolayer of GOx was first adsorbed onto the OTCE (10 mmol·L$^{-1}$ citrate, pH=4.2) shaking the solution at 80 rpm for 60 min. After a spectroscopic scan was performed to verify the thickness of the protein layer (adsorbed at OCP), the GOx/OTCE substrate was immersed in a solution containing GOx and the potential was applied for 3 hours. Next, the thickness of GOx layer was measured by SE following the previously-described procedure. Finally, the GOx/OTCE substrate was placed in a quartz cell containing glucose, o-dianisidine, and horseradish peroxidase (HRP). The catalytic activity of the resulting substrate was evaluated by measuring the development of color (absorbance at 500 nm) using a spectrophotometer. The results are summarized in FIG. 7A, where the changes in the adsorbed amount of GOx at the selected potentials in regard to the OCP and the enzymatic activity of the substrates were plotted as a function of the potential applied during the secondary adsorption process. Before turning to the data analysis, it is important to highlight that the experimental data obtained in batch showed not only more dispersion but also slightly higher values in the adsorbed amount (and thickness) respect to dynamic experiments, especially when the enzyme adsorption was assisted by potential. However, the adsorption of GOx maintained the same trend and behavior in both cases allowing the comparison of the results.

As it can be observed, a correlation between the change in the adsorbed amount ($\Delta\Gamma$) of GOx and the enzymatic activity was obtained at potentials≤+800 mV. Within this range, changes in the adsorbed amount can be correlated with the catalytic activity of the resulting substrate. In line with the results presented in FIG. 3, larger amounts of GOx could be adsorbed onto the OTCE when potentials above +800 mV were applied on the electrode. However, despite the increasing amounts of GOx accumulated on the surface, applying potentials above +800 mV yielded significantly lower enzymatic activities (see FIG. 7B). This findings suggest that the potential applied to the substrate to induce the accumulation of the enzyme, could also have negative effects due to the electrochemical degradation of the enzyme. In order to confirm this hypothesis, GOx/OTCE substrates prepared with layers of GOx adsorbed at different potentials were investigated using cyclic voltammetry. According to these results, a well-defined anodic peak was obtained at +850 mV when the secondary enzyme adsorption process was performed at either OCP or +500 mV (see trace A in FIG. 7C). This process was attributed to the irreversible oxidation of the GOx layer adsorbed onto the OTCE. As the substrates were exposed to higher potential values (required to induce the secondary adsorption process), gradual decreases in the peak current were obtained (see trace B in FIG. 7C), making this peak non-evident when +950 mV were applied (see trace C in FIG. 7C). In other words, potential values above +800 mV were able to oxidize residues in the layer of enzyme adsorbed on the OTCE, and negatively affect its catalytic activity. These experiments demonstrate that while the potential applied to the electrode surface can promote the adsorption process of GOx via the polarization effect, potentials applied can also irreversibly oxidize the layer of adsorbed proteins, resulting in significant decreases in the catalytic activity. It is also important to point out that slight improvements in the overall activity of the resulting composite were obtained (FIG. 7B). This finding suggests that conformation of the enzyme adsorbed upon the application of an electric field could be different from the one obtained at OCP.

This Example described results related to the adsorption of GOx onto OTCE as a function of the potential applied to the substrate, and are complemented by measurements of the catalytic activity as well as molecular dynamic simulations. The results demonstrated that larger potential values can increase the adsorbed amount ($\Gamma$) of the enzyme on the OTCE, and that under moderate conditions (E<+850 mV), GOx was able to retain its enzymatic activity. On the other side, potential values higher than +850 mV can induce not only the accumulation of larger amounts of enzyme, but also a secondary electrochemical process that irreversibly affects the protein structure and therefore its enzymatic activity. In summary, we believe that these experiments can provide rational guidelines to take advantage of the polarization effect and produce biosensors with a catalytic activity that is significantly better than that obtained at open-circuit potential.

Example 3

Improving Cell Adhesion to Carbon-Based Substrates by the Adsorption of Collagen Under Potentiostatic Conditions Proteins adsorbed on material surfaces mediate and modulate subsequent interactions of anchorage-dependent cells (i.e., those present in most mammalian tissues). Since cell adhesion and functions pertinent to new tissue formation are thus affected, understanding and controlling protein adsorption on material surfaces prior to subsequent cell interaction is critical for the success of tissue engineering and regeneration applications, but remains partially understood. The present research was motivated by this need and inspired by recent findings that applied electrical potential results in an increase of protein adsorption onto nanostructured carbon films. (Benavidez T E, Garcia C D. Potential-Assisted Adsorption of Proteins to Optically-Transparent Carbon Electrodes. Langmuir. 2013; 29: 14154-62. PMCID: PMC3601777; Benavidez T E, Torrente D, Marucho M, Garcia C D. Adsorption and Catalytic Activity of Glucose Oxidase Accumulated on OTCE upon the Application of External Potential. J Colloid Interface Sci. 2014: in press.) The hypothesis of this in vitro study was that substrate exposure to an electrochemical potential would promote adsorption of proteins, therefore providing conditions which modulate subsequent cell adhesion, a requirement for anchorage-dependent cells survival and function. For this purpose, Rat-tail, Type I collagen (0.1 mg/mL in 20 mM acetic acid; pH 3.2) was adsorbed on the surface of optically-transparent carbon (OTC) using electrochemical adsorption under either +400 mV or +800 mV, at room temperature, for 3 hours. Subsequently, adult, human, mesenchymal stem cells (hMSCs) in hMSC basal medium (without serum) were seeded on the surface of each substrate and allowed to adhere in the absence of electrical potential, in a humidified, 37° C. 5% $CO_2$/95% air environment for 2 hours. Then, the adherent cells were fixed, stained, visualized, and counted. The data of hMSC adhesion were expressed as cells/cm$^2$ and compared to the respective controls. Controls were hMSCs seeded in parallel on either (1) tissue culture polystyrene (non-conductive substrate), (2) OTC without exposure to the electrical potential, or (3) pre-adsorbed protein on OTC without exposure to the electrical potential. The controls were maintained under similar conditions and analyzed using the aforementioned techniques. Increased hMSC adhesion was observed when Type I collagen was pre-adsorbed on OTC substrates under 800 mV. hMSC adhesion was similar on all OTC controls tested and on substrates with pre-adsorbed collagen under 400 mV of electric potential.

Experimental Design

Reagents and Solutions.

All aqueous solutions were prepared using 18 MΩ·cm water (NANOpure Diamond, Barnstead; Dubuque, IA) and analytical reagent grade chemicals. Additionally, the protein solutions were filtered through 0.2 μm poly(tetrafluoroethylene) membrane (PTFE, VWR International; Radnor, PA) before to be used in order to remove any aggregates. Sodium hydroxide, and sodium phosphate monobasic anhydrous were obtained from Fisher Scientific (Fair Lawn, NJ). The pH of different solutions was adjusted using 1 mol·L$^{-1}$ NaOH and measured using a glass electrode and a digital pH meter (Orion 420A+, Thermo; Waltham, MA). The 0.10 mg·mL$^{-1}$ protein solutions were prepared by dissolving a known amount of each protein in 10 mmol·L$^{-1}$ buffer solution. The optically transparent carbon (OTC) films were prepared by pyrolysis of AZ P4330-RS Photoresist obtained from AZ Electronic Materials USA Corp. (Somerville, NJ). The commercial photoresist was diluted to 60% v/v of the as-received material with propylene glycol monomethyl ether acetate (PGMEA 99%, Alfa Aesar; Ward Hill, MA).

Substrates.

Silica wafers coated with thin optically transparent carbon films (Si/SiO$_2$/OTC) were used as conductive platforms to adsorb the selected proteins and investigate the effect of the potential applied. The OTC were obtained following the procedure described in a previous paper. (Benavidez T E, Garcia C D. Spectroscopic and Electrochemical Characterization of Nanostructured Optically-Transparent Carbon Electrodes. Electrophoresis. 2013; 34:1998-2006. PMCID: PMC3860877.) Concisely, standard <111> silicon wafers (Si/SiO$_2$, Sumco; Phoenix, AZ) were first scored using a computer-controlled engraver (Gravograph IS400, Gravotech; Duluth, GA). The process defined pieces of 1 cm in width and 3 cm in length that were then manually cut and cleaned in piranha solution (30% hydrogen peroxide and 70% sulfuric acid) at 90° C. for 30 min. After thorough rinsing with water, the substrates were immersed and stored in ultrapure water until use. Subsequently the clean wafers were dried at 80° C. for 30 min; a thin layer of photoresist was deposited onto the silicon wafers using a spin coater (Laurell, Model WS-400-6NPP; North Wales, PA). Next, the photoresist-coated substrates were heated at 110° C. for 60 s in a convection oven to evaporate the solvent and then transferred to a tube furnace (Thermolyne F21135, Barnstead International; Dubuque, IA) for pyrolysis. The carbonization step began by flushing the system at 1 L·min$^{-1}$ with forming gas (95% Ar+5% H$_2$, v/v) for 5 min. Next, the temperature was increased to 1000° C. 20° C.·min$^{-1}$. After pyrolysis during 1 h, the system was allowed to cool to room temperature. Finally, the samples were stored in a Petri dish for a minimum of 3 days to complete the spontaneous surface oxidation.

Cyclic Voltammetry.

Cyclic voltammetry (CV) was used to study the electrochemical response of collagen on the OTC, and to define the working potential range for the adsorption studies. (Guiseppi-Elie A, Lei C, Baughman R H. Direct electron transfer of glucose oxidase on carbon nanotubes. Nanotechnology. 2002; 13(5):559.) In addition, the electrochemical behavior of the collagen/OTC substrates was also investigated by CV after adsorption of the enzyme at the selected potential (OCP, +400, +800 mV, and +1500 mV). In all cases, experiments were performed in 10 mmol·L$^{-1}$ citrate buffer using a CHI812 Electrochemical Analyzer (CH Instruments, Inc.; Austin, TX), silver/silver chloride (Ag|AgCl|KCl$_{sat}$) reference electrode, and a platinum wire as the counter electrode.

Spectroscopic Ellipsometry.

Adsorption experiments were performed using a variable angle spectroscopic ellipsometer (WVASE, J. A. Woollam Co.; Lincoln, NE) following a procedure described elsewhere. (Mora M F, Reza Nejadnik M, Baylon-Cardiel J L., Giacomelli C E, Garcia C D. Determination of a setup correction function to obtain adsorption kinetic data at stagnation point flow conditions. J Colloid Interface Sci. 2010; 346(1):208-15. PMCID: PMC2892644; Nejadnik M R, Francis L, Garcia C D. Nanoscale Scaffolds of Carbon Nanotubes for Immobilization of Glucose Oxidase. Electroanalysis. 2011; 23(6): 1462-9. PMCID: PMC3380380; Fujiwara H. Spectroscopic ellipsometry. Principles and applications. West Sussex, England: J. Wiley & Sons; 2007.) The basis of SE is the measurement of change in the reflectance and phase difference between the parallel ($R_P$) and perpendicular ($R_S$) components of a polarized light beam upon reflection from a surface. The intensity ratio of $R_P$ and $R_S$ can be related to the ellipsometric angles ($\Delta$ and $\Psi$) using the following equation:

$$\tan(\Psi)e^{i\Delta} = \frac{R_P}{R_S}$$

The amplitude ratio ($\Delta$) and phase difference ($\Psi$) as function of wavelength or time were modeled using the WVASE software package (J. A. Woollam Co.; Lincoln, NE) and the mean square error (MSE, calculated by a built-in function in WVASE) was used to quantify the difference between the experimental and model-generated data. In agreement with previous reports, MSE<15 were considered acceptable. (Mora M F, Reza Nejadnik M, Baylon-Cardiel J L, Giacomelli C E, Garcia C D. Determination of a setup correction function to obtain adsorption kinetic data at stagnation point flow conditions. J Colloid Interface Sci. 2010; 346(1): 208-15. PMCID: PMC2892644; Nejadnik M R, Francis L, Garcia C D. Nanoscale Scaffolds of Carbon Nanotubes for Immobilization of Glucose Oxidase. Electroanalysis. 2011; 23(6): 1462-9. PMCID: PMC3380380.) The ellipsometric measurements were interpreted using an optical model previously developed in our lab and presented in preceding papers. (Benavidez T E, Garcia C D. Potential-Assisted Adsorption of Proteins to Optically-Transparent Carbon Electrodes, Langmuir. 2013; 29:14154-62. PMCID: PMC3601777; Benavidez T E, Torrente D, Marucho M, Garcia C D. Adsorption and Catalytic Activity of Glucose Oxidase Accumulated on OTCE upon the Application of External Potential. J Colloid Interface Sci. 2014: in press.) The ellipsometric model describes the microstructure of the samples in terms of the refractive index (n), extinction coefficient (k), and thickness (d). Consequently, five uniaxial layers with optical axes parallel to the surface substrate were considered in this optical model. Because the experiments were performed in aqueous media, the optical properties of water were also contemplated. First, the dielectric function of Si (bulk, d=1 mm) and $SiO_2$ (d=2.1±0.5 nm) were used to describe the optical behavior of silica wafer. Next, the optical constants of carbon (Benavidez T E, Garcia C D. Spectroscopic and Electrochemical Characterization of Nanostructured Optically-Transparent Carbon Electrodes. Electrophoresis. 2013; 34:1998-2006. PMCID: PMC3860877) were used to define the ellipsometric response of the OTC (d=19.6±0.7 nm). Then, a void layer bearing in mind nano-bubbles (Hampton Mass., Nguyen A V. Nanobubbles and the nanobubble bridging capillary force. Adv Colloid Interface Sci. 2010; 154(1-2):30-55; Tyrrell J W G, Attard P. Images of Nanobubbles on Hydrophobic Surfaces and Their Interactions. Phys Rev Lett. 2001; 87(17):176104; Borkent B M, Dammer S M, Schönherr H, Vancso G J, Lohse D. Superstability of Surface Nanobubbles. Phys Rev Lett. 2007; 98(20):204502; Craig V S J. Very small bubbles at surfaces—the nanobubble puzzle. Soft Matter. 2011; 7(1):40-8) formed on the hydrophobic and rough surface of the OTC was also incorporated to improve the optical model. Lastly, the protein layer adsorbed on the OTC was described flawlessly using a Cauchy function.

Dynamic adsorption experiments were performed in a modified electrochemical cell (Mora M F, Reza Nejadnik M, Baylon-Cardiel J L, Giacomelli C E, Garcia C D. Determination of a setup correction function to obtain adsorption kinetic data at stagnation point flow conditions. J Colloid Interface Sci. 2010; 346(1):208-15. PMCID: PMC2892644) (J. A. Woollam Co.; Lincoln, NE) mounted directly on the vertical base of the ellipsometer, with an incident angle of 70°. Before the adsorption of selected protein on the substrate, the thickness of the OTC was always measured by placing the substrate in the ellipsometry cell and performing a spectroscopic scan from 300 to 1000 nm (with 10 nm step) using 10 mmol·L$^{-1}$ buffer solution as the ambient medium. Then, the adsorption experiment was started recording a baseline of the bare OTC at open circuit potential (OCP, the potential at which no current flows through the cell) while buffer solution was pumped inside the cell at a rate of 1 mL·min$^{-1}$. After 20 min of baseline, the protein solution was injected to adsorb a monolayer on the OTC at OCP. As a result, an initial fast process followed by a slower one was always observed. When a plateau in the signal was observed, the selected potential (+400 mV, +800 mV, or +1500 mV) was applied and kept until the end of the experiment. The change of potential was carried out employing a CHI812B Electrochemical Analyzer (CH Instrument, Inc.; Austin, TX), a silver/silver chloride (Ag|AgCl|KCl$_{sat}$) reference electrode, and a platinum wire as the counter electrode. Lastly, a spectroscopic scan was performed to obtain the thickness of the protein layer after the adsorption assisted by potential. The procedure described above provided the data to calculate the thickness of the OTC, the protein layer, and the adsorbed amount of collagen on the thin carbon electrodes.

Adult Human Mesenchymal Stem Cells and Cell Culture.

Frozen, adult, human, mesenchymal stem cells (hMSCs) were obtained commercially and characterized by the vendor (Lonza Walkersville, Inc). These cells were used in the present study without any further characterization. Before culture, the hMSCs in small aliquots were kept frozen at −200° C. For passaging, the cells were treated with trypsin/EDTA obtained from, and according to protocols provided by, the vendor (Lonza Walkersville, Inc). hMSCs were cultured under standard cell culture conditions (that is, a sterile, humidified, 37° C., 5% $CO_2$/95% air environment) in mesenchymal stem cell growth medium (consisting of mesenchymal stem cell basal-medium supplemented with serum, L-glutamine, and gentamicin/amphotericin-B). The concentrations of all supplements in this medium were considered proprietary information and were not disclosed by the vendor (Lonza Walkersville, Inc). Cells passage numbers 3-5 were used for all experiments.

Adult Human Mesenchymal Stem Cell Adhesion on Optically Transparent Carbon Substrates.

Rat-tail, Type I collagen (0.1 mg/mL in 20 mM acetic acid; pH 3.2) was adsorbed on the surface of optically-transparent carbon (OTC) substrates using electrochemical adsorption under either 0.4, 0.8 or 1.5 volts (vs Ag/AgCl/KCl$_{sat}$), at room temperature, for 3 hours. Subsequently, adult, human, mesenchymal stem cells (hMSCs) in hMSC basal medium (without serum) were seeded at 2,500 cells/cm$^2$ on the surface of each substrate sample and allowed to adhere in a humidified, 37° C., 5% $CO_2$/95% air environment for 2 hours. At that time point, the adherent hMSCs were fixed and their nuclei were stained using 4', 6-diamidino-2-phenylindole (DAPI). The stained hMSCs (mononuclear cells) were visualized using fluorescent microscopy (358 nm excitation; 461 nm emission), and the adherent cells on five, separate, randomly-chosen fields per substrate sample were photographed manually counted in situ, averaged, and reported as "cells per cm$^2$ substrate surface area". The data of hMSC adhesion was compared to results obtained from the respective controls. Controls were hMSCs seeded in parallel on (1) OTC substrates without exposure to the electrical potential, (2) OTC substrates with pre-adsorbed protein without exposure to the electrical potential, and (3) tissue culture polystyrene (non-conductive substrate); these controls were maintained under similar experimental conditions and analyzed using the aforementioned techniques. All hMSC adhesion experiments were run m duplicates per substrate type tested and repeated at three separate occasions.

Statistical Analysis.

All numerical data were reported as average±standard error of the mean (SEM) and were analyzed using ANOVA and commercially available software. P-values less than 0.05 were considered significant.

Results

Effect of the Concentration of Collagen.

Figure 15:
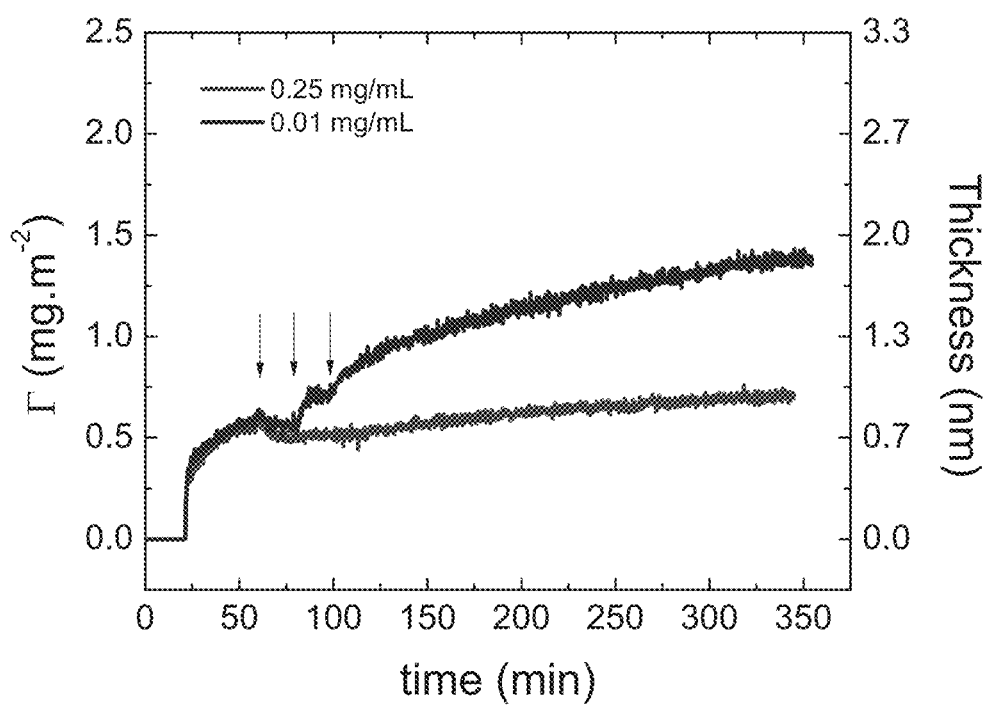
FIG. 15. Effect of collagen concentration on adsorption at +800 mV of: A) 0.01, B) 0.25, mg·mL$^{-1}$ after a layer (0.8 nm) was adsorbed onto OTC at OCP. The arrows show the time at which the solution was switched and the external potential was applied.

The effect of collagen concentration was investigated in the 0.01-0.25 mg·mL$^{-1}$ range. Once again, the experiment was performed by first adsorbing a monolayer of collagen (at pH=3.2, 40 min) on the bare OTC at OCP. Next, the impinging solution (containing collagen at the selected concentration) was pumped into the cell for 20 min to evaluate the stability of adsorbed protein layer and to establish the baseline. Then, +800 mV were applied and the experiment followed for at least another 220 min. FIG. 15 summarizes the results of the dynamic adsorption experiments (adsorbed amount and layer thickness obtained as a function of time). As it can be observed, the accumulation of protein molecules onto the collagen/OTC substrates was only observed upon the application of the potential to the electrode (at t=80 min). Additionally, only a slight amount of collagen was desorbed when the concentration decreased to 0.01 mg·mL$^{-1}$. Consequently, the experimental results suggest that the attachment of collagen to the polarized surface was controlled by the number of protein molecules incoming to the substrate. Considering the polarization of protein molecules as one of the most relevant driving forces of protein adsorption induced by potential, the increase of the number of collagen molecules impinging on the polarized substrate increased the subsequent protein adsorption.

Effect of Potential on the Adsorption of Collagen.

Figure 16:
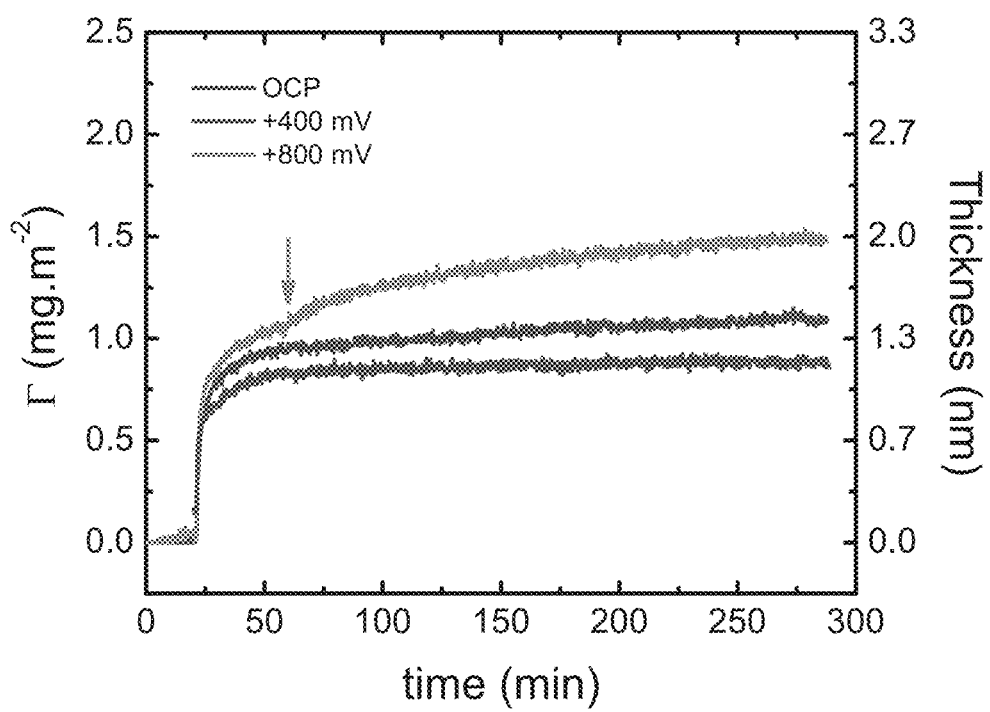
FIG. 16. Effect of applied potential on the adsorption kinetic of 0.10 mg·mL$^{-1}$ collagen at the isoelectric point, after adsorption of a collagen layer onto OTC at OCP. The arrow shows the time which the external potential was applied.

In order to study the effect of the applied potential, adsorption experiments were performed by recording the baseline (bare OTC) and then allowing collagen to adsorb on the surface of the OTC at OCP. In agreement with reports, these values are in line with the formation of an entangled layer of protein on the surface of the OTC with predominant side-on orientation. When stable readings for the ellipsometric angles were obtained (typically around 60 min), the selected potential (OCP, +400, or +800 mV) was applied and maintained until the end of the experiment. FIG. 16 shows representative examples of the results obtained during the adsorption of the first layer of collagen (at OCP) and the second my adsorption process, induced by the application of the external potential (marked as ↓). In all cases, the secondary adsorption process proceed as a fast growth process in the protein layer within the first 15 sec upon the application of the potential (dΓ/dt$_1$), followed by a much slower one (dΓ/dt$_2$) that remained almost constant until the end of the experiment.

Figure 17:
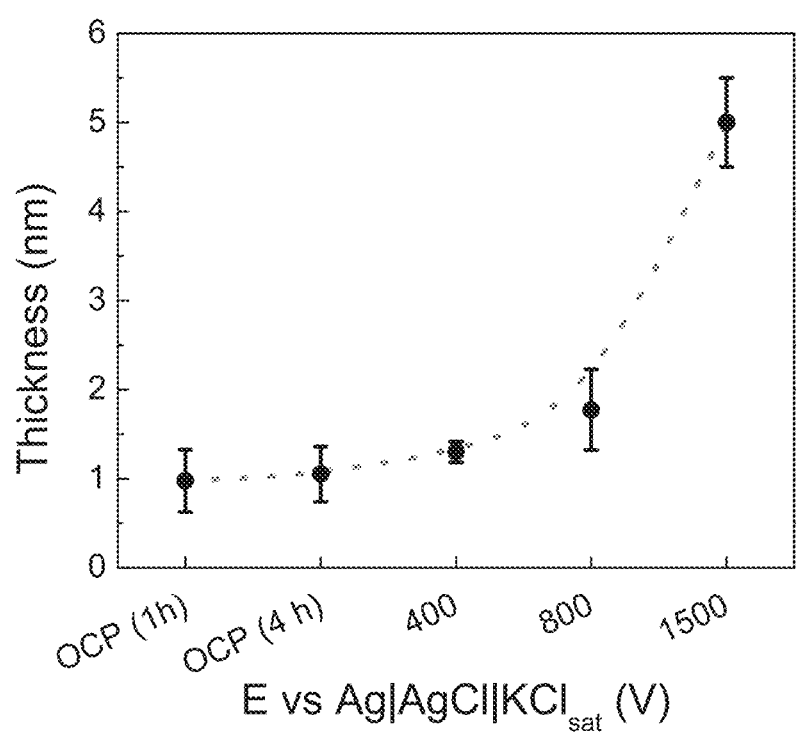
FIG. 17. Average final thickness (after 280 min) of the protein layer (obtained with 5 different electrodes) as a function of the potential applied to the electrode surface. The error bars represent the standard deviation obtained from at least 3 independent measurements.

Before turning to the discussion is important to point out that slight differences have been observed with different OTC substrates. Therefore, rather than focusing on the exact values of each experiment, we are considering the trend observed in each experiment. As it can be observed, no significant differences (with respect to the values obtained at OCP) were found in the adsorbed amount of collagen when the OTC potential was changed to from OCP to +400 mV However, considerable increases in thickness (and adsorbed amount of collagen) were obtained when the imposed potential was fixed at +800 mV. FIG. 17 summarizes the findings obtained with multiple electrodes (n=5) and shows that beyond the expected variability, there is a clear relationship between the adsorbed amount and the potential applied.

Effect of Oxidation.

Figure 18:
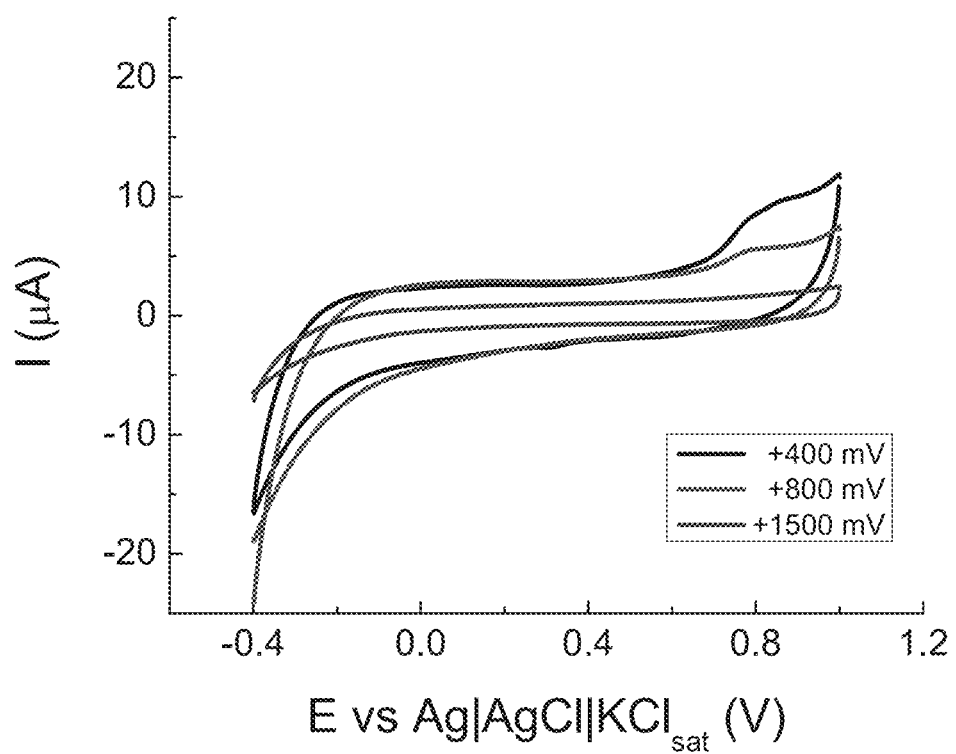
FIG. 18. Potentiodynamic I/E curves obtained with substrates prepared by the adsorption of collagen at the OCP and the subsequent secondary adsorption process at +400 mV, +800 mV, or +1500 mV.

One of the most important parameters to define is the potential to be applied to the surface. Although experiments were performed at +800 mV (based on results recently published by our group), we believe this should be further investigated. As it can be observed in FIG. 18, significantly different results were obtained for the collagen/OTC substrate prepared under +400, +800, and +1500 mV. We believe these differences can be attributed to the oxidation of functional groups on the protein, during the adsorption process. As it can be observed, the substrate coated with protein adsorbed at +400 mV, yielded a large oxidation peak at approximately +825 mV. This oxidation peak decreased (and then disappeared) when the substrate was adsorbed at +800 mV or +1500 mV, respectively.

These results highlight the importance of performing preliminary voltammetry experiments to stricke a balance between the adsorbed amount and the oxidation of the protein at the electrode surface.

Cell Adhesion.

In order to understand the biological effects of performing electrical stimulation of the adsorption process, our group investigated the adhesion of hMSC onto the selected substrates. Results shown in FIG. 19 correspond to averages obtained in three separate experiments, and using different batches of supplies. Control experiments (data not shown) were performed using tissue-culture plates processed with collagen and with serum.

Figure 19:
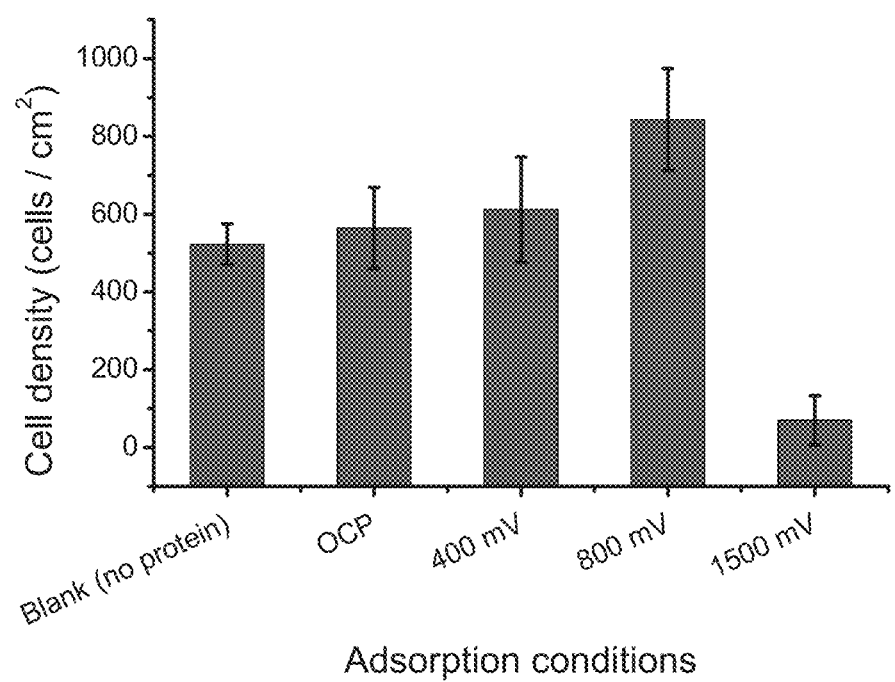
FIG. 19. Adhesion of hMSC to OTC substrates without collagen (blank), with collagen in the absence of external potential (OCP), with a secondary layer of collagen adsorved at +400 mV, with a secondary layer of collagen adsorved at +800 mV, and with a secondary layer of collagen adsorved at +1500 mV.

As it was previously discussed the application of potential (+400 mV and +800 mV) induced the accumulation of collagen via a secondary adsorption process not observed at open circuit potentials. As shown in FIG. 19, these increases in the adsorbed amount are correlated with an increase in the number of cells attached to the substrates. These results can be attributed to the increase in the surface coverage and the subsequent increase in the density of the binding domains. On the other side when the substrates were prepared by the application of +1500 mV (and despite promoting the formation of the thickest layer of collagen) a significantly lower number of cells were attached. Based on the results described in FIG. 18, these results can be explained by considering that the protein adsorbed under these conditions was oxidized and is no longer biologically functional. These results are important because they demonstrate the role of the applied potential in the balance between the accumulation of proteins and the biological activity of the resulting layer.

Figure 20:
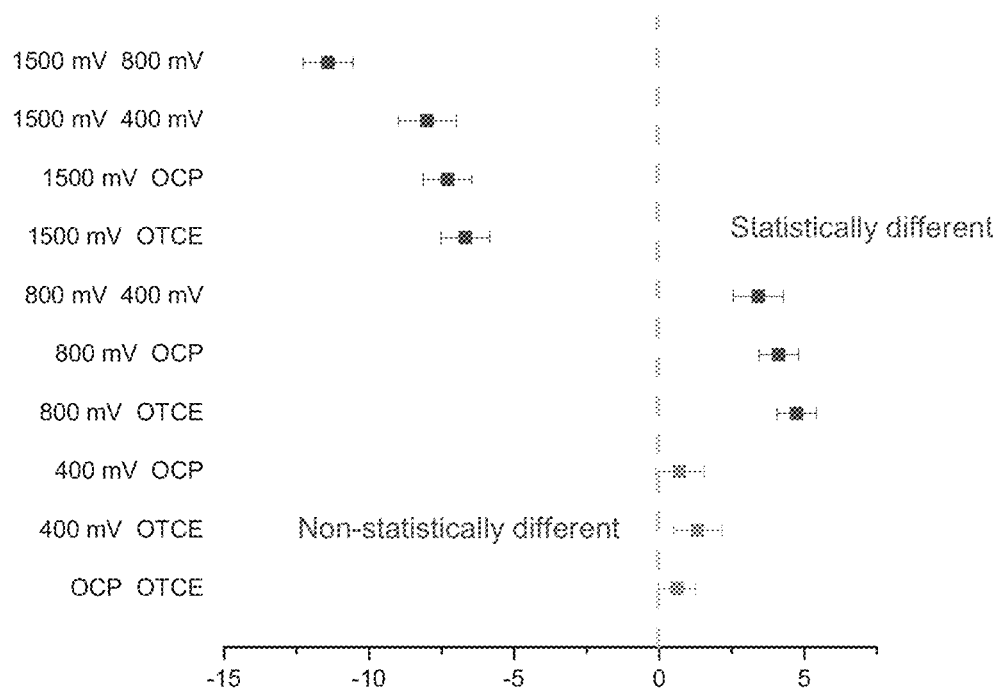
FIG. 20. Result of the ANOVA analysis (paired) comparing the cell density obtained for substrates coated with a layer of collagen adsorbed without potential (OCP) and substrates coated with a secondary layer of protein adsorbed under electrical stimulation at the corresponding potential values.

In order to verify the validity of the preliminary conclusions extracted from FIG. 19, a statistical analysis (ANOVA) was performed to compare the differences observed in each group. The results are summarized in FIG. 20. As it can be observed, no statistical difference was observed between the blank substrate (plain OTC with no collagen), the substrate prepared at open circuit potential (OCP), and the substrate prepared at +400 mv. Although slight differences were observed (FIG. 19), the variance between the populations are shielding the statistical-significance of such findings. On the other side, the ANOVA analysis performed for all other comparisons, verified that results obtained with substrates prepared at either +800 mV or +1500 mV were statistically different from the controls.

Conclusions

The results herein presented support the possibility to induce the secondary adsorption process in collagen. This secondary adsorption process was attributed to the polarization of the incoming protein molecules and does not depend on the traditional driving forces (hydrophobic or electrostatic) for the adsorption mechanism. Results also show that the amount of protein accumulated on the surface of the OTC is a function of the potential applied and that the higher the potential the higher the adsorbed amount. However, the application of higher potential values (+1500 mV) can also induce oxidative damage on the proteins and negatively impact their biological function.

Example 4

Adsorption of "Soft" and "Hard" Proteins onto OTCEs under the Influence of an External Electric Field The adsorption behavior of "hard" and "soft" proteins under the effect of an external electric field has been investigated by Spectroscopic Ellipsometry and Molecular Dynamic (MD) simulations. Optically transparent carbon electrodes (OTCE) were used as conductive substrates. Lysozyme (LSZ) and ribonuclease A (RNase A) were selected as representative "hard" proteins even as myoglobin (Mb), αlactalbumin (α-Lac), bovine serum albumin (BSA), glucose oxidase (GOx), and immunoglobulin G (IgG) were designated to represent the "soft" proteins. The experimental results revealed a high sensibility of "hard" proteins to the applied potential. That performance on the adsorption process was attributed to the intrinsic polarizability of the protein, the probability of attachment, the rearrangement of the protein monolayer by effect of the applied potential, and the shielding effect of the adsorbed protein film to the imposed electric field. Moreover, the DM simulations made evident to consider the importance of the solvent accessible surface area (SASA) as a key factor in the protein adsorption process.

1. Introduction

Protein adsorption is a spontaneous phenomenon that occurs when a solid surface is placed in contact with a protein solution.[1] In view of that, the adsorption process keeps on according to the physicochemical characteristics not only the protein (size, flexibility, and charge) but also the surface substrate (surface energy, charge, and morphology) .[2,3] In effect, the studies of protein adsorption have been generally carried out modifying the media conditions (solvent, pH, ionic strength, and temperature) in order to investigate the changes in the interfacial properties of the protein molecules as well as the substrate.[4-6] During the adsorption process, different steps which occur on different time-scales are involved in the attachment of the protein molecules onto the solid surface.[7] At the start, the protein molecules diffuse from the bulk of the solution to the interface. Then, the attachment of proteins takes place on the solid surface followed by the relaxation of the molecules adsorbed a moment ago; and the end, the proteins desorb from the interface and subsequently return to the bulk.

Additionally, the internal stability of the protein also plays an important role in the adsorption behavior so it could be considered as an extra variable of study to be taken into account. So much so that, W. Norde[4,8] was who introduced the widely accepted classification of proteins between the concepts of "hard" and "soft" by considering the structural stability mentioned above. The so-called "hard" proteins present a high internal stability which is given by a molecular structure with high-conformational entropy and consequently this kind of proteins undergo limited structural changes upon the adsorption. In contrast, "soft" proteins (with a low conformational entropy) adsorb onto solid surfaces driven by loss of the ordered molecular structure and results in an increase in the conformational entropy of the protein attached to the interface.

Furthermore, the variation of the interfacial potential has been also considered as another variable of the adsorbing surface when dealing with substrates constituted by conducting materials. Recently, we have demonstrated that the increase in the interfacial potential produced an increase in the accumulation of bovine serum albumin (BSA) onto optically transparent carbon electrodes (OTCE) attributed to a polarization effect induced in the protein molecules by imposing of the external electric field.[9] Because BSA does not have a specific biological activity that is be able to be measured, we have also reported the study of both properties, the adsorption behavior and the catalytic activity, of glucose oxidase (GOx) accumulated onto the OTCEs after the application of the electric field.[10] In this case, GOx also showed an increase of the adsorption on the electrode surface (in line with the BSA behavior), however the enzyme activity presented an unfortunate performance. Even though the adsorption of GOx was favored by increasing of the applied potential, the enzyme catalysis showed a maximum of activity when the accumulation of the enzyme was performed at +800 mV. In contrast, GOx exhibited a significant decrease in the catalytic activity at potential higher than +800 mV which was a consequence of an irreversible electrochemical reaction, noticed by cyclic voltammetry, in the enzymatic layer adsorbed on the OTCE. Thus, the chemical changes referred to the irreversible oxidation of cysteine, tryptophan, and tyrosine in GOx molecules were be able to produce the loss of the enzymatic activity.

The present article shows the study of protein adsorption assisted by potential (+800 mV) onto OTCEs and the relationship of the adsorption behavior of selected proteins (see Table 1) respect to their structural stability (defined as "soft" and "hard" proteins) and their physicochemical characteristics. Also, Dynamic Molecular (DM) simulations were performed to support the experimental findings.

TABLE 1

Physicochemical characteristics of Hard* and Soft proteins used in the present article.

| Proteins | Molar mass (kDa) | Size (nm³) | IEP (pH units) | Ref. |
|---|---|---|---|---|
| RNase A* | 13.7 | 3.8 × 2.8 × 2.2 | 9.20 | 11, 12 |
| α-LAC | 14.2 | 3.7 × 3.2 × 2.5 | 4.30 | 1, 12 |
| LSZ* | 14.5 | 4.5 × 3.0 × 3.0 | 11.00 | 1, 12 |
| Mb | 17.2 | 4.3 × 3.5 × 2.3 | 7.05 | 2, 13-15 |

TABLE 1-continued

Physicochemical characteristics of Hard* and Soft proteins used in the present article.

| Proteins | Molar mass (kDa) | Size (nm³) | IEP (pH units) | Ref. |
|---|---|---|---|---|
| BSA | 66.5 | 11.6 × 2.7 × 2.7 | 4.70 | 11, 16 |
| GOx | 160 | 8.0 × 7.0 × 5.5 | 4.20 | 17-20 |
| IgG | 160 | 14.2 × 8.5 × 3.8 | 7.00 | 21-23 |

Ribonuclease A (RNase A),
α-Lactalbumin (α-LAC),
Lysozyme (LSZ),
Myoglobin (Mb),
Bovine Serum Albumin (BSA),
Glucose Oxidase (GOx), and
Immunoglobulin G (IgG).

2. Experimental Design

Reagents and Solutions.

All aqueous solutions were prepared using 18 MΩ·cm water (NANOpure Diamond, Barnstead; Dubuque, IA) and analytical reagent grade chemicals. Additionally, the protein solutions were filtered through 0.2 µm poly(tetrafluoroethylene) membrane (PTFE, VWR International; Radnor, PA) before to be used in order to remove any aggregates. Glucose oxidase (GOx, Type II, from *Aspergillus niger*), Ribonuclease A (RNase A, from bovine pancreas), α-Lactalbumin (α-LAC, from bovine milk), Lysozyme (LSZ, from chicken egg white), Myoglobin (Mb, from equine skeletal muscle), Immunoglobulin G (IgG, from human serum), and suberic acid bis(N-hydroxy-succinimide ester) were obtained from Sigma-Aldrich (St. Louis, MO). Citric acid was acquired from Aldrich Chemical Company (Milwaukee, WI). N,N-Dimethylformamide (DMF, 99%) was purchase from Alfa Aesar (Ward Hill, MA). Bovine serum albumin (BSA), sodium hydroxide, and sodium phosphate monobasic anhydrous were obtained from Fisher Scientific (Fair Lawn, NJ). The pH of different solutions was adjusted using 1 mol·L$^{-1}$ NaOH and measured using a glass electrode and a digital pH meter (Orion 420A+, Thermo; Waltham, MA). The 0.10 mg·mL$^{-1}$ protein solutions were prepared by dissolving a known amount of each protein in 10 mmol·L$^{-1}$ buffer solution. The optically transparent carbon electrodes (OTCE) were prepared by pyrolysis of AZ P4330-RS Photoresist obtained from AZ Electronic Materials USA Corp. (Somerville, NJ). The commercial photoresist was diluted to 60% v/v of the as-received material with propylene glycol monomethyl ether acetate (PGMEA 99%, Alfa Aesar; Ward Hill, MA).

Substrates.

Silica wafers coated with thin optically transparent carbon films (Si/SiO$_2$/OTCE) were used as conductive platforms to adsorb the selected proteins and investigate the effect of the potential applied. The OTCEs were obtained following the procedure described in a previous paper.[24] Concisely, standard <111> silicon wafers (Si/SiO$_2$, Sumco; Phoenix, AZ) were first scored using a computer-controlled engraver (Gravograph IS400, Gravotech; Duluth, GA). The process defined pieces of 1 cm in width and 3 cm in length that were then manually cut and cleaned in piranha solution (30% hydrogen peroxide and 70% sulfuric acid) at 90° C. for 30 min. After thorough rinsing with water, the substrates were immersed and stored in ultrapure water until use. Subsequently the clean wafers were dried at 80° C. for 30 min; a thin layer of photoresist was deposited onto the silicon wafers using a spin coater (Laurell, Model WS-400-6NPP; North Wales, PA). Next, the photoresist-coated substrates were heated at 110° C. for 60 s in a convection oven to evaporate the solvent and then transferred to a tube furnace (Thermolyne F21135, Barnstead International; Dubuque, IA) for pyrolysis. The carbonization step began by flushing the system at 1 L·min$^{-1}$ with forming gas (95% Ar+5% H$_2$, v/v) for 5 min. Next, the temperature was increased to 1000° C. at 20° C.·min$^{-1}$. After pyrolysis during 1 h, the system was allowed to cool to room temperature. Finally, the samples were stored in a Petri dish for a minimum of 3 days to complete the spontaneous surface oxidation.

Spectroscopic Ellipsometry.

Adsorption experiments were performed using a variable angle spectroscopic ellipsometer (WVASE, J. A. Woollam Co.; Lincoln, NE) following a procedure described elsewhere.[25-27] The basis of SE is the measurement of change in the reflectance and phase difference between the parallel (R$_P$) and perpendicular (R$_S$) components of a polarized light beam upon reflection from a surface. The intensity ratio of R$_P$ and R$_S$ can be related to the ellipsometric angles (Ψ and Δ) using the following equation:

$$\tan(\Psi)e^{i\Delta} = \frac{R_p}{R_S}$$

The amplitude ratio (Ψ) and phase difference (Δ) as function of wavelength or time were modeled using the WVASE software package (J. A. Woollam Co.; Lincoln, NE) and the mean square error (MSE, calculated by a built-in function in WVASE) was used to quantify the difference between the experimental and model-generated data. In agreement with previous reports, MSE<15 were considered acceptable.[25,26] The ellipsometric measurements were interpreted using an optical model previously developed in our lab and presented in preceding papers.[9,24] The ellipsometric model describes the microstructure of the samples in terms of the refractive index (n), extinction coefficient (k), and thickness (d). Consequently, five uniaxial layers with optical axes parallel to the surface substrate were considered in this optical model. Because the experiments were performed in aqueous media, the optical properties of water were also contemplated. First, the dielectric function of Si (bulk, d=1 mm) and SiO$_2$ (d=2.1±0.5 nm) were used to describe the optical behavior of silica wafer. Next, the optical constants of carbon[24] were used to define the ellipsometric response of the OTCE (d=19.6±0.7 nm). Then, a void layer bearing in mind nanobubbles[28-31] formed on the hydrophobic and rough surface of the OTCE was also incorporated to improve the optical model. Lastly, the protein layer adsorbed on the OTCE was described flawlessly using a Cauchy function.

Dynamic adsorption experiments were performed in a modified electrochemical Cell[25] (J. A. Woollam Co.; Lincoln, NE) mounted directly on the vertical base of the ellipsometer, with an incident angle of 70°. Before the adsorption of selected protein on the substrate, the thickness of the OTCE was always measured by placing the substrate in the ellipsometry cell and performing a spectroscopic scan from 300 to 1000 nm (with 10 nm step) using 10 mmol·L$^{-1}$ buffer solution as the ambient medium. Then, the adsorption experiment was started recording a baseline of the bare OTCE at open circuit potential (OCP, the potential at which no current flows through the cell) while buffer solution was pumped inside the cell at a rate of 1 mL·min$^{-1}$. After 20 min of baseline, the protein solution was injected to adsorb a monolayer on the OTCE at OCP. As a result, an initial fast process followed by a slower one was always observed. When a plateau in the signal was observed, +800 mV were applied and kept until the end of the experiment. The change of potential was carried out employing a CHI812B Electrochemical Analyzer (CH Instrument, Inc.; Austin, TX), a silver/silver chloride (Ag|AgCl|KCl$_{sat}$) reference electrode, and a platinum wire as the counter electrode. Lastly, a spectroscopic scan was performed to obtain the thickness of the protein layer after the adsorption assisted by potential. The procedure described above provided the data to calculate the thickness of the OTCE, the protein layer, and the adsorbed amount of the selected proteins on the thin carbon electrodes.

Molecular Dynamics Simulations.

In order to describe the interaction between an external electric field and a single protein molecule, molecular dynamic (MD) simulations were performed using NAMD 2.9 package[32] with Amber force field 99SB.[33] To investigate the effect of the potential applied on "hard" and "soft" proteins, lysozyme (LSZ) and myoglobin (Mb) were selected respectively because they have similar molecular weight and protein dimensions (Table 1). The initial protein coordinates were taken from the Protein Data Bank (PDBID: 1 LYZ and 1 MBN, respectively). Before performing the simulation, the protein was solvated with water (TIP3[34]) and placed in the center of a cubic box of 11.5 nm×11.4 nm×10.6 nm. Additionally, the system was neutralized by the addition of NaCl. The MD simulations were run at the respective IEP (see Table 1) by protonation or deprotonating stages using classical continuum electrostatics available in H++.[35] In all cases, the systems were minimized and equilibrated until reaching the equilibrium state (~1 ns). Subsequently, the Molecular Dynamics production was performed in the NVT ensemble at 298 K (maintained constant using Langevin dynamics, with a damping coefficient of 5 ps$^{-1}$) using a time step of 2 fs, the SHAKE algorithm, and periodic boundary conditions. Also, the center of mass (COM) of the protein was fixed using the steered molecular dynamic (SMD) module to avoid displacement of the proteins during the simulation.[36] To end with the procedure, the external constant electric field was applied along the z direction for 40 ns using the following relationship:

$$E = \frac{V_m}{L_z}$$

where $V_m$ is the external electric potential and $L_z$ is the length of the system in the z direction. For these experiments, three different electric fields were run such as 0.075, 0.180, and 0.424 V·nm$^{-1}$ (that correspond to 800, 2000, and 4500 mV, respectively). As well, the control simulation was carried out using identical conditions but without the external electric field. As a final point, the simulation results were used to study the effect of the imposed electric field on the solvent accessible surface area (SASA) and the induced protein dipole moment.

On the other side, the protein-protein interactions were also considered to be studied by MD simulation and investigate the subsequent protein adsorption assisted by potential onto the protein monolayer previously adsorbed at OCP. In this case, the simulations were configured using the same conditions described above for the single protein molecule excepting that a new box dimensions (15.0 nm×14.5 nm×25.0 nm) and only the highest electric field (0.424 V·nm$^{-1}$) were used. To calculate the work required to form the Mb-Mb and LSZ-LSZ complexes, Steer Molecular Dynamic (SMD) simulations were used.[37] At the start, both proteins were set at a distance of 9 nm each other. Next, one of them was pulled toward the z direction coordinate of COM of the second one. That it is why the protein with the fixed COM simulates the protein adsorbed previously on the electrode. The optimal constant pulling velocity was found to be 0.2 nm·ns$^{-1}$ whereas an appropriate stiff spring approximation was obtained using a spring force of 5 kcal·mol$^{-1}$·nm$^2$.[37] The work calculated for this simulation was considered irreversible due to the different distribution of the reverse and forward pulling between both proteins. The work was calculated as a function of time (t) using the following expression:

$$W(t)_{A \to B} = v \int_0^t dt' f(t')$$

where v is the constant pulling velocity, dt' is the time step and f is the force done by the system.

Cross-Linking of BSA.

With the aim of investigate the BSA adsorption induced by potential and attempting to compare with a hard protein with similar dimensions, BSA molecules (a "soft" protein) were cross-linked with suberic acid bis(N-hydroxy-succinimide ester)[38] to obtain BSA molecules with a higher conformational rigidity. The cross-linker also known as disuccinimidyl subarate (DSS) is a water-insoluble homobifunctional cross-linker that reacts specifically with the primary amine of lysine residues to form stable amide bonds. Because it is insoluble in water, 2 mg of DSS were dissolve in 432 μL of DMF to obtain a concentration of 12.5 mmol·L$^{-1}$. Then, the cross-linker solution was added to the BSA solution previously prepared by dissolving 25 mg of the protein in 10 mmol·L$^{-1}$ phosphate buffer containing 150 mmol·L$^{-1}$ of NaCl at pH=7.8 as required by protocol. After shaking at 80 rpm for 30 min, the reaction mixture was placed in a dialysis tubing (12-14 kDa) and the ends were hold strongly using two tubing closers. Subsequently, the sample was immersed in 150 mL of 10 mmol·L$^{-1}$ citrate buffer at pH=4.7 contained in a beaker and incubated in a cold room for 24 hs. According to the dialysis protocol, the buffer solution was replaced each 4 hs.

Figure 21:
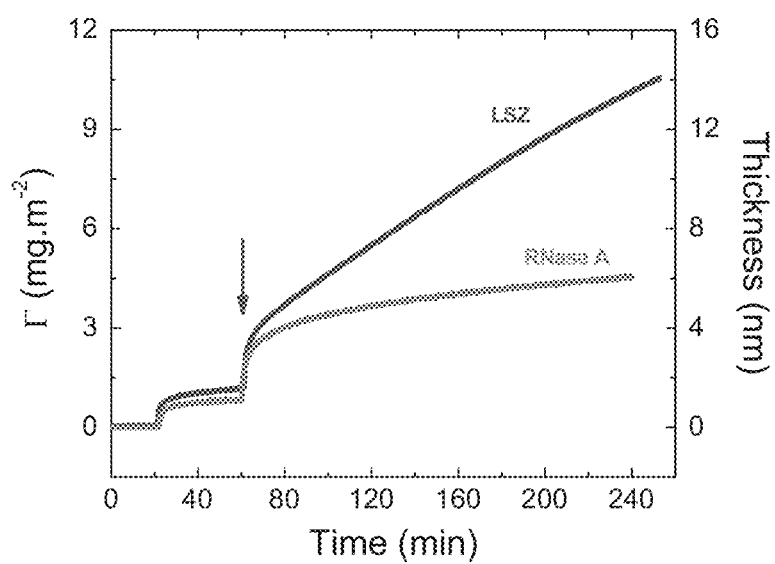
FIG. 21. Effect of applied potential on the adsorption kinetic of 0.10 mg·mL$^{-1}$ LSZ and RNase A after adsorption of the respective protein monolayer onto OTCE at OCP. Adsorption experiments were performed in 10 mmol·L$^{-1}$ buffer solution at the IEP of the respective enzyme and a flow rate of 1 mL·min$^{-1}$. The arrows show the time which the external potential was applied.

3. Results and Discussion 3.1 Effect of Applied Potential on the Adsorption of "Hard" Proteins In order to compare the adsorption behavior of structure-stable proteins with similar molecular dimensions, LSZ and RNase A (classified as "Hard" proteins)[8,12] were selected to perform the dynamic adsorption experiments onto OTCE under the induction of an electric field. The adsorption experiments were made up of three different steps (the baseline, the adsorption of a protein monolayer at OCP, and the changing of the interfacial potential) which were followed by SE. After a baseline of 20 min, a monolayer of protein was allowed to adsorb (10 mmol·L$^{-1}$ buffer solution containing 0.1 mg·mL$^{-1}$ of protein at the IEP) on the OTCE at OCP for 40 min. As a result, the adsorbed protein monolayers showed thickness values ($d_{RNase\ A}$=1.1±0.4 nm and $d_{LSZ}$=1.6±0.3 nm) lower than the molecular dimensions of the nominated enzymes possibly due to a protein layer not fully packed. Then, after constant readings were observed, the electrode potential was switched to +800 mV at t=60 min as shown in FIG. 21. Therefore, it was possible to detect three different changes in the protein adsorption process after switching the interfacial potential which were named as: $d\Gamma/dt_1$ (immediately after +800 mV were applied at t=60 min), $d\Gamma/dt_2$ (observed between t=100 min and t=150 min), and $d\Gamma/dt_3$ (obtained from t=200 min to t=240 min).

As can be noticed, in both cases the adsorption process displayed an important increase in the protein accumulation on the substrate surface as demonstrated the adsorption rate ($d\Gamma/dt_1$, RNase A=0.98±0.07 mg·m$^{-2}$·min$^{-1}$ and LSZ=1.3±0.2 mg·m$^{-2}$·min$^{-1}$) obtained immediately after the interfacial potential was changed to +800 mV at t=60 min. In addition, the experimental data suggest that a differential proneness to the imposed electric field came about in the subsequent protein attachment, being LSZ more susceptible to the applied potential than RNase A as make evident the $d\Gamma/dt_2$ and $d\Gamma/dt_3$ values presented in Table 2. Also, given the protein dimensions, the obtained results revealed that the accumulation of protein by effect of the applied potential produced enzymatic multilayers in both cases, with particular accent in the case of LSZ whose thickness reached a value of 13.9±0.3 nm (and $\Gamma$=10.4±0.2 mg·m$^{-2}$ at 250 min) which implies an increment between 3 and 4 times of the enzyme dimensions.

TABLE 2

Initial adsorption rate (obtained immediately after +800 mV were applied, $d\Gamma/dt_1$), and linear approximation of the second and third adsorption processes (calculated betweem 100-150 min, $d\Gamma/dt_2$, and 200-240 min, $d\Gamma/dt_3$, respectively)

| Proteins | $d\Gamma/dt_1$ (mg · m$^{-2}$ · min$^{-1}$) | $d\Gamma/dt_2$ (×10$^{-3}$ mg · m$^{-2}$ · min$^{-1}$) | $d\Gamma/dt_3$ (×10$^{-3}$ mg · m$^{-2}$ · min$^{-1}$) |
|---|---|---|---|
| RNase A | 0.98 ± 0.07 | 10.8 ± 0.1 | 5.7 ± 0.1 |
| LSZ | 1.3 ± 0.2 | 43.27 ± 0.05 | 34.32 ± 0.09 |
| Mb | −0.04 ± 0.02 | 5.70 ± 0.06 | 3.56 ± 0.07 |
| α-LAC | 0.21 ± 0.01 | 4.47 ± 0.08 | 2.9 ± 0.1 |
| BSA | 0.044 ± 0.007 | 3.34 ± 0.04 | 2.5 ± 0.1 |
| Cross-linked BSA | 28 ± 8 | 11.06 ± 0.05 | 9.7 ± 0.1 |
| IgG | 26 ± 4 | 15.30 ± 0.05 | 7.5 ± 0.1 |
| GOx | 13 ± 5 | 1.27 ± 0.04 | 0.72 ± 0.09 |

On the other side, the second process ($d\Gamma/dt_2$, see Table 2) showed significant differences in the adsorption behavior of the enzymes. Thus, the experimental results demonstrated an adsorption rate of 4 times higher in the case of LSZ respect to RNase A. Additionally, the experimental data proved a decrease of 50% approximately flanked by the last two adsorption rates in the case of RNase A ($d\Gamma/dt_2$ and $d\Gamma/dt_3$); signifying that the influence of the electric field was not able to promote the increase in the attachment of the enzyme molecules on the substrate surface. In consequence, the adsorption of RNase A presented an earlier decline during the adsorption experiments contrary to LSZ which showed a reduction nearby 20%. Accordingly, the experimental data suggest that a shielding effect of the protein film previously adsorbed on the OTCE and also a less polarization effect of the RNase A molecules could probably take place generating a deletion of the polarizing effect on the incoming enzyme molecules and consequently a decrease in the subsequent attachment of the proteins to the substrate. Although the differences observed between them, the adsorption behavior of those enzymes exhibited an instantaneous and fast adsorption rate ($d\Gamma/dt_1$) immediately after the changing of the interfacial potential to +800 mV which can be considered as the main distinction of the electric field effect on this group of proteins.

3.2 Effect of Applied Potential on the Adsorption of "Soft" Proteins

Figure 22:
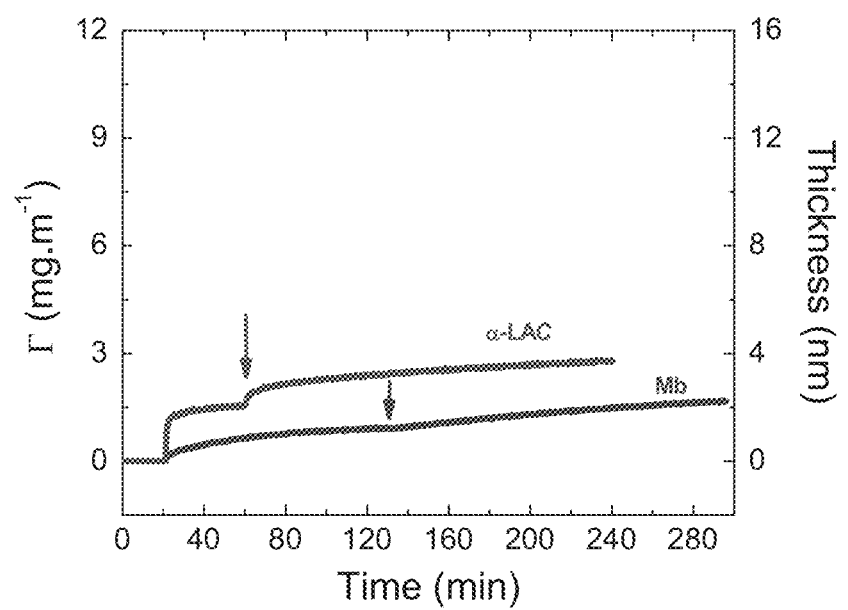
FIG. 22. Effect of applied potential on the adsorption kinetic of 0.10 mg·mL$^{-1}$ α-LAC and Mb after adsorption of the respective protein monolayer onto OTCE at OCP. Adsorption experiments were performed in 10 mmol·L$^{-1}$ buffer solution at IEP of the respective protein and a flow rate of 1 mL·min$^{-1}$. The arrows show the time which the external potential was applied.
Figure 23:
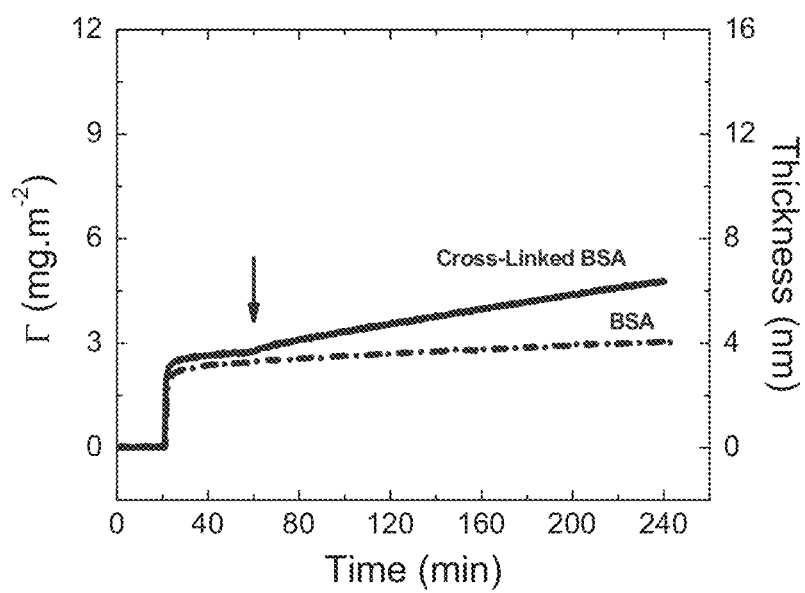
FIG. 23. Effect of the applied potential on the adsorption kinetic of 0.10 mg·mL$^{-1}$ BSA and BSA cross-linked with DSS after adsorption of the respective protein monolayer onto OTCE at OCP. All experiments were performed in 10 mmol·L$^{-1}$ citrate at IEP and a flow rate of 1 mL·min$^{-1}$. The arrow shows the time which the external potential was applied.

Along the same lines, the effect of the applied potential was also evaluated with proteins that have tendency to rearrange their structure upon adsorption as a consequence of their less structural stability. For that reason, α-LAC and Mb (classified as "soft" proteins)[8,12] were selected owing their similar molecular dimensions. In order to perform the protein adsorption, the experiment was started recording a baseline by impinging 10 mmol·L$^{-1}$ buffer solution at IEP of the examined protein on the OTCE for 20 min when no potential was applied on the electrode surface. Then, 0.10 mg·mL$^{-1}$ protein solution was pumped inside the cell at OCP and IEP with the purpose to obtain a protein monolayer. Finally, when constant readings were observed, the potential was increased to +800 mV and hold until the end of the experiments. To illustrate, experimental results are shown in FIG. 22.

As the figure shows, the attachment of the designated "soft" proteins on the OTCE surface presented significant differences between them mainly during the adsorption of the monolayer at OCP. In consequences, the adsorption data demonstrated that α-LAC formed a monolayer around 40 min after the protein injection under the tested experimental conditions while Mb made it approximately within 110 min. Additionally, the achieved monolayers displayed thickness values ($d_{\alpha-LAC}$=2.1±0.3 nm and $d_{Mb}$=0.8±0.2 nm) in line with, and lower than the molecular dimensions of α-LAC and Mb, respectively. In view of that, the adsorption behavior of α-LAC may possibly be related to favorable interactions between the protein molecules and the OTCE surface bring into being a more compact monolayer than Mb. In contrast, a not fully packed Mb monolayer concomitant to the subsequent rearrangements of the molecular structure upon protein adsorption produced a thicker protein film.

On the other hand, the applied potential induced no high differences between α-LAC and Mb during the protein adsorption on the substrate modified with the protein monolayer. Therefore, $d\Gamma/dt_1$ proved that the changing of the interfacial potential promoted a faster attraction of α-LAC (0.21±0.01 mg·m$^{-2}$·min$^{-1}$) to the electrode surface than Mb (−0.04±0.02 mg·m$^{-2}$·min$^{-1}$) which showed a negative initial slope almost certainly associated to structural rearrangements in the non-compact monolayer previously adsorbed at OCP. Even though the specific behaviors detected in both cases, a slow increase in the protein attachment was noticed after the first adsorption phase assisted by potential at the verified experimental conditions as show the Table 2. A possible reason of that performance on the adsorption process is able to be associated with the intrinsic polarizability of the selected proteins, the probability of attachment of each protein (related to the protein concentration), the rearrangement of the protein film by effect of the applied potential, and the shielding of the electric field by the adsorbed protein monolayer that may avoid the polarization of the protein molecules in the interface adjoining. Although the differences observed between α-LAC and Mb, both "soft" proteins demonstrated similar adsorption kinetics compared to the fast adsorption processes obtained with the "hard" proteins. As a result, those adsorption behaviors are able to allow the splitting up between the selected "hard" and "soft" proteins when the protein adsorption is promoted by an external potential applied.

3.3 Effect of Applied Potential on the Adsorption of BSA and Cross-linked BSA

To evaluate the adsorption of BSA (a "soft" protein)[8,9,12] induced by potential and trying to match with a comparable hard protein, BSA molecules were also cross-linked with DSS in order to obtain more structure-stable proteins. DSS is a hydrophobic and lysine specific cross-linker so it is able to be possible to cross-link the lysine residues inside the protein molecules.[38] As a result, BSA molecules can restrict the conformational degrees of freedom of the polypeptide chain that allow them to rearrange their structure after the adsorption process, and turn them to protein molecules with a higher conformational rigidity. Once more, as it was described above, the adsorption experiments were performed allowing a monolayer of either BSA (d=3.3±0.2 nm) or cross-linked BSA (d=3.7±0.3 nm) to adsorb on the OTCE at OCP (10 mmol·L$^{-1}$ citrate buffer containing 0.1 mg·mL$^{-1}$ of protein at the IEP) after a baseline was registered for 20 min. Then, the electrode potential was changed and hold until the end of the dynamic adsorption experiments as can be observed in FIG. 3.

The supplied data made evident that the cross-linked BSA displayed a better adsorption performance throughout the achieved experiment respect to the non-modified BSA. On the one hand, it is able to note that the protein monolayers previously adsorbed on the OTCE at OCP presented a slight difference in the thickness (and the adsorbed amount). That change in the adsorption behavior of BSA can be attributed to a less tendency of BSA molecules to rearrange their molecular structure subsequent to the attachment on the solid surface as a result of the cross-linking carried out by DSS. In simpler words, the restriction of the freedom of movements in the polypeptide chain generated a more structure-stable protein which avoid the unfolding of the protein molecules on the substrate. On the other side, the switch-over of the interfacial potential generated a substantial variation in the adsorption rate of the cross-linked BSA in line with the trend observed with "hard" proteins. However, the increase of the protein attachment by potential was much lower than the tendency observed with LSZ and RNase A. Consequently, it is not suitable to consider the cross-linked BSA as part of that group of proteins but it was evident that the cross-linking was able to produce a modified protein that could perform a different adsorption behavior respect to the non-modified BSA as shown in the Table 2. Thus, the experimental results could demonstrate that more restrictions to the degrees of freedom of the joint movements in the polypeptide chain were be able to be the responsible constituent of the variations observed in the BSA adsorption and the cause of the adsorption comportment tends towards a "hard protein behavior".

3.4. Effect of Applied Potential on the Adsorption of IgG and GOx

Figure 24:
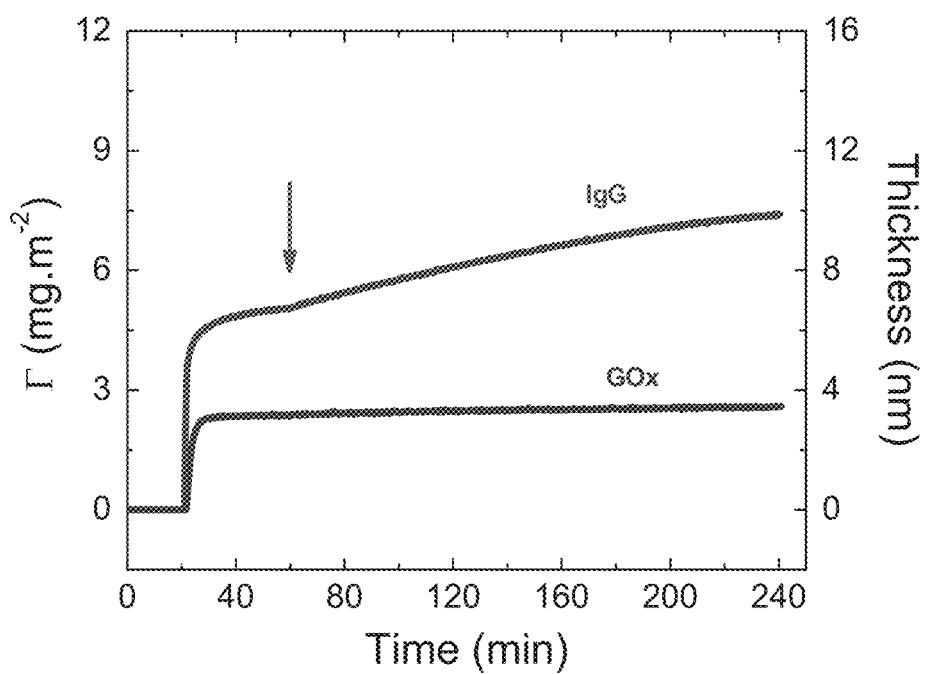
FIG. 24. Effect of applied potential on the adsorption kinetic of 0.10 mg·mL$^{-1}$ IgG and GOx after adsorption of the respective protein monolayer onto OTCE at OCP. Adsorption experiments were performed in 10 mmol·L$^{-1}$ buffer solution at IEP of the respective protein and a flow rate of 1 mL·min$^{-1}$. The arrows show the time which the external potential was applied.

The adsorption behavior between "soft" proteins was also investigated bearing in mind proteins with similar molecular weights but different molecular dimensions. For that reason, GOx (8.0×7.0×5.5 nm$^3$, MW=160 kDA) and IgG (14.2× 8.5×3.8 nm$^3$, MW=160 kDA) were designated as representative proteins of this group. Again, a protein monolayer was allowed to adsorb on the OTCE at OCP (10 mmol·L$^{-1}$ buffer solution containing 0.1 mg·mL$^{-1}$ of protein at the IEP) after a baseline was collected injecting buffer solution for 20 min. Then, +800 mV were applied at t=60 min and hold during the remaining course of the experiment. As a result, typical experimental data are shown in FIG. 24.

Given the experimental data, the adsorption processes performed by both proteins showed a totally dissimilar behavior. On the one hand, the first difference can be noticed during the adsorption of the protein monolayers onto the OTCE at OCP which accomplished thicknesses values of 3.1±0.2 nm in the case of GOx and 6.7±0.4 nm in the case of IgG. Those differences were expected and attributed to the divergent molecular dimensions between both proteins. In addition, because these proteins are more susceptible to interact with the electrode surface caused by their "soft" condition, the thicknesses of the protein monolayers were expected to be even thinner than the reported protein dimensions. On the other side, another difference was observed when the potential was switched to +800 mV. Under this condition, IgG exhibited a higher adsorption rate when the potential was applied contrary to GOx which revealed a slight change in the thickness of the monolayer as showed the dΓ/dt$_2$ and dΓ/dt$_3$ in the Table 2.

3.5. Molecular Modeling of Mb and LSZ

MD simulations of a single protein molecule were perform by making use of Mb and LSZ to study the effect of the applied potential on representative "hard" and "soft" proteins, respectively. The simulation results showed that the increase of the protein dipole moment depends on the intensity of the applied external electric field in agree with recent reports.[39,40] The higher the protein polarizability and the intensity of the external electric potential, the larger the protein dipole moment induced as shows. Specifically, when 0.424 V·nm$^{-1}$ were applied, an increase in the dipole moment of 8.0-folds and 5.5-folds was observed respect to the control condition of Mb and LSZ, respectively.

Figure 25:
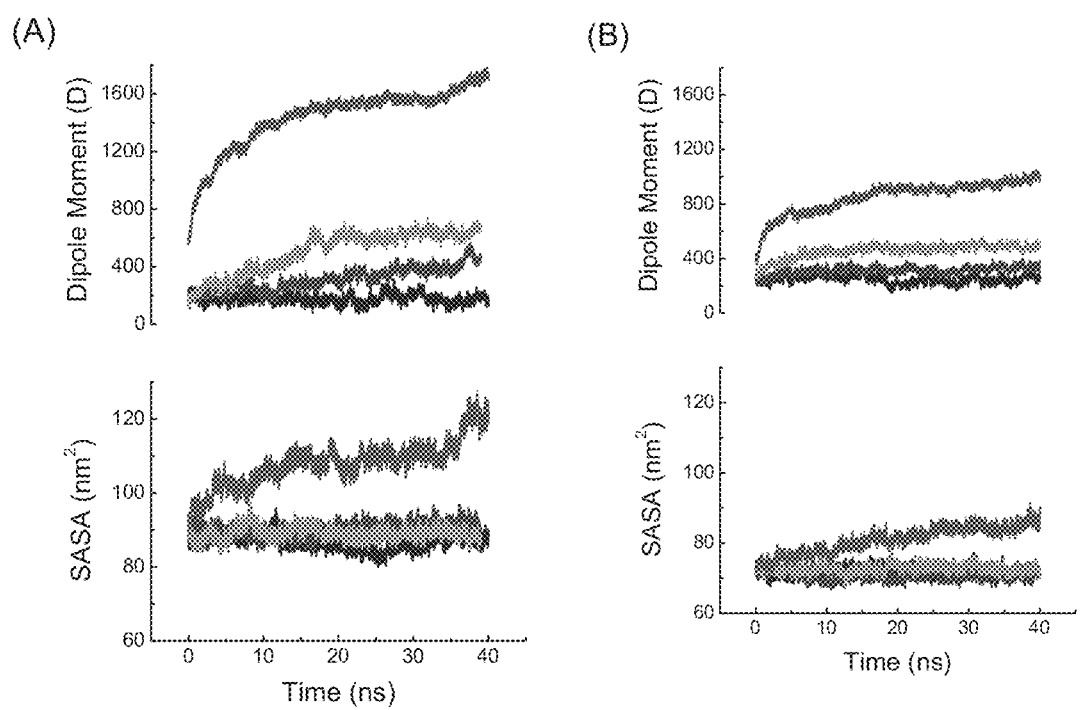
FIG. 25. Simulation of dipole moment and SASA of Mb (A) and LSZ (B) were performed at 0.075 (green line), 0.188 (orange line), and 0.424 V·nm$^{-1}$ (pink Line). The control was run when no electric field was applied to the system (blue line).

Surprisingly, the effect of electric field on the Mb dipole moment was higher than LSZ dipole moment in contrast with the trend observed experimentally. In other words, because Mb presented a less adsorbed amount respect to LSZ (see FIG. 22 and FIG. 21, respectively), a low value in the dipole moment should be expected in the case of Mb. Therefore, the dynamic simulations suggest that the protein polarization effect is not the only one factor governing the protein adsorption. For that reason, these findings seem to contradict our previous hypothesis which states that the increase of the adsorption rate due to the application of an electric field is driven by an increase in the protein polarization.[9,10] In agree with our new simulation results, that hypothesis is actually valid only for rigid proteins. Also, another important factor which plays a key role in the adsorption rate is the flexibility of the protein. In fact, Mb displayed higher values of SASA compared with LSZ (see FIG. 25). That it is why soft proteins such as Mb are able to undergo larger surface deformation than rigid proteins like LSZ. This behavior is mainly due to the significant conformational changes generated by the external field and the protein charge redistribution in agree with Bekard et al.[41] who demonstrated a major deformation of the BSA (a "soft" protein) molecules, when an external electric field was applied, compared with LSZ. As a result of the protein deformation, a large number of water molecules interacts with the Mb surface and promotes the formation of a large hydrodynamic size with the subsequent increase in the solvation energy of the protein. In view of that, both the protein dipole moment and the SASA may give a better insight onto the molecular mechanism driving protein adsorption assisted by potential.

Figure 26:
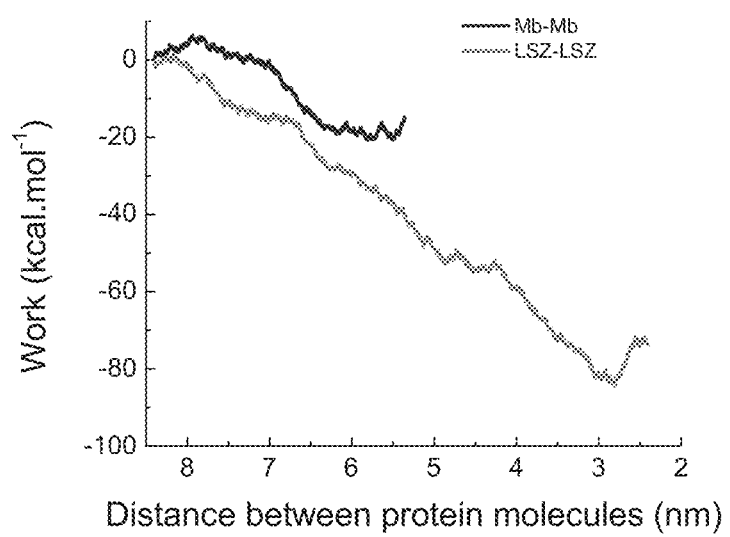
FIG. 26. Simulation of the work done during the Mb-Mb and LSZ-LSZ interactions induced by an electric field of 0.180 V·nm$^{-1}$. The initial distance between the centers of mass of both proteins was 9 nm.

Additionally, simulations of protein-protein interaction were run under the effect of an external electric field. The simulation results revealed that the work required to bring together two Mb molecules was much higher than that required for two LSZ molecules. More simply, LSZ showed stronger attractive force under the influence of the applied potential respect to Mb as shown in FIG. 26. In fact, the adsorption rate of Mb was found to be considerably lower than that observed in the case of LSZ. As a consequence, the high adsorption rate observed experimentally for LSZ is mainly driven by an increase of the dipole moment along with a low increase of the SASA. However, the low Mb adsorption rate is due to a significant increase of the SASA which cannot be overcome by even a large increase of its dipole moment. Because further analysis are required to establish the correlation between polarization and SASA effects on the protein adsorption, new simulations along this direction are currently under consideration.

4. Conclusions

Adsorption of "hard" and "soft" proteins were studied under the influence of an external potential using SE. Additionally, DM simulations were also performed to gain more insights on the adsorption behavior of both group of proteins. Considering the obtained result, the selected "hard" proteins showed an increased susceptibility to the applied potential than "soft" proteins and consequently let increase the adsorbed amount onto the OTCE. That "hard" protein behavior was able to be reproduced by the cross-linked BSA, accordingly the protein cross-linking linking allowed to the BSA molecules to restrict the degree of freedom of the joint movements and get a more rigid structure, Thus, it was possible to confirm that protein molecules with a more structural stability involves much susceptibility to the imposed electric field. Although the protein polarizability and the magnitude of applied potential are important factors to understand the protein adsorption, DM simulations demonstrated that they are not the only issues to take into account in the analysis of adsorption behavior. The simulation results suggest that the flexibility of the protein also plays a key role in the protein adsorption assisted by potential. Because "soft" proteins are highly deformable as a result of a weak internal cohesion, the effect of the applied potential produces an increase in the solvent accessible surface area (SASA) which offset the effect of the protein dipole moment. Consequently, the protein-protein interaction data (obtained by simulation) displayed stronger attractive forces by effect of the applied potential in the case of "hard" proteins respect to the "soft" proteins. In conclusion, all those variables (at least) have to be considered to understand the effect of the applied potential in the protein attachment onto the OTCE being their contributions on the adsorption process of synergistic or antagonistic type.

6. Literature Cited in this Example (1) Norde, W. *Macromol. Symp.* 1196, 103, 5.
(2) Vermeer, A. W. P.; Norde, W. *J. Colloid Interface Sci.* 2000, 225, 394.
(3) Norde, W.; Giacomelli, C. E. *J. Biotechnol.* 2000, 79, 259.
(4) Norde, W. *Coll. Surfaces B* 2008, 61, 1.
(5) Rabe, M.; Verdes, D.; Seeger, S. *Adv. Colloid Interface Sci.* 2011, 162, 87.
(6) Vogler, E. A. *Biomaterials* 2012, 33, 1201.
(7) Norde, W. *Colloids and Interfaces in Life Sciences and Bionanotechnology*; CRC Press, 2011.
(8) Norde, W.; Lyklema, J. *Advances in Colloid and Interface Science* 2012.
(9) Benavidez, T. E.; Garcia, C. D. *Langmuir* 2013, 29, 14154.
(10) Benavidez, T. E.; Torrente, D.; Marucho, M.; Garcia, C. D. *Journal of Colloid and Interface Science* 2014, 435, 164.
(11) Claesson, P. M.; Blomber, E.; Fröberg, J. C.; Nylander, T.; Arnebrant, T. *Advances in Colloid and Interface Science* 1995, 57, 161.
(12) Bos, M. A.; Shervani, Z.; Anusiem, A. C.; Giesbers, M.; Norde, W.; Kelijn, J. M. *Colloids and Surfaces B: Biointerfaces* 1994, 3, 91.
(13) Weber, K.; Osborn, M. *Journal of Biological Chemistry* 1969, 244, 4406.
(14) Kendrew, J. C.; Bodo, G.; Dintzis, H. M.; Parrish, R.; Wyckoff, H.; Phillips, D. *Nature* 1958, 181, 662.
(15) Malamud, D.; Drysdale, J. W. *Analytical Biochemistry* 1978, 86, 620.
(16) Squire, P. G.; Moser, P.; O'Konski, C. T. *Biochem.* 1968, 7, 4261.
(17) Hecht, H. J.; Kalisz, H. M.; Hendle, J.; Schmid, R. D.; Schomburg, D. *Journal of Molecular Biology* 1993, 229, 153.
(18) Pazur, J. H.; Kleppe, K. *Biochemistry* 1964, 3, 578
(19) Georganopoulou, D. G.; Williams, D. E.; Pereira, C. M.; Silva, F.; Su, T.-J.; Lu, J. R. *Langmuir* 2003, 19, 4977.
(20) Hecht, H. J.; Schomburg, D.; Kalisz, H.; Schmid, R. D. *Biosens. Bioelectron.* 1993, 8, 197.
(21) Noh, H.; Yohe, S. T.; Vogler, E. A. *Biomaterials* 2008, 29, 2033.
(22) Lv, Z.; Wang, J.; Chen, G.; Deng, L. *International Journal of Biological Macromolecules* 2010, 47, 661.
(23) Vega, R. A.; Maspoch, D.; Shen, C. K. F.; Kakkassery, J. J.; Chen, B. J.; Lamb, R. A.; Mirkin, C. A. *ChemBioChem* 2006, 7, 1653.
(24) Benavidez, T. E.; Garcia, C. D. *Electrophoresis* 2013, 34, 1998.
(25) Mora, M. F.; Reza Nejadnik, M.; Baylon-Cardiel, J. L.; Giacomelli, C. W.; Garcia, C. D. *J. Colloid Interface Sci.* 2010, 346, 208.
(26) Nejadnik, M. R.; Francis, L.; Garcia, C. D. *Electroanalysis* 2011, 23, 1462.
(27) Fujiwara, H. *Spectroscopic ellipsometry: principles and applications*; John Wiley & Sons, 2007.
(28) Hampton, M. A.; Nguyen, A. V. *Adv. Colloid Interface Sci.* 2010, 154, 30.
(29) Tyrrell, J. W. G.; Attard, P. *Phys. Rev. Lett.* 2001, 87, 176104.
(30) Borkent, B. M.; Dammer, S. M.; Schönherr, H.; Vancso, G. J.; Lohse, D. *Phys. Rev. Lett.* 2007, 98, 204502.
(31) Craig, V. S. J. *Soft Matter* 2011, 7, 40.
(32) Phillips, J. C.; Braun, R.; Wang, W.; Gumbart, J.; Tajkhorshid, E.; Villa, E.; Chipot, C.; Skeel, R. D.; Kalé, L.; Schulten, K. *Journal of Computational Chemistry* 2005, 26, 1781.
(33) Hornak, V.; Abel, R.; Okur, A.; Strockbine, B.; Roitberg, A.; Simmerling, C. *Proteins: Structure, Function, and Bioinformatics* 2006, 65, 712.
(34) Mahoney, M. W.; Jorgensen, W. L. *The Journal of Chemical Physics* 2000, 112, 8910.
(35) Gordon, J. C.; Myers, J. B.; Folta, T.; Shoja, V.; Heath, L. S.; Onufriev, A. *Nucleic acids research* 2005, 33, W368.
(36) Comer, J.; Wells, D.; Aksimentiev, A. In *DNA Nanotechnology*; Zuccheri, G., Samori, B., Eds.; Human Press: 2011; Vol. 749, p 317.
(37) Park, S.; Khalili-Araghi, F.; Tajkhorshid, E.; Schulten, K. *The Jouranl of chemical physics* 2003, 119, 3559.
(38) Huang, B. X.; Kim, H.-Y.; Dass, C. *Journal of the American Society for Mass Spectrometry* 2004, 15, 1237.
(39) Favi, P. M.; Zhang, Q.; O'Neill, H.; Mamontov, E.; Diallo, S. O. *J Biol Phy* 2014, 40, 167.

(40) Wang, X.; Li, Y.; He, X.; Chen, S.; Zhang, J. Z. *The Journal of Physical Chemistry A* 2014.
(41) Bekard, L.; Dunstan, D. E. *Soft Matter* 2014, 10, 431.

What is claimed is:

1. A method for adsorbing a protein onto a conductive solid substrate while maintaining biological activity, the method comprising
   i) coating the conductive solid substrate with an initial first layer of protein, at open circuit potential, wherein the conductive solid substrate comprises a carbon surface; and
   ii) coating the conductive solid substrate with a secondary protein layer by applying an external potential, controlled using a potentiostat, to the solid substrate, the external potential being in a range of from about +650 mV to about +850 mV vs. an Ag/AgCl/Cl$^-_{SAT}$ reference electrode and less than a potential required to oxidize the protein, in the presence of a solution comprising the protein, wherein the solution has a pH within ±2 units of the isoelectric point of the protein, wherein the solution has a protein concentration of from about 0.25 mg/mL to about 1.00 mg/mL, wherein the solution has an ionic strength of less than or equal to about 25 mM, wherein the protein adsorbs to the conductive solid substrate upon application of the external potential, wherein an adsorbed amount of protein in the secondary protein layer grows in proportion to a time of application of the external potential and wherein the external potential is applied for a period of 3 to 100 hours.

2. The method of claim 1, wherein the solution has a pH selected from the group consisting of within 1 unit of the isoelectric point, within 0.8 units of the isoelectric point, within 0.7 units of the isoelectric point, within 0.6 units of the isoelectric point, within 0.5 units of the isoelectric point, within 0.4, units of the isoelectric point, within 0.3, units of the isoelectric point, within 0.2 units of the isoelectric point, within 0.1 units of the isoelectric point, and within 0.0 units of the isoelectric point.

3. The method of claim 1, wherein the conductive solid substrate comprises a material selected from the group consisting of nanostructured carbon, optically transparent carbon electrodes (OTCE), graphene, carbon nanotubes, graphite, carbon based surfaces made from pyrolyzed paper and a substrate prepared by coating or mixing any of the aforementioned materials.

4. The method of claim 1, wherein the applied potential is in a range selected from the group consisting of +650 to +800 mV, +700 to +800 mV and +700 to +850 mV vs. the Ag/AgCl/Cl$^-_{SAT}$ reference electrode.

5. The method of claim 1, wherein the potential is applied for a period of time selected from the group consisting of 3-6 hours, 6-10 hours, 10-15 hours, 15-20 hours, 20-30 hours, 30-40 hours, 40-50 hours, 50-60 hours, 60-70 hours, 70-80 hours, 80-90 hours, and 90-100 hours.

6. The method of claim 1, wherein the concentration of protein adsorbed on the substrate is at least 0.1 mg/m$^2$.

7. The method of claim 1, wherein the protein concentration in the solution is selected from the group consisting of at least 0.25 mg/mL, at least 0.4 mg/mL, at least 0.5 mg/mL, at least 0.6 mg/mL, at least 0.7 mg/mL, at least 0.8 mg/mL, at least 0.9 mg/mL, about 1 mg/mL, and the concentration corresponding to the solubility of the protein in solution.

8. The method of claim 1, wherein the ionic strength of the solution is selected from the group consisting of less than 25 mM, less than 20 mM, less than 15 mM, less than 10 mM, less than 5 mM, less than 4 mM, less than 3 mM, less than 2 mM, less than 1 mM, less than 0.5 mM, less than 0.1 mM and 0.0 mM.

9. The method of claim 1, wherein the protein is selected from the group consisting of an enzyme, a cellular matrix protein, a messenger, and an antigenic protein.

10. The method of claim 1, wherein the solution comprises a buffer that has a buffering capacity at the pH of the solution.

11. The method of claim 1, wherein the initial rate of protein adsorption to the substrate ranges from $2\times10^{-3}$ mg m$^2$ min$^{-1}$ to $50\times10^{-3}$ mg m$^{-2}$ min$^{-1}$ within 30 minutes of application of the external potential.

12. The method of claim 1, wherein the applied external potential causes a polarization of the substrate and the initial layer of protein adsorbed to the substrate, wherein the polarized substrate and initial layer of protein adsorbed to the substrate induces a polarization of incoming protein, resulting in adsorption of the incoming protein.

13. The method of claim 12, wherein the rate of protein adsorption in step i) is greater than the rate of protein adsorption in step ii).

14. The method of claim 1, wherein the protein is selected from the group consisting of glucose oxidase (GOx), collagen, lysozyme (LSZ), RNAase, α-lactalbumin (α-LAC), myoglobin (Mb), bovine serum albumin (BSA), BSA crosslinked with disuccinimidyl subarate (DSS) and immunoglobulin G (IgG).

15. The method of claim 14, wherein the protein is selected from the group consisting of lysozyme (LSZ) and RNAase.

* * * * *